(12) United States Patent
Kaga et al.

(10) Patent No.: US 7,778,694 B2
(45) Date of Patent: Aug. 17, 2010

(54) BIOLOGICAL OPTICAL MEASUREMENT INSTRUMENT

(75) Inventors: Mikihiro Kaga, Abiko (JP); Noriyoshi Ichikawa, Moriya-machi (JP); Fumio Kawaguchi, Kashiwa (JP); Michiyuki Fujiwara, Kashiwa (JP)

(73) Assignee: Hitachi Medical Corporation, Chiba (JP)

( * ) Notice: Subject to any disclaimer, the term of this patent is extended or adjusted under 35 U.S.C. 154(b) by 947 days.

(21) Appl. No.: 11/355,017

(22) Filed: Feb. 16, 2006

(65) Prior Publication Data

US 2006/0184044 A1 Aug. 17, 2006

Related U.S. Application Data

(62) Division of application No. 09/937,842, filed on Sep. 28, 2001, now Pat. No. 7,039,454.

(51) Int. Cl.
*A61B 6/00* (2006.01)
(52) U.S. Cl. ............... 600/473; 600/407; 600/475; 600/476; 600/477
(58) Field of Classification Search ........... 600/407, 600/472, 475, 476, 477
See application file for complete search history.

(56) References Cited

U.S. PATENT DOCUMENTS

| | | | |
|---|---|---|---|
| 4,752,141 A | 6/1988 | Sun et al. | |
| 5,029,581 A * | 7/1991 | Kaga et al. | 607/89 |
| 5,124,130 A | 6/1992 | Costello et al. | |
| 5,178,153 A | 1/1993 | Einzig | |
| 5,257,991 A | 11/1993 | Fletcher et al. | |
| 5,321,501 A | 6/1994 | Swanson et al. | |
| 5,769,791 A | 6/1998 | Benaron et al. | |
| 5,803,909 A | 9/1998 | Maki et al. | |
| 5,987,351 A | 11/1999 | Chance | |
| 6,240,309 B1 | 5/2001 | Yamashita et al. | |

FOREIGN PATENT DOCUMENTS

| | | |
|---|---|---|
| JP | 62-192173 | 8/1987 |
| JP | 05-052682 | 3/1993 |
| JP | 06-059156 | 3/1994 |
| JP | 07-072350 | 3/1995 |
| JP | 07-248351 | 9/1995 |
| JP | 08-334458 | 12/1996 |
| JP | 9-098972 | 4/1997 |
| JP | 9-149903 | 6/1997 |
| JP | 11-330 | 1/1999 |

\* cited by examiner

*Primary Examiner*—Brian Casler
*Assistant Examiner*—Baisakhi Roy
(74) *Attorney, Agent, or Firm*—Antonelli, Terry, Stout & Kraus, LLP.

(57) ABSTRACT

A biological optical measurement instrument including: a measurement probe positionable to a surface of a subject, which irradiates light beams having a plurality of wavelengths from a light beam source through optical fibers onto the subject, and collects the light beams passed inside the subject from a plurality of positions to facilitate production of diagnostics from collected light beams of the subject, wherein the measurement probe is provided with probe casings which hold the optical fibers, fixing members where each respective fixing member is mateable with a respective probe casing to position the probe casings in a predetermined interval, and a support member which supports the fixing members, and wherein at least one of the respective probe casing or the respective fixing member is provided with a stopper claw to permit fixed engagement of the respective probe casing with the respective fixing member upon mating thereof.

16 Claims, 49 Drawing Sheets

(Subject side)

(Subject side)

BIOLOGICAL OPTICAL MEASUREMENT INSTRUMENT

CROSS REFERENCE TO RELATED APPLICATION

This is a divisional of U.S. application Ser. No. 09/937,842, filed Sep. 28, 2001 now U.S. Pat. No. 7,039,454. This application relates to and claims priority from Japanese Patent Application No. H11-87173, filed on Mar. 29, 1999 and No. H11-139300, filed on May 19, 1999. The entirety of the contents and subject matter of all of the above is incorporated herein by reference.

FIELD OF THE INVENTION

The present invention relates to a biological optical measurement instrument and, in particular, relates to a measurement probe for a biological measurement instrument which is advantageous when being applied to a newborn and a subject Under operation.

BACKGROUND ART

It has been demanded for long an instrument which permits measurement inside a living body easily without harming the living body in fields such as clinical medicine and brain science. For such demand, an instrument, which measures inside a living body by irradiating light having wavelength from visible to infrared onto the living body and thereafter by detecting the light passed through the living body, is, for example, disclosed in JP-A-9-98972 (hereinbelow will be referred to as document 1) and JP-A-9-149903 (hereinbelow will be referred to as document 2).

The "biological optical measurement instrument" disclosed in these documents was constituted by a modulation use semiconductor laser which generates light beams having different modulation frequencies, irradiation use optical fibers which introduce the generated light beams to a living body and irradiate the same at different positions thereof, detection use optical fibers which collect light beams passed through the living body and introduce the same to photo diodes, a measurement probe which secures the top end portions of the irradiation use and detection use optical fibers at predetermined positions on the living body, a lock-in amplifier which separates wavelength and reflection light intensity corresponding to the irradiation positions from electrical signals representing light intensity passed through the living body and outputted from the photo diodes (hereinbelow will be referred to as "living body passed light intensity signal"), an A/D converter which converts outputs of the lock-in amplifier to digital signals, and a display unit which computes relative variation amounts of oxy- and deoxy-hemoglobin concentrations at every measurement points from the living body passed light intensity signals after the A/D conversion and displays the computed relative variation amounts as a living body passed light intensity picture image (a topography picture image).

The conventional measurement probe was constituted by an optical fiber fixing member which arranges the top ends of the irradiation use optical fibers and the detection use optical fibers alternatively in a grid shape and a fixing belt which fixes the optical fiber fixing member to the living body. The optical fiber fixing member was formed, for example, from a base member of a plastic sheet having thickness of about 3 mm into a helmet or cap shape. To the optical fiber fixing member a belt was attached and through which the optical fiber fixing member was fixed to the living body.

The optical fiber fixing member is provided with a plurality of holes corresponding to a plurality of positions where the light beams are irradiated to the living body and detected therefrom and optical fiber holders were arranged in each of the holes. The optical fiber holder is constituted by a hollow shaped holder main body, a nut screw and an optical fiber fixing screw, and with the nut screw the holder main body is fixedly attached to the optical fiber fixing member. Inside the holder main body the irradiation use optical fiber or the detection use optical fiber was inserted and then fixed with the optical fiber fixing screw while softly contacting the optical fiber onto the surface of the living body.

As the result of investigation of the above referred to conventional art, the present inventors found out the following problems.

In association with the progress of the recent medical technology, many portions of a patient can be cured by an early detection, and, in particular, an inspection device which is suitable for an early detection of encephalopathy of a newborn or for monitoring cerebral thrombus during cardiac operation is keenly demanded.

For example, it has been recognized that in a case of speech impediment of a newborn caused by encephalopathy, since the portion relating to language function of a newborn has been established at an early stage, therefore, if a proper treatment has not been carried out by detecting encephalopathy before the language function establishment the newborn can not speak language in his or her entire life time. For this reason, an inspection device which permits an early detection of encephalopathy of a newborn is strongly demanded.

Further, in a case of a newborn who has born with visual disability, it is impossible to recognize the visual disability by the newborn him or herself and generally such as the parents detect the visual disability. However, it is frequently required time of about one year after the birth until the parents note the visual disability of the newborn which causes a problem with regard to early detection and early treatment.

As an inspection device which resolves the above problem, a biological optical measurement instrument, which unnecessitates fixing of a measurement portion during measurement, shows a low restraint property and permits measurement in any places and any environment, has drawn attention.

However, a conventional biological optical measurement instrument was developed under a precondition that a subject is in sitting or standing-up position, therefore, in a case of a living body such as a newborn who is difficult to be kept in sitting or standing-up position, there arises a problem which prevents correct measurement, because the contact positions between the scalp and the irradiation use and detection use optical fibers displace, when the head moves.

Likely, even during monitoring of cerebral thrombus which is caused by clogging a blood vessel in the brain with a thrombus caused during cardiac operation and being carried into the brain, since the body position of a living body is in a lateral decubitus, there also arises a problem which prevents measurement, because the contact positions between scalp and the irradiation use and detection use optical fiber displace.

Further, in a case of a living body such as a newborn whose hair is comparatively thin, it is possible to contact the irradiation use and detection use optical fibers to the scalp while comparatively easily avoiding hair, however, in a case of a living body such as an adult who has a plenty of hair and each of which is hard, there was a problem that it is difficult to avoid hair.

An object of the present invention is to provide a biological optical measurement instrument which permits biological optical measurement of a living body in lateral decubitus.

Another object of the present invention is to provide a biological measurement instrument which permits to avoid hair easily at the time when attaching a measurement probe to a living body.

Still another object of the present invention is to provide a biological optical measurement instrument which permits biological optical measurement while providing a predetermined stimulation to a subject.

A further object of the present invention is to provide a biological optical measurement instrument which permits to enhance diagnosis efficiency in the course of biological optical measurement.

The above and other objects and novel features of the present invention will become apparent from the description in the present specification and the attached drawings.

DISCLOSURE OF THE INVENTION

Among the inventions disclosed in the present application, the followings simply explain an outline of representative features:

(1) In a biological optical measurement instrument which is provided with a measurement probe which irradiates light beams having a plurality of wavelengths and introduced from a light beam source through optical fibers onto a subject and collects the light beams passed inside the subject from a plurality of positions, and produces from the collected passed light beams a living body passed light beam intensity picture image of the subject, the measurement probe is provided with an optical fiber fixing member which fixes the optical fibers in a predetermined interval and a support member which supports the optical fiber fixing member so as to permit rocking thereof.

(2) In the biological optical measurement instrument as described in above (1), the optical fiber fixing member is provided with holes for attaching the optical fibers and each of the attachment use holes is provided with another hole continuous from the attachment use hole and extending to the outer circumferential direction thereof.

(3) In the biological optical measurement instrument as described in above (1), the biological optical measurement instrument further provided with a sense stimulating means having an acoustic means which outputs a predetermined acoustic wave and/or a video means which displays a predetermined video image, and a picture image production means which causes to output stimulating output from the sense stimulation means and produces a living body passed light beam intensity picture image of the subject.

(4) In the biological optical measurement instrument as described in above (1), the biological optical measurement instrument is further provided with a display unit which displays the living body passed light beam intensity picture image.

(5) In the biological optical measurement instrument as described in above (1), the supporting member is provided with means for hanging and supporting the optical fiber fixing member.

(6) In the biological optical measurement instrument as described in above (1), the supporting member is further provided with means for changing the hanging height of the optical fiber fixing member.

With the above measures (1)-(6), since the measurement probe is constituted while separating the optical fiber fixing member which fixes the optical fibers at a predetermined interval from the supporting member which supports the optical fiber fixing member 9 while permitting rocking thereof, through adjustment of attachment position and height of the optical fiber fixing member to the supporting member, even in a case when the body position of a subject is in lateral decubitus the biological optical measurement can be performed without displacing the intervals of the optical fibers, namely, without displacing the contact positions between the top end portions of the optical fibers and the epiderm of the subject. In this instance, since the optical fiber fixing member is supported rockably with respect to the supporting member, even for a newborn who moves frequently in comparison with such as an adult, the biological optical measurement can be correctly performed.

In this instance, through the provision of the other hole in the optical fiber fixing member which is formed continuous from the optical fiber attachment hole and is extended from the attachment hole to the outside in radial direction, it makes possible to access directly to hair of the subject from the hole extendingly locating in the circumferential direction, namely, it makes possible to easily displace the hair of the subject from the hole extendingly locating in the circumferential direction, when attaching the optical fibers to the optical fiber fixing member, the top end portions of the optical fibers can be directly and easily contacted to the scalp. Namely, the efficiency of contacting work of the optical fibers to the subject is enhanced. Accordingly, diagnosis efficiency with the biological optical measurement instrument can be enhanced.

On one hand, with the provision of the sense stimulating means being provided with the acoustic means which outputs a predetermined acoustic wave or a video image means which displays a predetermined video image and the picture image production means which produces living body light beam intensity picture image of a subject in synchronism with or in asynchronism with the output from the acoustic means or the video image means, a predetermined sense stimulation can be provided to a newborn without directly attaching a sense stimulation means thereto as well as a biological optical measurement from the moment when stimulation is provided can be correctly performed, thereby, a biological optical measurement can be performed accurately while providing a predetermined stimulation to the subject.

BEST MODES FOR PRACTICING THE INVENTION

Hereinbelow, the present invention will be explained in detail together with the embodiments according to the present invention with reference to the drawings.

Further, in all of the drawings for explaining the embodiments according to the present invention ones having same functions are indicated by the same symbols and their repeating explanation is omitted.

Embodiment 1

Figure 1:
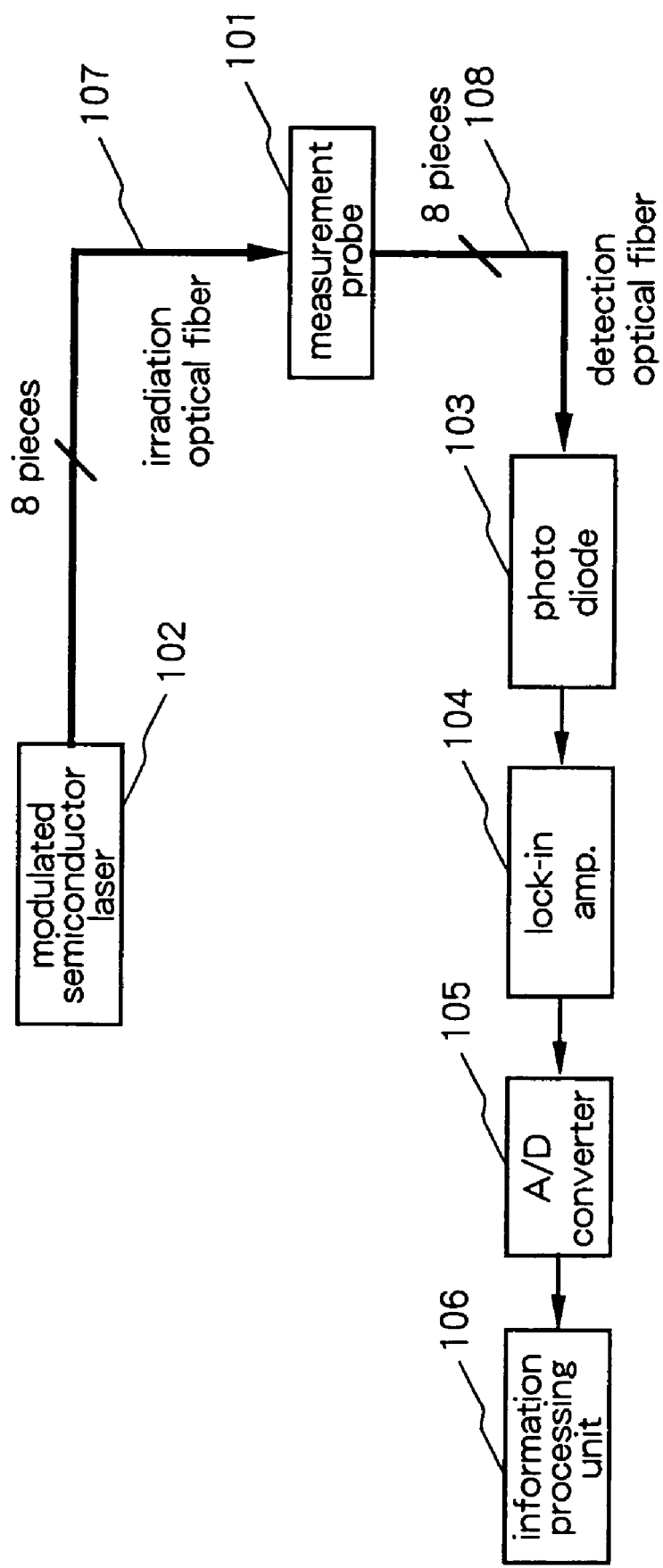
FIG. 1 is a diagram for explaining a schematic constitution of a biological measurement instrument representing embodiment 1 according to the present invention.

FIG. 1 is a diagram for explaining a schematic constitution of a biological optical measurement instrument representing embodiment 1 according to the present invention. 101 shows a measurement probe, 102 a modulated semiconductor laser, 103 a photo diode, 104 a lock-in amplifier, 105 an A/D converter, 106 an information processing unit, 107 irradiation use optical fibers, and 108 detection use optical fibers, wherein for the means and mechanism other than the measurement probe 101, well known conventional means and mechanisms are used. Further, the embodiment 1 shows a biological optical measurement instrument which images inside a brain by irradiating light beams onto the skin of the head of a newborn and detecting the same while keeping the body position of the newborn as a subject in lateral decubitus and wherein 24 measuring points are given which are defined by the intermediate points between irradiation and detection (signal reception) points.

Figure 2:
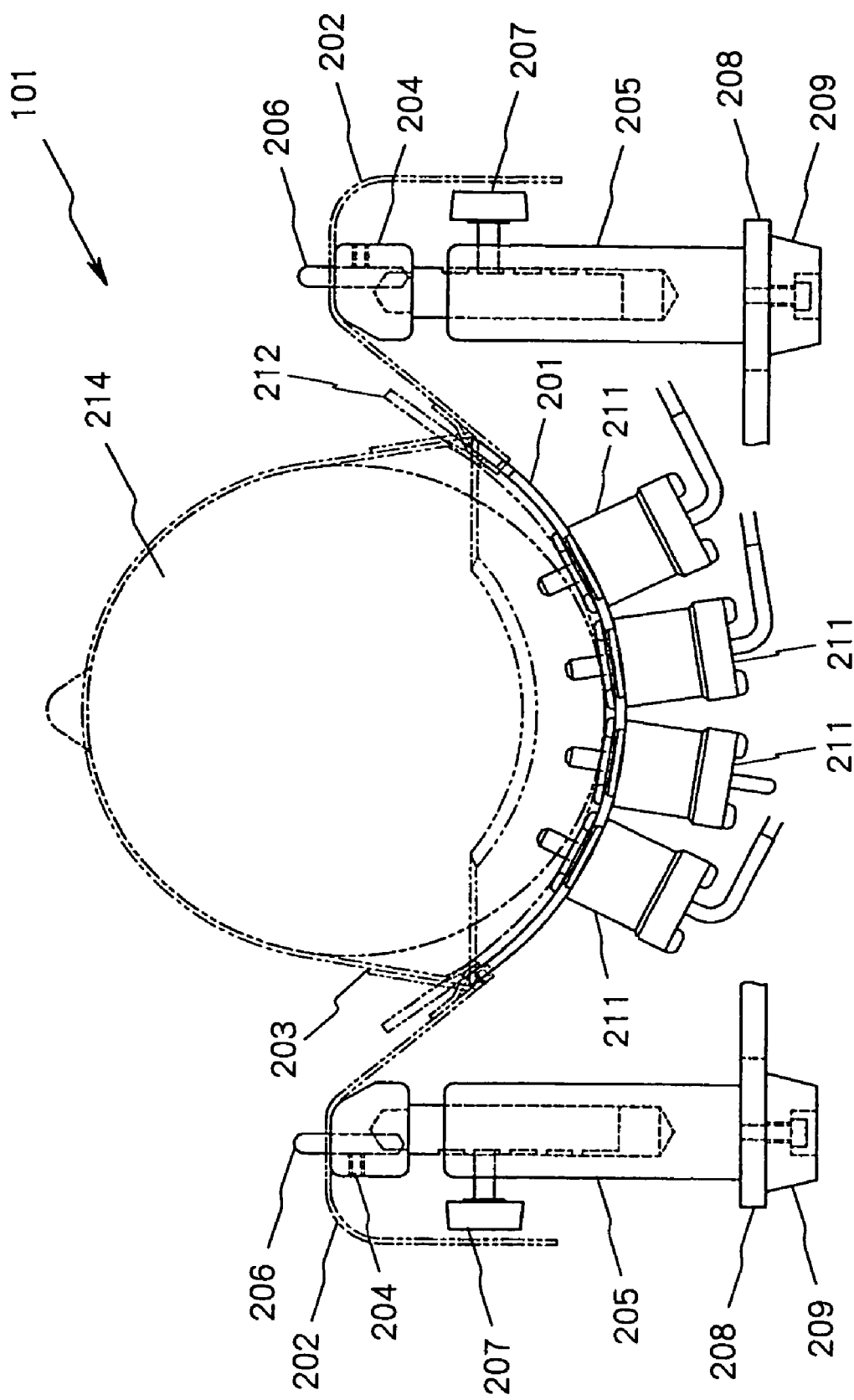
FIG. 2 is a front view for explaining a schematic constitution of a measurement probe in the embodiment 1 according to the present invention.

In FIG. 2, the measurement probe 101 in the embodiment 1 uses as the base member, for example, a plastic sheet having a thickness of about 2 mm. A shell plate 201 serving as an optical fiber fixing member which fixes the irradiation use and detection use optical fibers along the head shape of a subject is constituted in such a manner that after forming the base member in a concave shape the optical fibers 107 and 108 are fixed to the base member so that the top end portions of the irradiation use and detection use optical fibers 107 and 108 which contact to the subject at the concave side are arranged at predetermined positions. To both end portions of the shell plate 201 respective one ends of two belts are disposed and when the other ends of the belts are supported, the shell plate 201 is supported so as to permit rocking thereof in back and forth and right and left, namely, in the body axis direction of the subject and the direction perpendicular to the body axis. As a measure for supporting the other ends of the belts, two supporting columns spaced apart by a predetermined distance are provided, and with these supporting columns the other ends of the belts are supported, thereby, the head portion of a measurement object, for example, a newborn in lateral decubitus can be supported by the shell plate 201 as well as a displacement of contact positions between optical fibers and the scalp in association with a movement of the head portion during the measurement is prevented. Namely, if the shall plate 201 is supported so that the convex side of the shell plate 201 in that the back face side thereof to which the irradiation use and detection use optical fibers 107 and 108 never directly contacts to such as bed supporting the subject in lateral decubitus, a possible displacement of the contact positions between the irradiation use and detection use optical fibers 107 and 108 and the scalp is prevented.

In the measurement probe 101 of the present embodiment 1 the shell plate 201 is provided with a probe holder 211 for disposing alternately 8 pieces of irradiation use optical fibers 107 and 8 pieces of detection use optical fibers 108 in a square grid shape. Further, the detail structure of the measurement probe 101 will be explained later.

Still further, for the shell plate 201, when a plurality of shell plates having different size and different radius of curvature are prepared in advance and a person performing inspection selects one of them properly depending on the size of the head portion of a newborn serving as a measurement object, a biological optical measurement which meets the head portion of newborns of which individual size difference is comparatively large can be realized.

Now, the constitution and operation of the biological optical measurement instrument according to the present embodiment 1 will be explained based on FIG. 1.

The modulated semiconductor laser 102 is constituted by, for example, 8 pieces of optical modules provided with two semiconductor lasers, which respectively irradiate laser beams of two wavelengths of 780 nm and 830 nm. Each of the optical modules is provided with a drive circuit which drives the respective semiconductor lasers, an oscillator which applies modulation signals having respectively different frequencies to the drive circuit and provides modulation to the laser beams emitted from the respective semiconductor lasers and an optical fiber coupler which introduces light beams having wavelengths of 780 nm and 830 nm emitted from the respective semiconductor lasers into a single optical fiber (irradiation use optical fiber 107).

Accordingly, the mixed light beams having two wavelengths emitted from the modulated semiconductor laser 102 is irradiated from the top end portions of 8 pieces of irradiation use optical fibers 107 connected to the respective optical modules to the head portion of the not shown newborn serving as a subject. At this instance, the respective irradiation use optical fibers 107 are fixed to corresponding probe holders disposed on the shell plate in the measurement probe 101 and irradiate laser beams at respectively different positions on the subject.

The light beams which have passed the head portion, namely, the living body passed light beams are respectively collected by the 8 pieces of detection use optical fibers 108 fixed to the corresponding probe holders disposed on the shell plate and are introduced to the photo diodes 103. The light beams introduced into the photo diodes 103 are converted into living body passed light beam intensity signals of electrical signals representing the living body passed light beam intensity at respective photo diodes corresponding to the 8 pieces of detection use optical fibers 108 and are outputted to the lock-in amplifier 104. Further, the means for converting the light beams introduced by the 8 pieces of detection use optical fibers 108 into electrical signals is not limited to the photo diodes and any other photoelectric conversion elements such as photo multiplies can be used.

The living body passed light beam intensity signals inputted into the lock-in amplifier 104 are respectively separated into living body passed light beam intensity signals corresponding to respective wavelength and irradiation positions and are outputted to the AND converter 105. The living body passed light beam intensity signals for every wavelength and irradiation position of digitally converted by the A/D converter are stored in a not shown memory unit inside or outside the information processing unit 106. During or after ending the measurement, the information processing unit 106 computes relative variation amounts of oxy- and deoxy-hemoglobin concentrations determined from detection signals at respective measurement positions by making use of the living body passed light beam intensity signals stored in the memory unit and computes hemoglobin concentration variation values at respective measurement positions. Since, the method of computing the relative variation amounts of the oxy- and deoxy-hemoglobin concentrations from the detection signals at respective measurement positions is disclosed in the above documented 1 and 2, the detailed explanation thereof is omitted.

Thereafter, the information processing unit 106 computes the hemoglobin concentration variation values in the measurement region, for example, by means of a well known cubic spline interpolation and the result is caused to be displayed on a not shown display unit in a two dimensional picture image, thus a biological optical measurement can be easily realized even for a subject such as a newborn whose measurement in sitting position is difficult.

Figure 3:
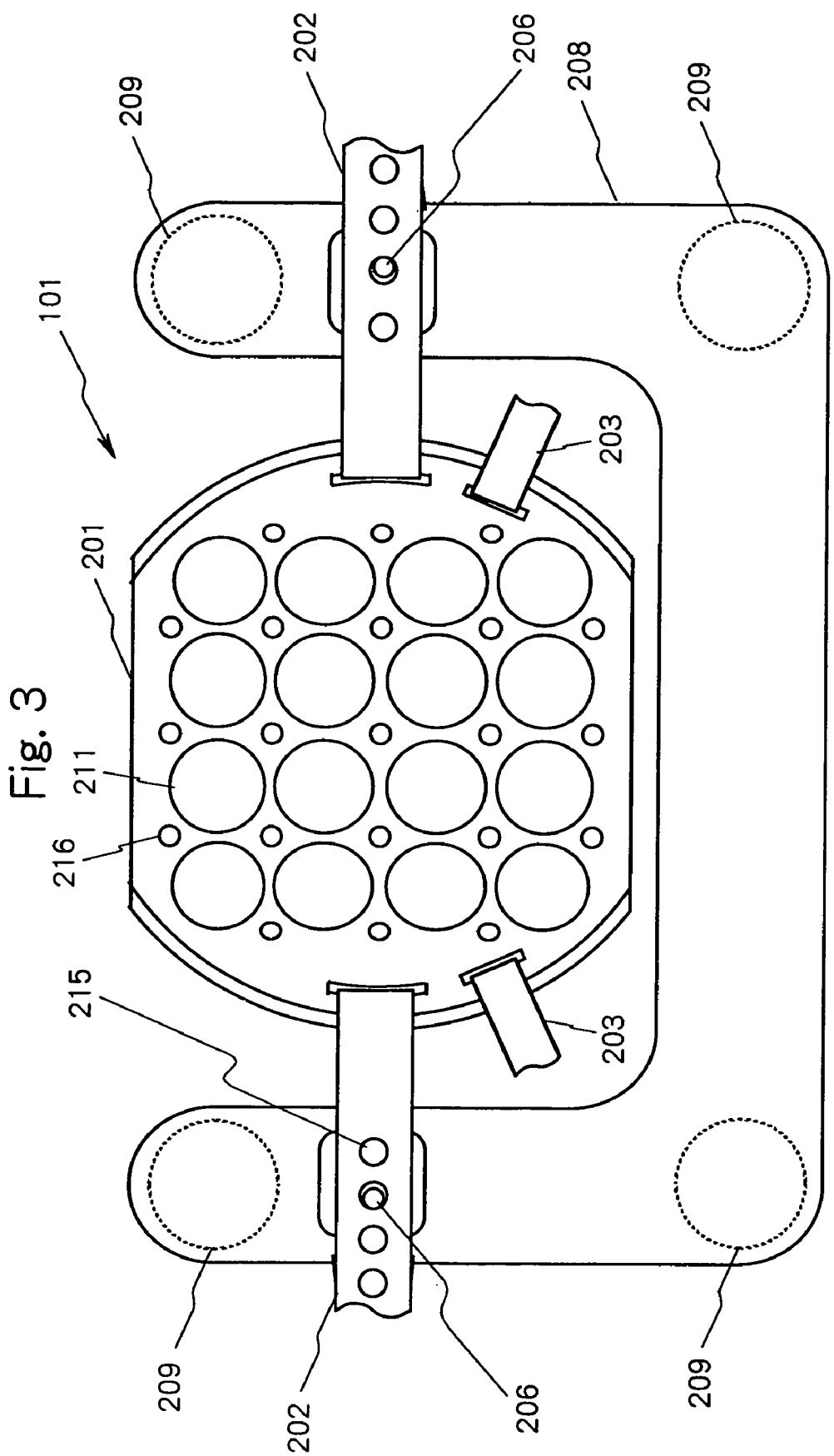
FIG. 3 is a top view for explaining a schematic constitution of the measurement probe in the embodiment 1 according to the present invention.
Figure 4:
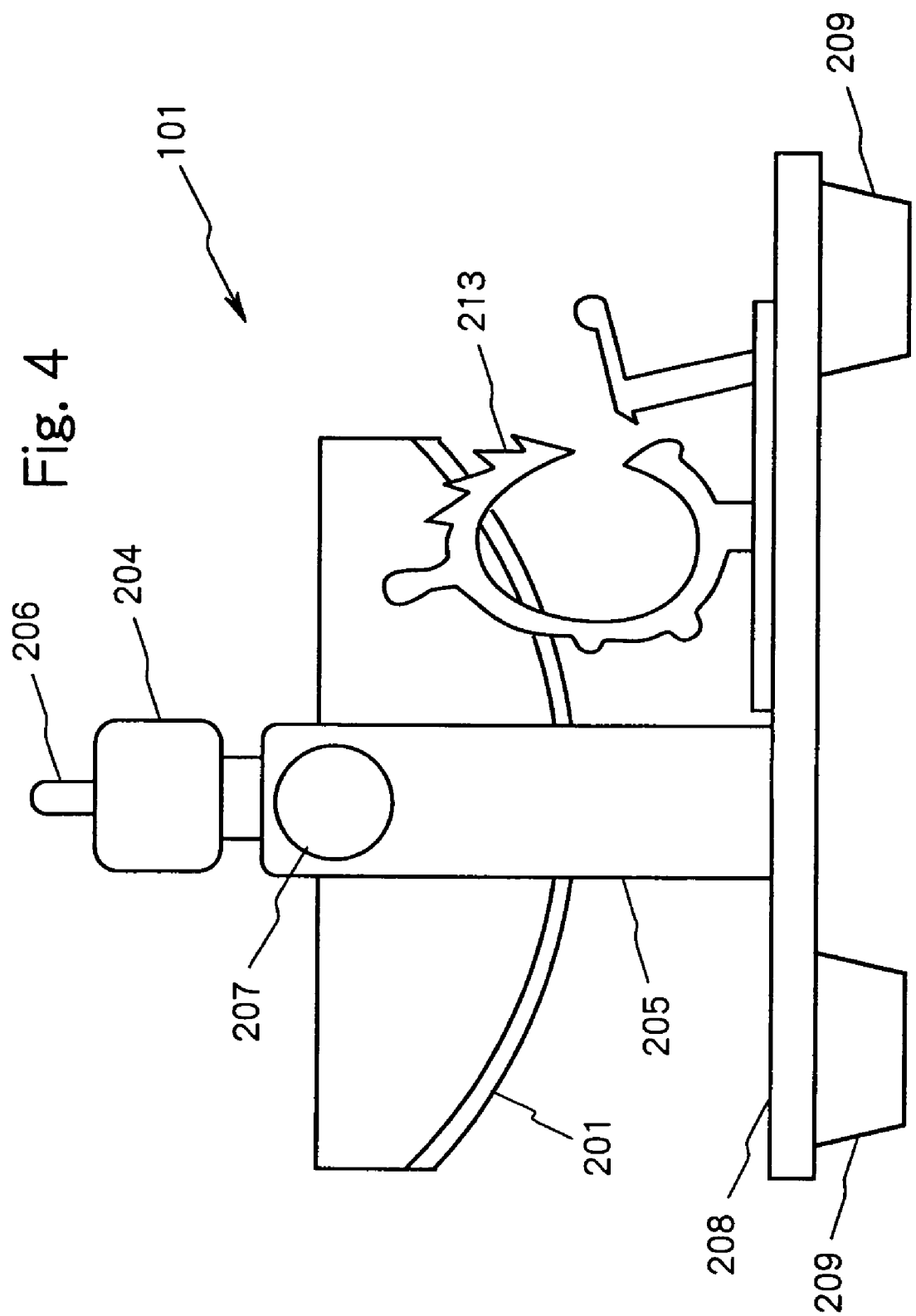
FIG. 4 is a side view for explaining the measurement probe in the embodiment 1 according to the present invention.

Now, FIG. 2 shows a front view for explaining a schematic constitution of a measurement probe 101 in the embodiment 1 and FIG. 3 is a top view for explaining a schematic constitution of the measurement probe 101 in the embodiment 1 and FIG. 4 is a side view for explaining the measurement probe 101 in the embodiment 1, and hereinbelow, based on FIG. 2 through FIG. 4, the structure and function of the measurement probe 101 according to the embodiment 1 will be explained. However, in order to simplify the explanation an illustration of the probe casing 210 to be attached to the shell plate 201 is omitted in FIGS. 3 and 4 (in this connection see FIG. 5).

In FIG. 2 through FIG. 4, 201 shows a shell plate, 202 a belt, 203 a subject fixing belt, 204 an adjustment use supporting column, 205 a supporting column, 206 a belt hanging member, 207 an adjustment screw, 208 a pillow base, 209 a rubber base, 211 a probe holder, 212 a silicone rubber sheet, 213 a cable clamp, 214 a subject, 215 holes formed in the belt 202 and 216 a hair avoiding hole (an adjustment hole).

As will be apparent from FIG. 2 through FIG. 4, the measurement probe 101 according to the embodiment 1 is constituted by an optical fiber fixing member which fixes the top end portions of the irradiation use optical fibers 107 and the detection use optical fibers 108 at predetermined positions on the head portion of the subject 214 and a supporting member which hangs and supports the optical fiber fixing member and the head portion of the subject 214 supported by the optical fiber fixing member.

The optical fiber fixing member according to the embodiment 1 is constituted by the shell plate 201, the belts 202 which hang the shell plate 201 to the supporting member, the subject fixing belt 203 which fixes the head portion of the subject 214 on the shell plate 201 and the silicone rubber sheet 212 which is disposed between the head portion of the subject 214 and the shell plate 201.

The shell plate 201 according to the present embodiment 1 uses as the base member thereof a plastic sheet having thickness of about 2 mm which is formed into a concave as has been explained above. With thus formed base member a mechanical strength which prevents deformation is realized, when the weight of the head portion of the subject 214 is supported thereby. To the shell plate 201, 16 pieces of probe holders 211 are attached which are for fixedly dispose the irradiation use optical fibers 107 and the detection use optical fibers 108 to the shell plate 201. As will be apparent from FIGS. 2 and 3, the attachment positions of these probe holders 211 are arranged in a grid shape along the surface configuration of the shell plate 201. Further, in the embodiment 1, since total of 16 pieces of optical fibers of 8 pieces of the irradiation use optical fibers 107 and 8 pieces of the detection use optical fibers 108 are used, 16 pieces of probe holders 211, the detailed structure of which will be explained later, are attached to the shell plate 201.

Further, when performing a biological optical measurement, it is necessary to directly contact the top end portions of the irradiation use and detection use optical fibers 107 and 108 to the scalp, in that the skin surface of the subject. Namely, it is known that when there exists such as hair between the optical fibers 107 and 108 and the scalp the irradiation light beams or the detection light beams are interrupted, and the measurement accuracy is greatly reduced or the measurement itself is prevented. However, in the shell plate 201 according to the embodiment 1, a plurality of the hair avoiding holes 216 are formed together with the probe holders 211 and the hair of the subject 214 can be displaced through the hair avoiding holes 216, thereby, the top end portions of the optical fibers 107 and 108 can be easily contacted onto the scalp. Namely, the efficiency of contacting work of the optical fibers 107 and 108 to the subject is enhanced. Accordingly, diagnosis efficiency with the biological optical measurement instrument according to the embodiment 1 can be enhanced.

Further, since the hair avoiding holes 216 functions as vent holes during the measurement, a possible load induced to the subject is reduced, even if the measurement time is prolonged.

At the both end portions of the shell plate 201, two holes one for the belt 202 and the other for the subject fixing belt 203 are provided. In particular, in the shell plate 201 according to the embodiment 1, the two holes for the belts 202 are formed in such a manner that a straight line connecting the two holes for passing the belts 202 runs through or near the center of the shell plate 201, therefore, an advantage, that when the head portion of the subject is placed on the shell plate 201, the safety for the subject can be increased, is achieved.

A plurality of holes 215 are formed on the belt 202 along the extending direction thereof, therefore, when a proper hole 215 to be hooked to the belt hooking member 206 formed at the top end portion of the adjustment supporting column 204 is selected, the rockable amount of the shell plate 201 is freely adjusted. At this instance, since the shell plate 201 can be rotated around the body axis of the subject 214, it is possible to perform an angle adjustment, in that an inclination adjustment of the shell plate 201 in response to the body position of the subject 214. Further, the height of the shell plate 201 can be adjusted. However, if the height of the shell plate 201 is adjusted by adjusting the let-off amount of the adjustable support column 204 which will be explained later, the rocking freedom of the shell plate 201 can be adjusted easily.

The subject fixing belt 203 is formed by a resin series material having comparatively small elasticity, thereby, even if the measurement time is comparatively prolonged, a possible load induced to the subject 214 by continuously fastening the head portion of the subject 214 can be reduced. However, even in a case when the subject fixing belt 203 is formed by such as rubber having a large elasticity, if it is always concerned to limit the fastening force, the possible load is, of course, reduced.

The silicone rubber sheet 212 is a sheet for preventing the comparatively hard shell plate 201 and probe holders 211 from directly contacting the scalp and further functions as a cushioning and a non-slip member. The silicone rubber sheet 212 is provided with holes at the positions corresponding to the attachment positions of the probe holders 212 for passing therethrough the irradiation use optical fibers 107 and the detection use optical fibers 108 and other not shown holes corresponding to the hair avoiding holes, and through these holes the top ends of the optical fibers are contacted to the scalp of the subject 214.

On one hand, the supporting member according to the embodiment 1 is constituted by the supporting column 205, the adjustable supporting column 204, the belt hook member 206, the adjustment screw 207, the pillow base 208 and the rubber base 209.

As will be seen from FIGS. 2 and 3, the pillow base 208 uses as the base member, for example, an aluminum plate having thickness of about 5 mm, and the base member is formed in a U shape, thereby, a freedom when disposing the measurement probe 101 at the head portion of the subject 214 is kept. At the back face of the pillow base 4 pieces of rubber legs 209 are respectively arranged at the corners thereof, and with these rubber legs 209 the measurement probe 101 according to the embodiment 1 is prevented from slipping during the measurement as well as vibration transmission to the shell plate 201 is prevented which may displace the positions of the optical fibers 107 and 108.

On the two opposing sides of the pillow base 208, the supporting columns 205 are attached on the respective front faces thereof in up-right direction. In the supporting column 205 a cylindrical hole is formed along its extending direction as well as the adjustment screw 207 is disposed at the side face of the supporting column 205 directing to the center thereof.

One end of the adjustment supporting column 204 is formed into a circular column which fits into the cylindrical hole formed in the supporting column 205, and at the side face thereof a plurality of grooves are formed. Namely, in the supporting member according to the embodiment 1, through adjustment of the let-off amount of the adjustment support column 204 from the support column 205 and by fitting the adjustment screw 207 into one of the grooves, the height of the shell plate 201 can be freely adjusted as well as the inclination of the shell plate 201 can be adjusted. However, as mentioned previously, the inclination of the shell plate 201 can also be adjusted by selecting the holes 215 formed at the belts 202.

On the other hand, the other end of the adjustment support column 204 is formed in a cuboid shape and all of the corners thereof to which the belt 202 may contact are rounded, and the top portion, in that end portion thereof is formed in a curved shape to constitute the cylindrical belt hooking portion 206. Thus, in the embodiment 1, the corners at the other end of the adjustment support column 204, in that the side where the belt 202 is attached are rounded, a possible wear of the belts 202 is prevented. Further, the diameter of the belt hook portion 206 is formed smaller than the diameter of the holes 215 formed at the belt 202 and through proper selection of one of a plurality of holes 215 formed at the belt 202, the adjustment as explained previously can be performed.

As will be seen from the above, in the supporting member according to the embodiment 1, by means of the support column 205 and the adjustment support column 204 the necessary height of the shell plate 201 being hanged in the air is obtained.

Further, in the support member according to the embodiment 1, a well known cable clamp 213 for bundling the irradiation use optical fibers 107 and the detection use optical fibers 108 is disposed. The cable clamp 213 is disposed at the front face of one of shorter sides of the pillow base 208 so as to bundle the optical fibers 107 and 108 in the attachment direction of the belts 202, in that the limited movement direction of the shell plate 201 to thereby prevent a possible application of unwanted force onto the optical fibers 107 and 108.

Figure 5:
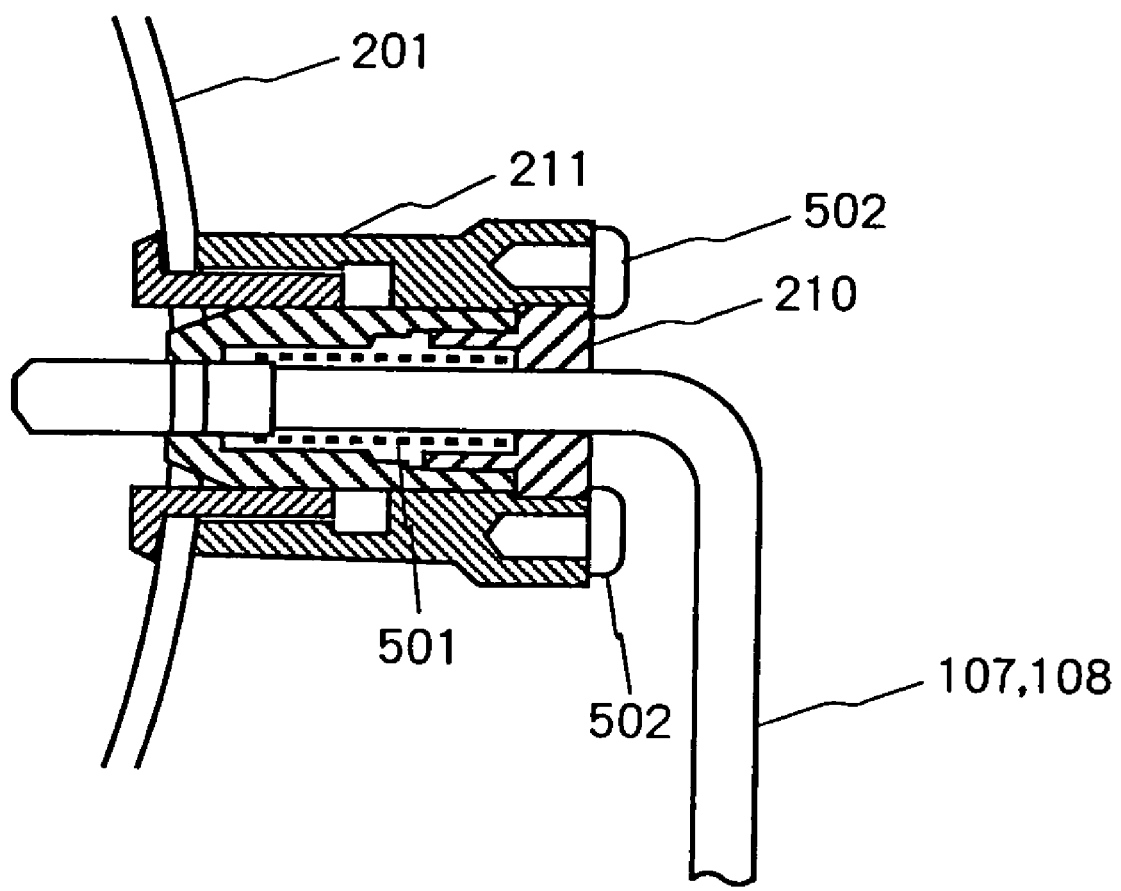
FIG. 5 is a vertical cross sectional side view for explaining a schematic constitution of a probe holder and a probe casing in the embodiment 1 according to the present invention.

FIG. 5 is a vertical cross sectional side view for explaining a schematic structure of a probe holder 211 and a probe casing 210 in the embodiment 1, wherein 210 shows the probe casing, 503. a spring mechanism and 502 a case cap screw.

As will be seen from FIG. 5, the probe casing 210 is formed in a cylindrical shape, and the diameter of the side face at one end thereof is formed to be reduced gradually toward the end thereof. Further, in the inner circumferential portions in the respective probe casings 210 a well know spring mechanism 501 is built-in and the movable side of the spring mechanism 501 is secured to the concerned optical fiber. In this instance, the movable side of the spring mechanism secured to the optical fiber acts to push out the top end portion of the optical fiber to the side where the diameter of the probe casing 210 gradually reduces, in that to the side causing the same to contact to the subject 214.

Accordingly, with the measurement probe 101 according to the embodiment 1, under the attachment state of the probe casing 210 into the probe holder 211, if the shell plate 201 is moved up and down and right and left while pressing the same onto the head portion of the subject 214, a possible hair caught between the scalp and the top end portions of the optical fibers 107 and 108 can be easily avoided. Namely, the hair caught between the scalp and the top end portion of the optical fibers once moves out in association with the movement of the shell plate 201, rending of the optical fibers on the hair is prevented by the pressing force of the spring mechanism, thereby, the top end portions of the optical fibers 107 and 108 can be easily contacted onto the scalp.

On one hand, the probe holder 211 is also formed in a cylindrical shape, and one end thereof is secured to the shell plate 201 and at the other end thereof the case cap screws 502 are disposed which, after inserting the probe casing 210 into the probe holder 211, retain the same therein.

Further, in the embodiment 1, the extending direction of the belt hook portion 206 is constituted to align with the extending direction of the support column 205, however, like the belt hook portion 206 in the embodiment 2 which will be explained later, when the top end portion is bent in L shape, an easy unhooking of the belt 202 can be prevented.

Figure 6:
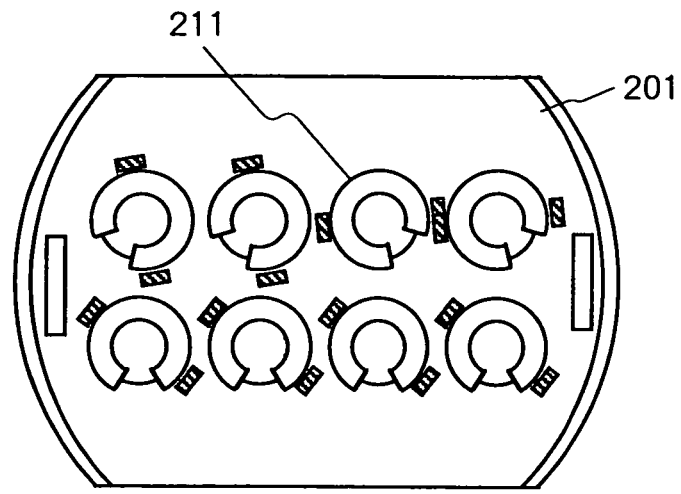
FIGS. 6(a), 6(b) and 6(c) are views for explaining a relationship between a shell plate and a silicone rubber sheet in the embodiment 1 according to the present invention.
Figure 6:
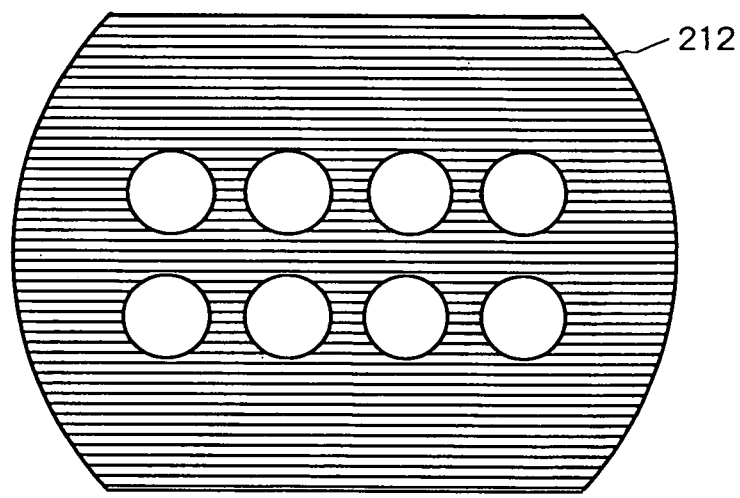
Figure 6:
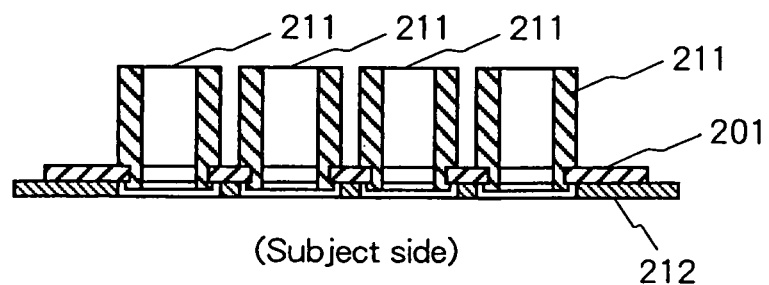
Figure 7:
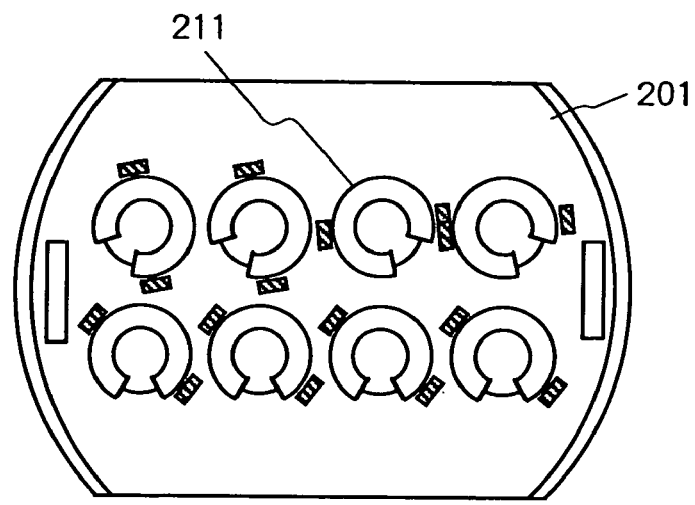
FIGS. 7(a), 7(b) and 7(c) are views for explaining a schematic constitution of another silicone rubber sheet in the embodiment 1 according to the present invention.
Figure 7:
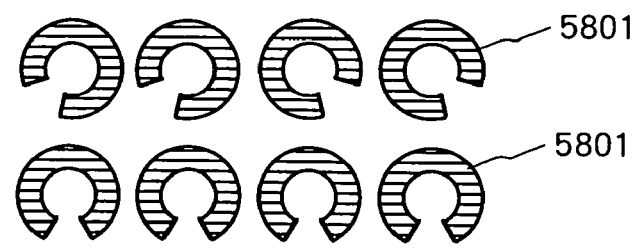
Figure 7:
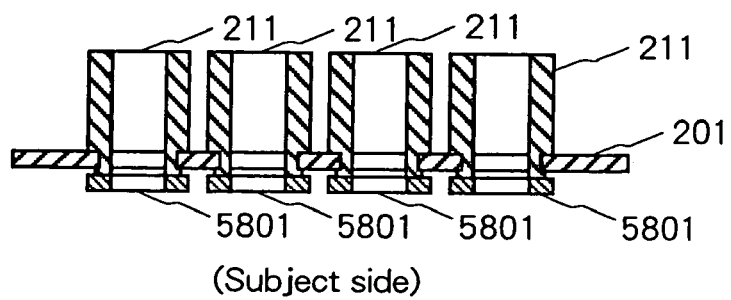

Further, in the embodiment 1, the silicone rubber sheet 212, to which holes are provided at the positions of the probe holders 211 arranged on the shell plate 201 as shown in FIGS. 6(a) and 6(b), is, for example, constituted to be disposed between the subject 214 and the shell plate 201 as shown in FIG. 6(c), however, the constitution thereof is never limited thereto, for example, silicone rubbers 5801 formed in C shape similar to the back face configuration of the probe holder 211 as shown in FIGS. 7(a) and 7(b) can of course simply secured at the back side of the probe holder 211 as shown in FIG. 7(c). Further, for the silicone rubber 5801 and the silicon rubber sheet 212 other interposing member such as sponge having elasticity and slip preventing effect can be of course used.

Further, when a probe holder 211 is formed in an incomplete circle by cutting a part thereof as shown in FIGS. 6(a) and 7(a), it is possible to access directly to the fixing use holes for the probe holder 211, therefore, hair caught between the scalp and an optical fiber can be displaced from the cut-out portion without specifically providing the hair avoiding holes.

Embodiment 2

Figure 8:
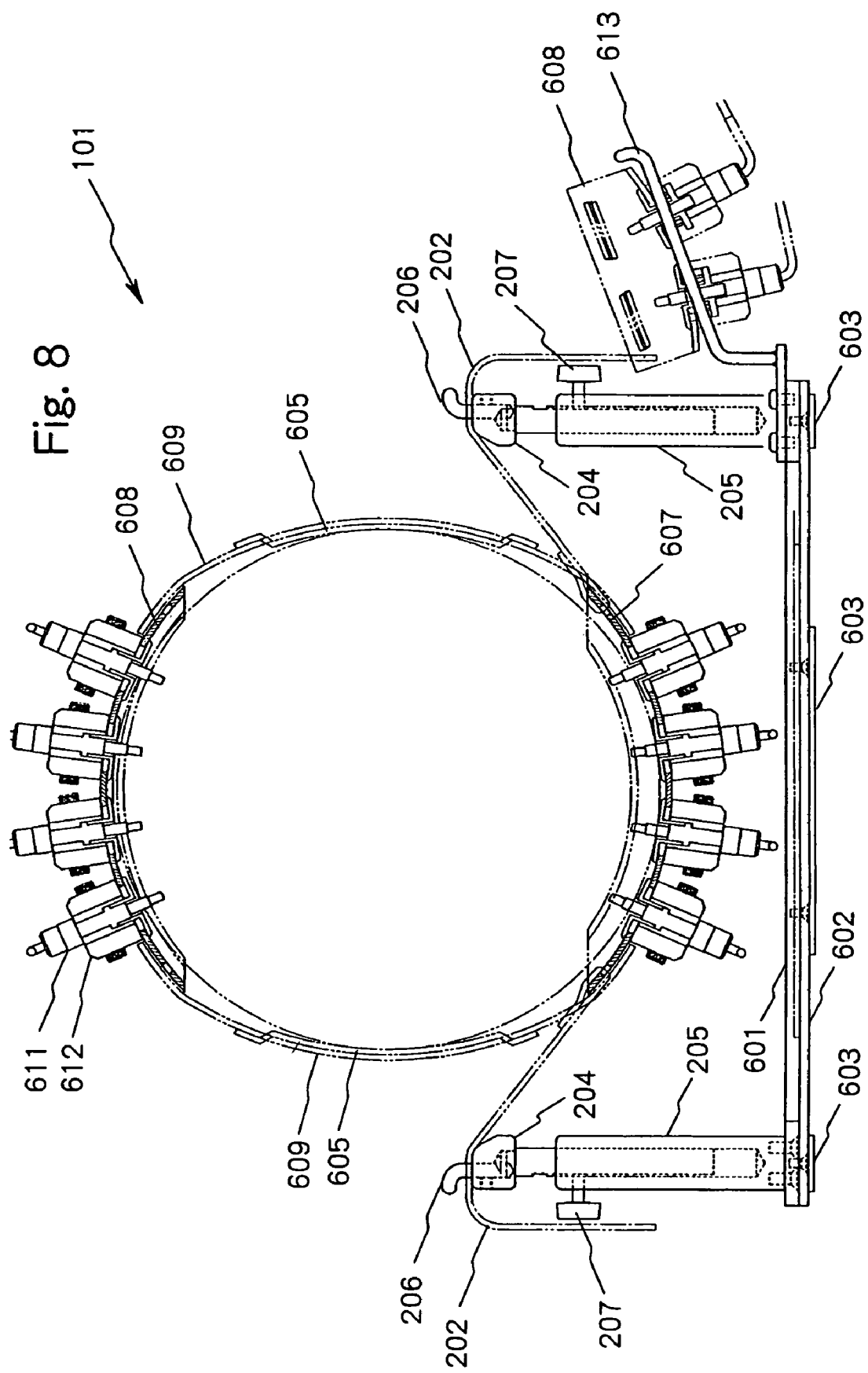
FIG. 8 is a front view for explaining a schematic constitution of a measurement probe for a biological measurement instrument representing embodiment 2 according to the present invention.
Figure 9:
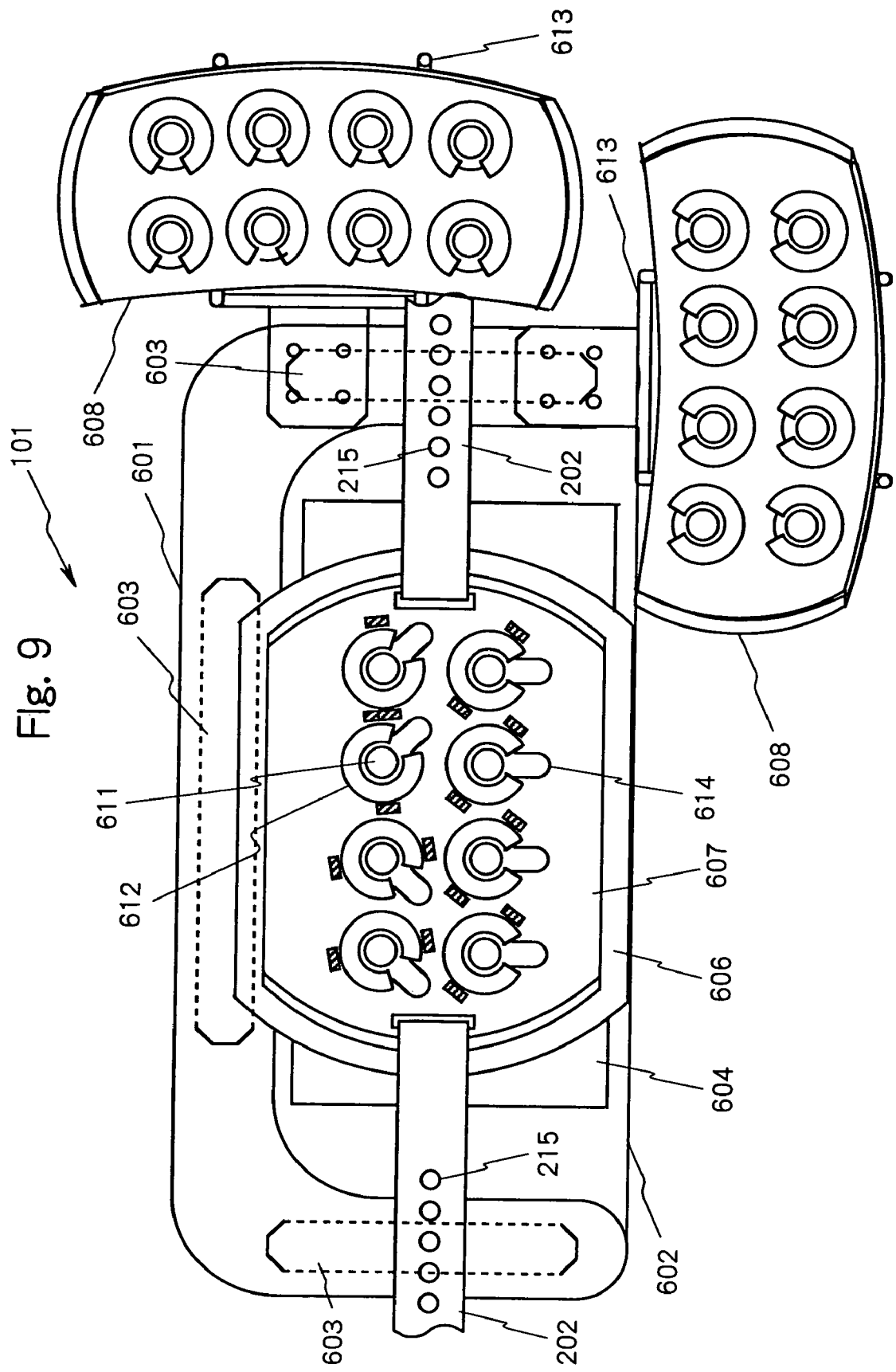
FIG. 9 is a top view for explaining a schematic constitution of the measurement probe for a biological optical measurement instrument representing the embodiment 2 according to the present invention.
Figure 10:
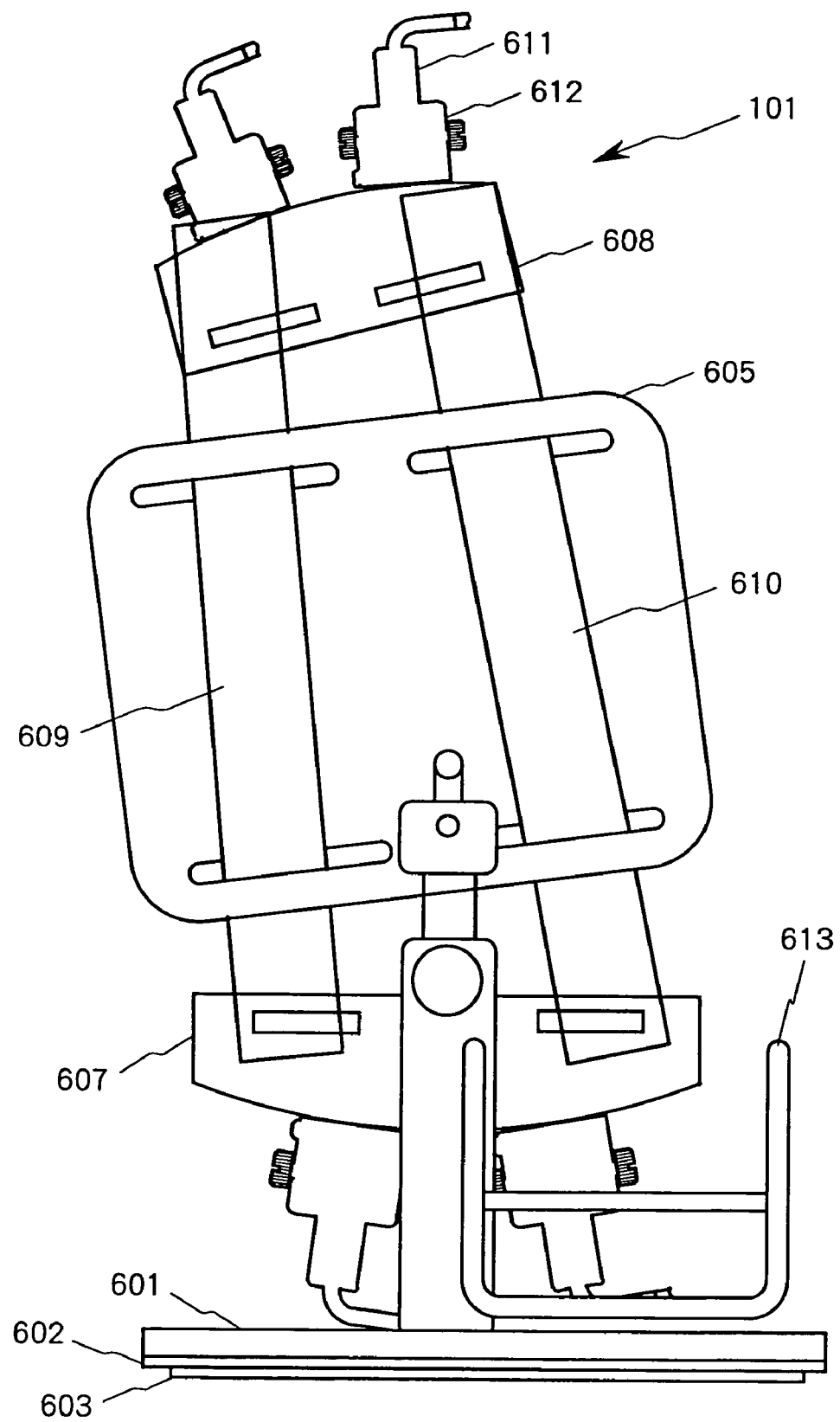
FIG. 10 is a side view for explaining a schematic constitution of the measurement probe for a biological optical measurement instrument representing the embodiment 2 according to the present invention.

FIG. 8 is a front view for explaining a schematic constitution of a measurement probe 101 for a biological measurement instrument representing embodiment 2 according to the present invention, FIG. 9 is a top view for explaining a schematic constitution of the measurement probe 101 for a biological optical measurement instrument representing the embodiment 2 according to the present invention, and FIG. 10 is a side view for explaining a schematic constitution of the measurement probe for a biological optical measurement instrument representing the embodiment 2 according to the present invention. However, in the following only the portion of the measurement probe 101 of which structure is different from that in the biological optical measurement instrument of embodiment 1 will be explained. In FIGS. 8 through 10, 601 shows a first pillow base, 602 a second pillow base, 603 a rubber plate, 604 a mirror, 605 a first silicone rubber plate, 606 a second silicone rubber plate, 607 a first shell plate, 608 a second shell plate, 609 a first fixing belt, 610 a second fixing belt, 611 a probe casing, 612 a probe holder, 613 a shell plate carrying stand and 614 hair avoiding holes.

An optical fiber fixing member according to the embodiment 2 is constituted by the first silicone rubber plate 605, the second silicone rubber plate 606, the first shell plate 607, the second shell plate 608, the first fixing belt 609, the second fixing belt 610 and the belts 202.

Like the shell plate 201 according to the embodiment 1, the first shell plate 607 and the second shell plate 608 use as the base member thereof a plastic sheet having thickness of, for example, about 3 mm which is formed into a concave shape. With thus formed base member a mechanical strength which prevents deformation is realized, when the weight of the head portion of a not shown subject is supported thereby.

Like the shell plate 201 according to the embodiment 1, to the first shell plate 607 and the second shell plate 608 respectively 8 pieces of probe holders 612 are attached which are for fixedly disposing the irradiation use optical fibers 107 and the detection use optical fibers 108 to the first shell plate 607 and the second shell plate. Like the embodiment 1, the attachment positions of these probe holders 612 are arranged in a grid shape along the surface configuration of the first shell plate 607 and the second shell plate 608. Further, in the same way as in the biological optical measurement instrument according to the embodiment 1, since total of 16 pieces of optical fibers of 8 pieces of the irradiation use optical fibers 107 and 8 pieces of the detection use optical fibers 108 are used, 8 pieces of probe holders 612 the detailed structure of which will be explained later are respectively attached to the shell plates 607 and 608.

In the shell plate 607 a plurality of the hair avoiding holes 614 are formed which extend from the holes of the probe holders 612 and the not shown hair of the subject can be displaced through the hair avoiding holes 614, thereby, the top end portions of the irradiation use and detection use optical fibers 107 and 108 attached to the first shell plate 607 can be directly contacted onto the scalp, thereby, the efficiency of contacting work is enhanced. Accordingly, diagnosis efficiency with the biological optical measurement instrument according to the embodiment 2 can be enhanced. Further, since the hair avoiding holes 614 functions as vent holes during the measurement like the hair avoiding holes 216 according to the embodiment 1, a possible load induced to the subject is reduced, even if the measurement time is prolonged. In the embodiment 2, since the occipital, in that the bottom side of the head of the not shown subject is to be disposed on the first shell plate 607, the hair avoiding holes 614 are only provided for the first shell plate 607 in connection with which working efficiency possibly reduces. However, the hair avoiding holders 614 can of course be provided for the second shell plate 608.

At the both end portions of the first shell plate 607, each one hole is provided for passing the belt 202, the first fixing belt 609 and the second fixing belt 610. On one hand, at the both ends of the second shell plate 608, each one hole for passing the first fixing belt 609 and the second fixing belt 610 is provided. In the embodiment 2, like the embodiment 1, the two holes for the belts 202 are formed in such a manner that the belts 202 runs through or near the center of the first shell plate 607 which is designed to support the head portion of the subject.

Further, also in the embodiment 2, a plurality of holes 215 are formed on the belt 202 along the extending direction thereof, therefore, when a proper hole 215 to be hooked to the belt hooking member 206 formed at the top end portion of the adjustment supporting column 204 is selected, the rockable amount of the first shell plate 607 is freely adjusted. At this instance, since the first shell plate 607 can be rotated around the body axis of the subject 214, it is possible to perform an inclination adjustment of the first shell plate 607 in response to the body position of the subject. Further, the height of the first shell plate 607 can be adjusted. However, if the height of the first shell plate 607 is adjusted by adjusting the let-off amount of the adjustable support column 204 like the embodiment 1, the rocking freedom of the first shell plate 607 can be adjusted easily.

Like the subject fixing belt 203 in the embodiment 1, the first fixing belt 609 and the second fixing belt 610 are formed by a resin series material having comparatively small elasticity, thereby, even if the measurement time is comparatively prolonged, a possible load induced to the subject by continuously fastening the head portion of the subject can be reduced. However, even in a case when the first fixing belt 609 and the second fixing belt 610 are formed by such as rubber having a large elasticity, if it is always concerned to limit the fastening force, the possible load is, of course, reduced.

With the first and second fixing belts 609 and 610, the first and second shell plate 607 and 608 are fixed to the not shown subject, thereby, even if the subject moves, it is prevented to displace the contact positions easily between the top end positions of the irradiation use and detection use optical fibers 107 and 108 and the scalp. In particular, in the embodiment 2, since the first and second shell plates 607 and 608 are fixed by the two fixing belts of the first and second fixing belts 609 and 610, an advantage that the contact position displacement is hardly caused.

The first silicone rubber plate 605 is a plate for preventing the first and second fixing belts 609 and 610, which are hard because of a comparatively low elasticity, from touching such as ears of the subject, and at the both ends thereof holes for passing the first and second fixing belts 609 and 610 are formed.

The second silicone rubber plate 606, like the silicone rubber sheet 212 in the embodiment 1, is a plate for preventing the comparatively hard first shell plate 607 and probe holders 612 from directly contacting the scalp and further functions as a cushioning and a non-slip member. The second silicone rubber plate 606 is provided with not shown holes at the positions corresponding to the attachment positions of the probe holders 612 for passing therethrough the irradiation use optical fibers 107 and the detection use optical fibers 108, and through these holes the top ends of the optical fibers are contacted to the scalp of the subject.

Thus, through the biological optical measurement making use of the measurement probe 101 according to the embodiment 2 and from a two dimensional picture image representing hemoglobin concentration variation value in a measurement region which is obtained from the light beams passed through a living body and collected by the detection use optical fibers 108 disposed on the first shell plate 607, functions relating to the occiput can be measured. On the other hand, from a two dimensional picture image representing a hemoglobin concentration variation value in a measurement region which is obtained from light beams passed through the living body and collected by the detection use optical fibers 108 disposed on the second shell plate 608, functions relating to the sinciput can be measured. Thereby, the biological optical measurement instrument making use of the measurement probe 101 according to the embodiment 2 is suitable, for example, for monitoring a brain in a broad area such as caused by being carried into the brain a thrombus caused during operation (in particular, cardiac operation) and clogging a blood vessel in the brain.

On one hand, the supporting member according to the embodiment 2 is constituted, in addition to the supporting column 205, the adjustable supporting column 204, the belt hook member 206 and the adjustment screw 207 in embodiment 1, by the first pillow base 601, the second pillow base 602, the rubber base 603, the mirror 604 and the shell plate carrying stand 613.

As will be seen from FIGS. 8, 9 and 10, the first pillow base 601 uses as the base member, for example, an aluminum plate having thickness of about 5 mm like the pillow base 208 in the embodiment 1, and the base member is formed in a U shape, thereby, a freedom when disposing the measurement probe 101 at the head portion of the subject is kept.

The second pillow base 602 uses as the base member, for example, an aluminum plate having thickness of about 3 mm and is formed in a rectangular shape, thereby, an area for disposing the first pillow base 601 and the mirror 604 on the upper side face of the second pillow base 602 is ensured. At the back face of the second pillow base 602, 3 pieces of rubber plates 603 are arranged along the first pillow base 601, and with these rubber plates, like the rubber legs 209 in the embodiment 1 the measurement probe 101 according to the embodiment 2 is prevented from slipping during the measurement as well as vibration transmission to the first shell plate 607 is prevented which may displace the positions of the optical fibers 107 and 108.

As will be seen from FIGS. 8 and 10, on the upper face of the first pillow base 601 the shell plate carrying stand 613 is disposed which is for keeping temporarily the second shell plate 608 when the measurement probe 101 is not used. The shell plate carrying stand 613 is constituted in such a manner that column shaped body extending upward from the upper face of the first pillow base 601 is at first bent in the direction substantially in parallel with the first shell plate 607 and the top end portions thereof is then bent upward again so as to be located in parallel with the first pillow base 601.

The mirror 604 disposed on the upper face of the second pillow base 602 is used for confirmation when performing the hair avoiding under the condition when a subject is placed on the first shell plate 607, thereby, the top ends of the optical fibers can be surely contacted to the scalp as well as work efficiency therefor is enhanced.

Figure 11:
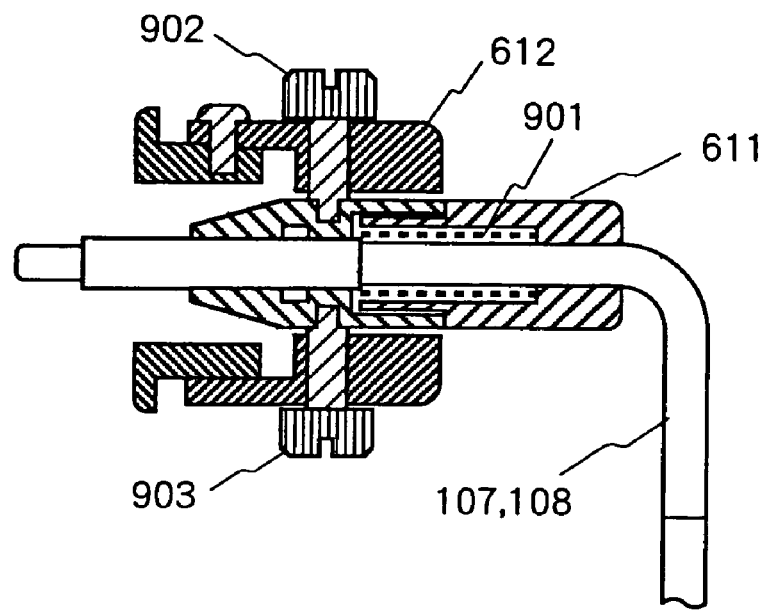
FIGS. 11(a) and 11(b) are views for explaining a schematic constitution of a probe holder and a probe casing in the embodiment 2 according to the present invention.
Figure 11:
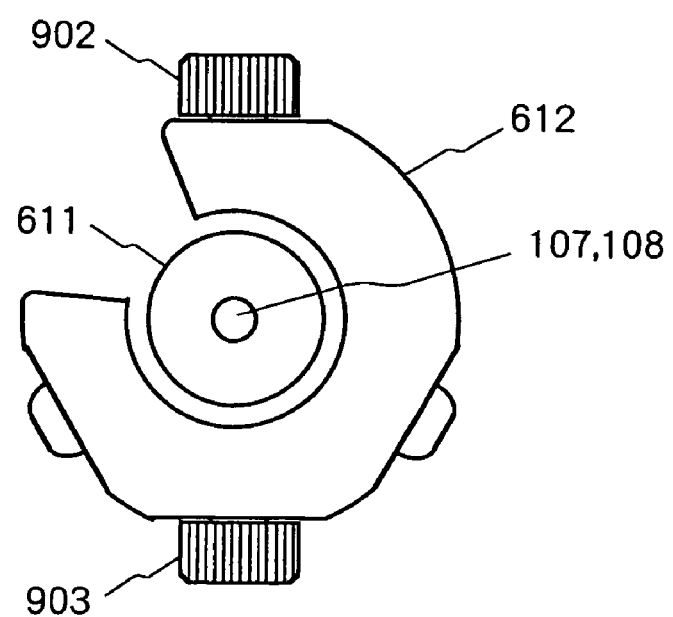

FIGS. 11(a) and 11(b) are views for explaining a schematic structure of the probe holder 612 and the probe casing 611 according to the embodiment 2, and, in particular, FIG. 11(a) is a vertical cross sectional side view of the probe holder 612 and the probe casing 611 according to the embodiment 2 and FIG. 11(b) is a front view of the probe holder 612 and the probe casing 611 according to the embodiment 2.

In FIG. 11(a), 901 shows a spring mechanism, 902 a first casing screw, and 903 a second casing cap screw.

As will be seen from FIG. 11(a), the probe casing 611 according to the embodiment 2 is formed in a cylindrical shape, and the diameter of the side face at one end thereof is formed to be reduced gradually toward the end thereof. Further, in the inner circumferential portions in the respective probe casings 611 a well know spring mechanism 901 is built-in and one end of the spring mechanism 901 is secured to the main body of the probe casing 611 and the other end thereof is secured to the movable portion catching the concerned optical fiber. In this instance, the movable portion of the spring mechanism catching the optical fiber acts to push out the top end portion of the optical fiber to the side where the diameter of the probe casing 611 gradually reduces, in that to the side causing the same to contact to the subject 214. Accordingly, like the embodiment 1, under the attachment state of the probe casing 611 into the probe holder 612 a force which pushes out the optical fibers toward the concave face side of the first and second shell plates 607 and 608 is always applied.

Further, in the probe casing 611 according to the embodiment 2 a groove is formed around the outer circumference thereof so that the top end portions of the first and second casing cap crews 902 and 903 disposed at the probe holder 612 can be inserted into the groove formed on the outer circumference thereof.

On one hand, in the probe holder 612 according to the embodiment 2 a cut-out is formed at a part of the cylinder shape thereof and the probe holder 612 is fixed to the first shell plate 607 so that the formed cut-out aligns with the cut-out formed in the first shell plate 607. Further, as mentioned above, for the probe holder 612 the first and second casing screws 902 and 903 are disposed at the position corresponding to the groove on the circumferential thereof. The length of the first and second casing cap screws 902 and 903 are formed in such a manner that the top end portions thereof project from the inner circumferential face of the probe holder 612 and are inserted into the groove formed around the outer circumferential face of the probe casing 611, thereby, the probe casing 611 is permitted to be held within the probe holder 612.

Further, in the embodiment 2, since the outer circumferential diameter of the probe casing 611 is constituted smaller than the inner circumferential diameter of the probe holder 612, the top end portion of the probe casing 611, in that the top end portion of the concerned optical fiber is movably supported in the direction perpendicular to a straight line formed by connecting the first and second casing cap screws 902 and 903 assuming the positions where the top end portions of the first and second casing cap screws 902 and 903 are inserted as a fulcrum. Accordingly, in the embodiment 2 after the first and second shell plates 607 and 608 have been attached to the subject, hair can be displaced toward the cut-outs formed in the shell plates 607 and 608, in addition thereto, after attaching the probe casing 611 in that the concerned optical fiber into the probe holder 612 disposed on the first and second shell plate 607 and 608, the probe casing 611 can be swung around the fulcrum. Namely, in the embodiment 2 the top end portion of the irradiation use and detection use optical fibers 107 and 108 are permitted to be swung in the direction perpendicular to the straight line formed by connecting the first and second casing cap screws 902 and 903. Accordingly, even in a case of a subject having plenty of hair in comparison with a newborn, the hair caught between the scalp and the optical fibers can be easily avoided. As a result, work efficiency for directly contacting the top end portions of the irradiation use and detection use optical fibers 107 and 108 at predetermined positions on the scalp of the subject can be enhanced. Accordingly, the diagnosis efficiency for a subject with the biological optical measurement instrument according to the embodiment 2 is enhanced.

Further, any direction of the cut-out with respect to the swinging direction of the probe casing 611 can be used, however, it is of cause most preferable to set the same at 90°.

Embodiment 3

Figure 12:
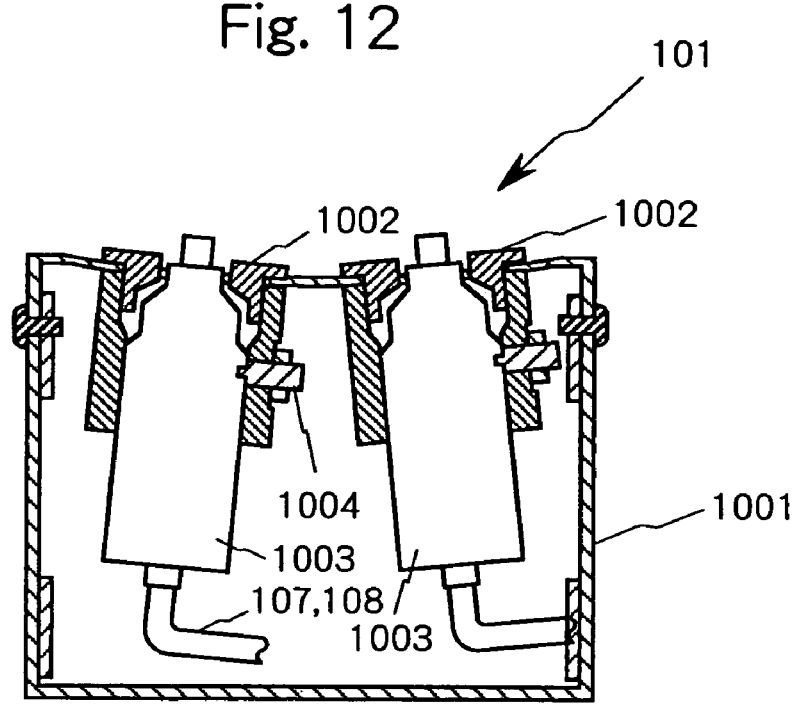
FIG. 12 is a vertical cross sectional side view for explaining a schematic constitution of a measurement probe in a biological optical measurement instrument representing embodiment 3 according to the present invention.
Figure 13:
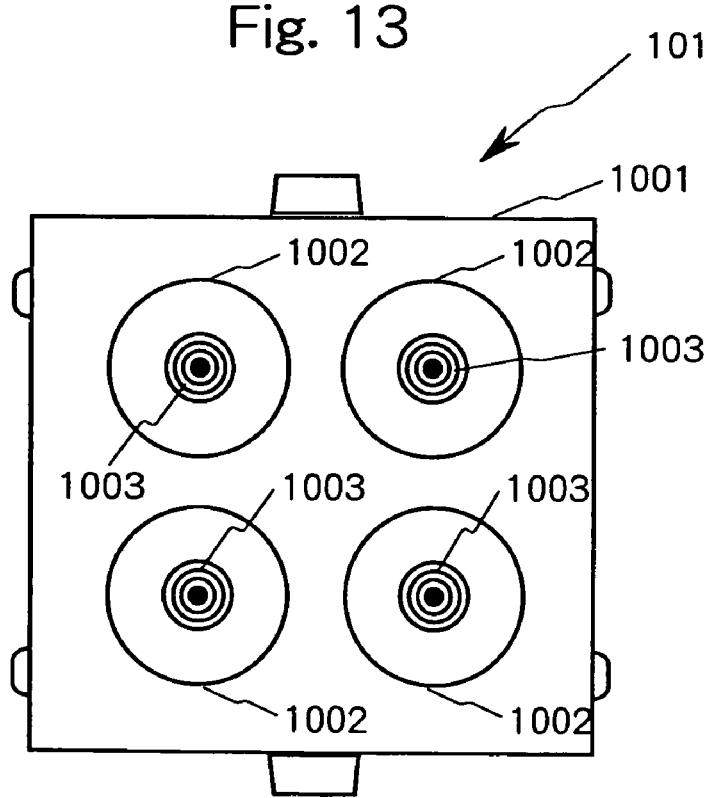
FIG. 13 is a top view for explaining a schematic constitution of a measurement probe in a biological optical measurement instrument representing embodiment 3 according to the present invention.

FIG. 12 is a vertical cross sectional side view for explaining a schematic constitution of a measurement probe 101 in a biological optical measurement instrument representing embodiment 3 according to the present invention; FIG. 13 is a top view for explaining a schematic constitution of a measurement probe 101 in a biological optical measurement instrument representing the embodiment 3 according to the present invention; and is a side view for explaining a schematic constitution of a measurement probe 101 in a biological optical measurement instrument representing the embodiment 3 according to the present invention. However, in the following explanation, only the part of the measurement probe 101 which is different from the biological optical measurement instrument according to the embodiment 1 will be explained. Further, in order to simplify the explanation, a case wherein respective 2 pieces of irradiation use optical fibers 107 and the detection use optical fiber 108 are included will be explained.

In FIGS. 12 through 14, 1001 shows a casing, 1002 a probe holder, 1003 a probe casing and 1004 a casing cap screw.

Figure 14:
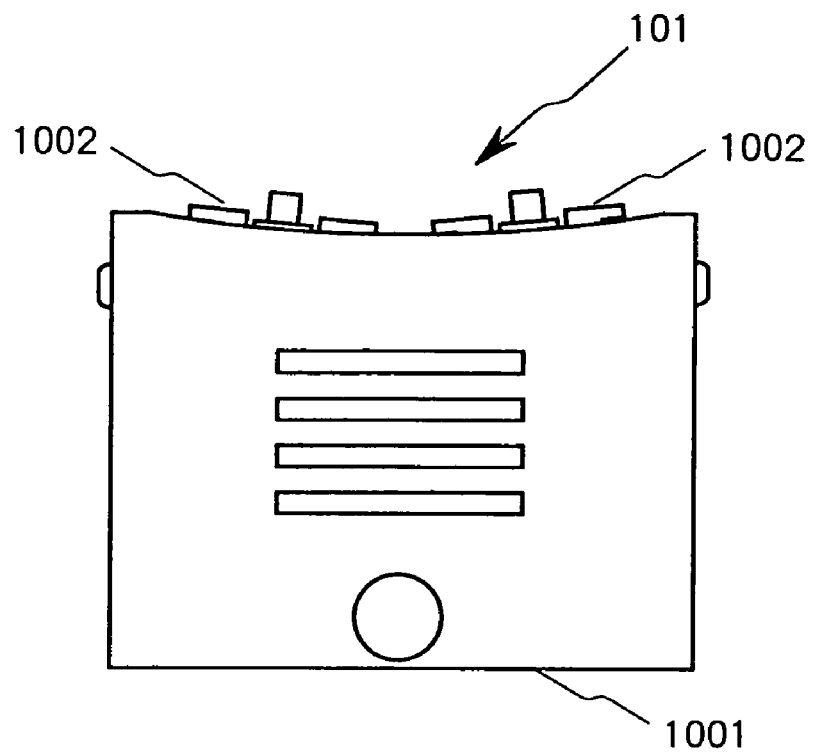
FIG. 14 is a side view for explaining a schematic constitution of a measurement probe in a biological optical measurement instrument representing embodiment 3 according to the present invention.

As will be seen from FIGS. 12 through 14, in the measurement probe 101 according to the embodiment 3, since the probe holder 1002 and the probe casing 1003 are accommodated in the casing 1001, the measurement probe 101 is constituted so that no unwanted force is applied to the probe casing 1003 and the irradiation use and detection use optical fibers 107 and 108, even when the measurement is performed for a not shown subject in lateral decubitus.

The upper face of the casing 1001 is formed in a concave shape like the shell plate 201 according to the embodiment 1 and on the upper face thereof the prove holder 1002 is disposed.

Figure 15:
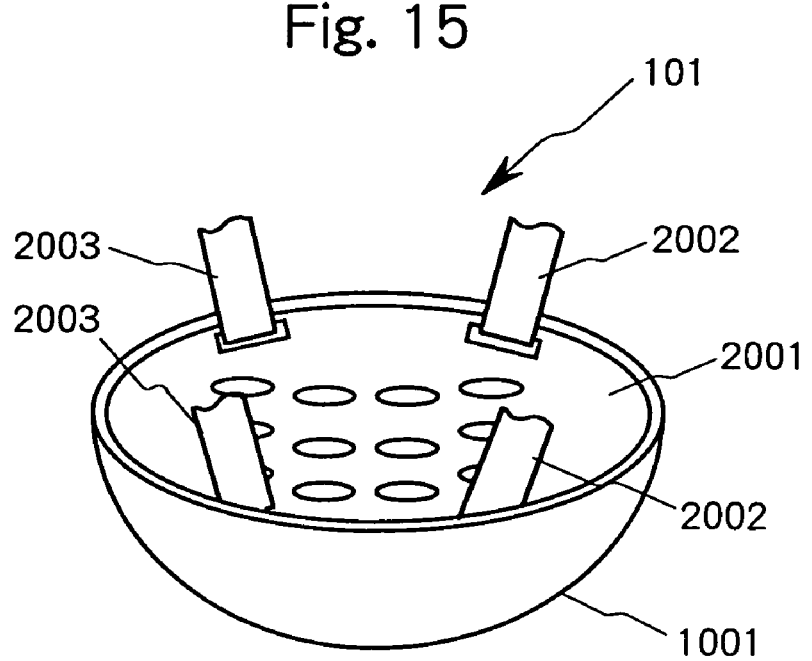
FIG. 15 is another view for explaining a schematic constitution of a measurement probe in a biological optical measurement instrument representing embodiment 3 according to the present invention.

Through projecting the top ends of the irradiation use and detection use optical fibers 107 and 108 from the upper face of the casing 1001, the measurement probe 101 supports the head portion of a not shown subject in lateral decubitus as well as the contacting portions between the scalp and the optical fibers 107 and 108 can be easily determined. Although, in the embodiment 3, the face opposing to the upper face of the casing 1001 where the probe holders 1002 are disposed is formed in a flat plane, but the configuration thereof is not limited to the above, and alternatively as shown in FIG. 15, when the face opposing to the upper face of the casing 1001 is formed in a curved shape or a semicylindrical shape, the main body of the casing 1001, in that the top end portions of the irradiation use and detection use optical fibers 107. and 108 can be moved in response to the movement of the head portion of the not shown subject, thereby, displacement of the detection positions due to movement of head portion of the subject can be prevented.

In this instance, when first and second subject fixing belts 2002 and 2003 for fixing the measurement probe 101 according to the embodiment 3 are provided at a portion of a shell plate 2001 serving as the upper face of the casing 1001, the follow-up property of the measurement probe 101 with respect to a subject 214 can be further enhanced, thereby, the performance of preventing detection position displacement due to movement of the head portion of the subject can be further enhanced. Further, when the portion of the shell plate 2001 is formed by a comparatively soft material, a sense of strangeness is greatly reduced when the measurement probe 101 is, in particular, used for the biological optical measurement for an infant. Still further, when the measurement probe 101 according to the embodiment 3 is used, the measurement probe 101 can easily follows up the movement around the body axis representing the major movement of the infant, thereby, the detection position displacement due to the movement of the head portion of the subject can be prevented.

Embodiment 4

Figure 16:
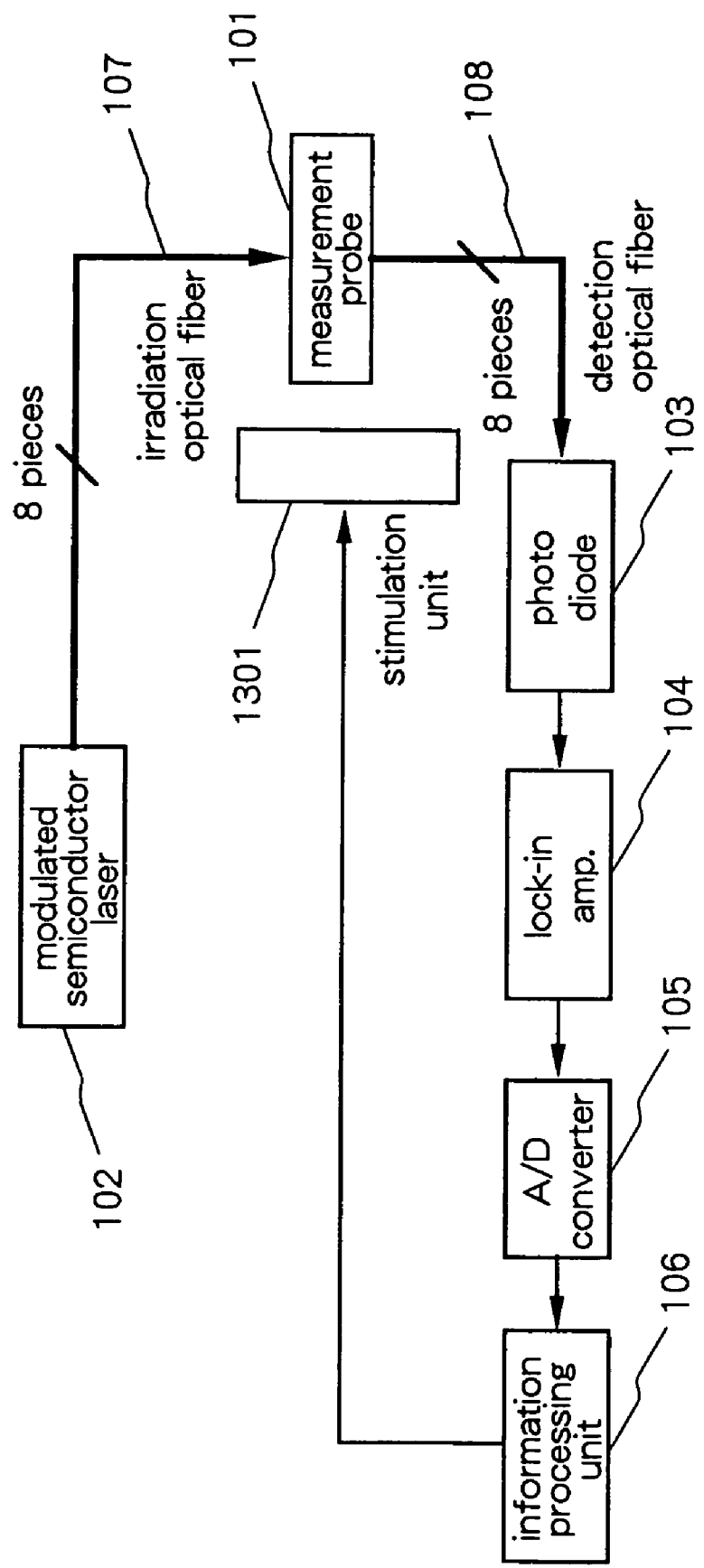
FIG. 16 is a diagram for explaining a schematic constitution of a biological optical measurement instrument representing embodiment 4 according to the present invention.

FIG. 16 is a diagram for explaining a schematic structure of a biological optical measurement instrument representing embodiment 4 according to the present invention, wherein 1301 shows a sense stimulation unit. However, in the following explanation, the structure and operation of the stimulation unit 1301 will be explained which is the only difference from the structure of the biological optical measurement instrument according to the embodiment 1.

The biological optical measurement instrument according to the embodiment 4 includes the sense stimulation unit 1301 which delivers a predetermined display output and audio output, for example, based on video signals and audio signals representing control signals from the information processing unit 106 according to the embodiment 1. Accordingly, since an activity condition of a brain can be measured while giving a video image stimulation and an audio stimulation to a subject, thereby, a further correct measurement can be achieved. Further, the video image stimulation and the audio stimulation given to the subject can be provided in synchronism with the measurement. In such instance, a measurement enhancing the measurement accuracy after giving the stimulation and until detecting the reaction thereof can be realized. Further, as the video image stimulation other than the general flashing stimulation, displays of a variety of picture images can be used.

Figure 17:
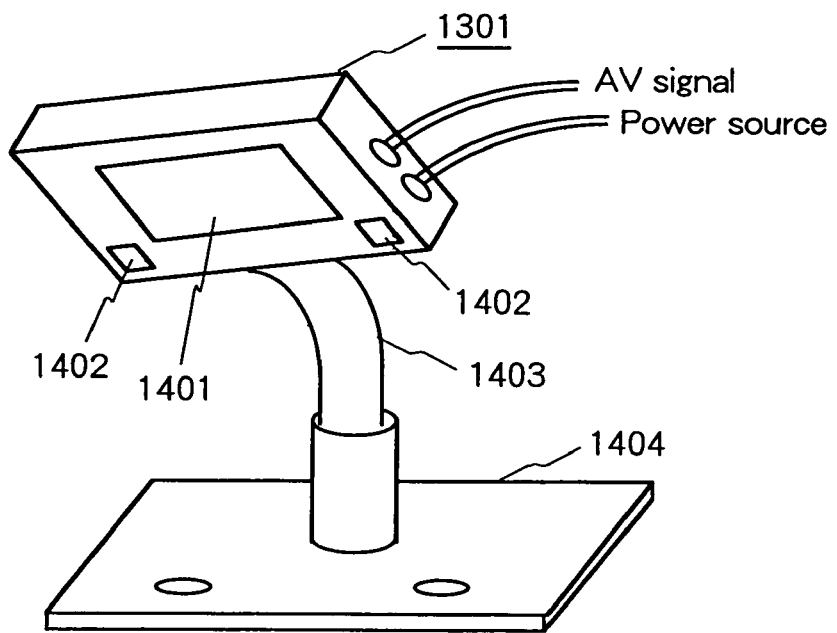
FIG. 17 is a view for explaining a schematic constitution of a stimulation unit in a biological optical measurement instrument representing embodiment 4 according to the present invention.

FIG. 17 is a view for explaining a schematic structure of the sense stimulation unit in the biological optical measurement instrument according to the embodiment 4, wherein 1401 shows a display portion, 1402 a speaker, 1403 a flexible tube and 1404 a stand.

Figure 18:
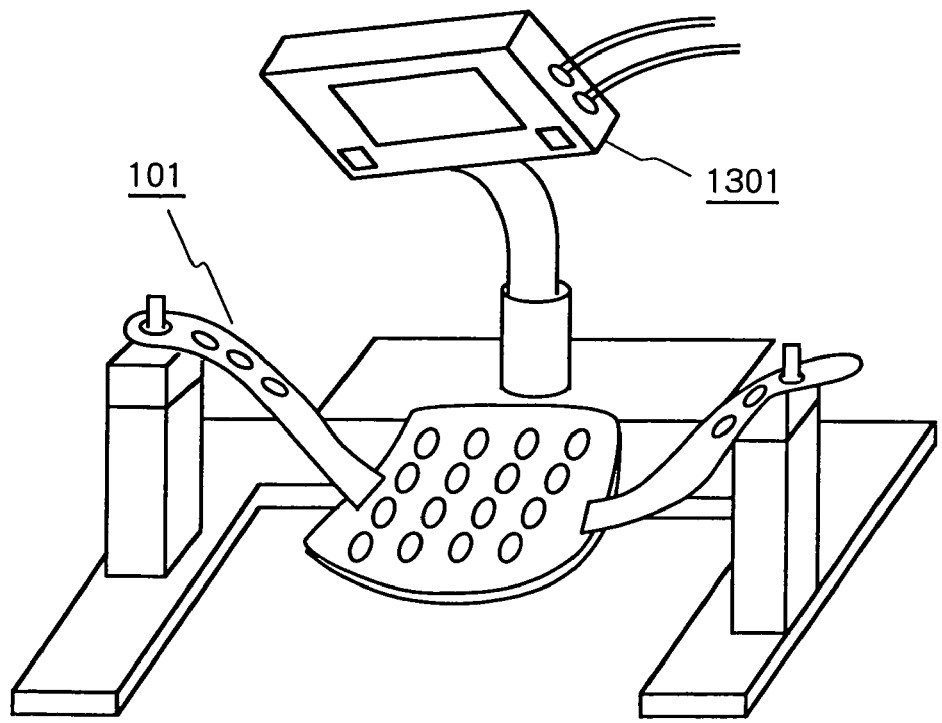
FIG. 18 is a view for explaining a manner when using the stimulation unit in combination with the embodiments 1 and 2 according to the present invention.

The display portion 1401 is, for example, constituted by a well known liquid crystal display unit and at the bottom side of the liquid crystal unit the well know speaker 1402 which outputs audio sound is disposed. The display portion 1401, is attached to the stand 1404 via the flexible tube 1403. Accordingly, for example, as shown in FIG. 18, when used together with the measurement probe 101 according to the embodiment 1 or 2, it is possible to easily give a sense stimulation to the head portion of the subject, therefore, such measurement can be performed, for example, for a newborn to which such measurement was conventionally impossible.

In the sense stimulation unit 1301 according to the embodiment 4, since the display portion 1401 and the stand 1404 are connected via the flexible tube 1403, such as position and angle of the display unit 1401 with respect to the not shown subject can be easily modified. Accordingly, even when performing measurement for a variety of sizes of the head portions of the subjects and for a variety of measurement postures, the display portion 1401 can be properly set with respect to the subject.

In such instance, as has been explained above, the sense stimulation given to the newborn and the brain activity caused by the sense stimulation can be measured in synchronism, the diagnosis efficiency can be enhanced.

Further, in the embodiment 4, only the illuminative stimulation and sound stimulation are given, however, the stimulation is not limited thereto. For example, if a plurality kind of flavors are prepared in advance which serve as bases of smells and any of the flavors are mixed and delivered from the front face of the display portion 1401 based on the command from the information processing unit 106, a measurement synchronous with the smell stimulation can be performed. Further, if a plurality kind of solutions are prepared in advance which serve as bases of tastes and any of the solutions are mixed and are fed to the subject via such as a tube provided at the front face of the display portion 1401, a measurement synchronous with the taste stimulation can also be performed.

Further, in the embodiment 4, for the display unit 1401 serving as a illuminative stimulation generating means a liquid crystal display unit is used, however, the display unit is not limited thereto, for example, such as a well known light bulb, a strobe device, a projector device and a back light device used for a liquid crystal device can, of course, be used. In particular, in case when performing a measurement for a subject such as an infant, since it is difficult to draw attention of the infant to the display portion 1401, a light bulb, a strobe device and a projector device are suitable which can emit light having comparatively high capacity.

Further, although the stand 1404 is disposed at the flexible tube 1403 in the embodiment 4, the present invention is not limited to such structure, for example, if a well known clump is disposed at an end of the flexible tube 1403, the clump can be easily attached such as to a bed where a subject is laid and to a handrail disposed for the bed, thereby, an advantage that the display portion 1401 can be disposed at the most proper position is obtained.

Embodiment 5

Figure 19:
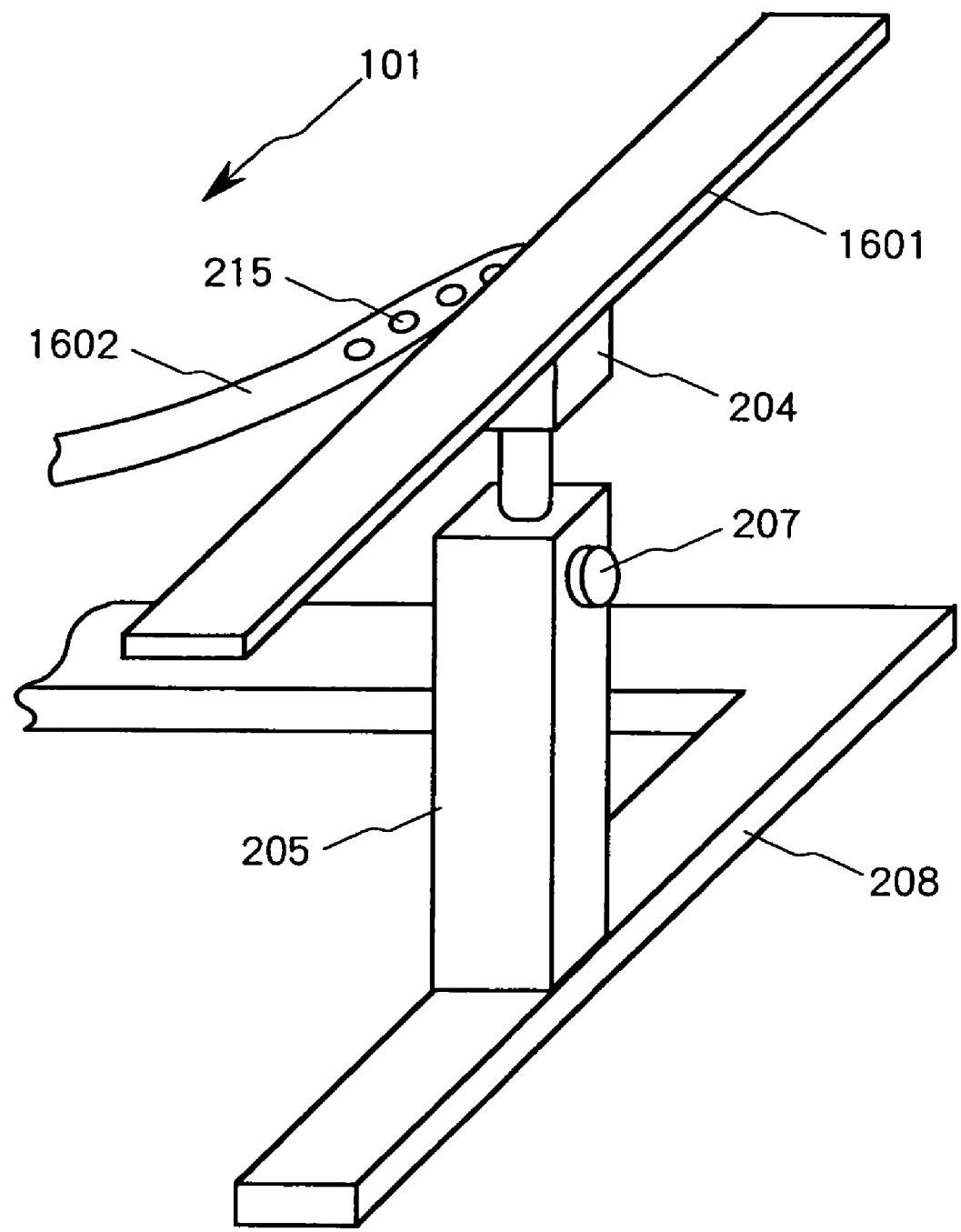
FIG. 19 is a view for explaining a schematic constitution of a measurement probe in a biological optical measurement instrument representing embodiment 5 according to the present invention.

FIG. 19 is a view for explaining a schematic structure of a part of a measurement probe 101 in a biological optical measurement instrument representing the embodiment 5 according to the present invention, wherein 1601 shows a guide rail and 1602 a belt. However, in the following explanation, only the structure of the adjustable support column 204 will be explained which is different from that in the measurement probe 101 according to the embodiment 1.

As shown in FIG. 19, in the measurement probe 101 according to the embodiment 5, a guide rail 1601 which is formed in parallel with the pillow base 208 is disposed at the other end of the adjustable support column 204. Further, the guide rail 1601 is formed so that the extending direction thereof is in parallel with the body axis of the subject 214, when the measurement probe 101 according to the embodiment S is set for the not shown subject 214. More specifically, among the pillow base 208 formed in a U shape the guide rails 1601 are formed on the two side planes where the support columns 205 are formed.

On the guide rail 1601 a not shown belt hook portion which is movable in the extending direction thereof is formed, and the belt hook portion is hooked to one of the holes 215 formed at the belt 1602. Like the embodiment 1, at one end of the belt 1602 the not shown shell plate 201 is disposed and at the other end thereof a plurality of holes 215 are formed. Accordingly, also in the measurement probe 101 according to the embodiment S through supporting the other end of the belt 1602 the shell plate 201 is designed to be supported so as to permit rocking in back and forth and right and left, in that in the body axis direction of a subject and in the direction perpendicular to the body axis. In particular, in the measurement probe 101 according to the embodiment 5, since the belts 1602 which hang the shell plate 201 supporting the head portion of the subject 214 at the both sides thereof are supported so as to permit movement in the body axis, a possible displacement of contact positions between the optical fibers and the scalp in association with the movement of the subject in the back and forth direction can be, in particular, prevented.

Embodiment 6

Figure 20:
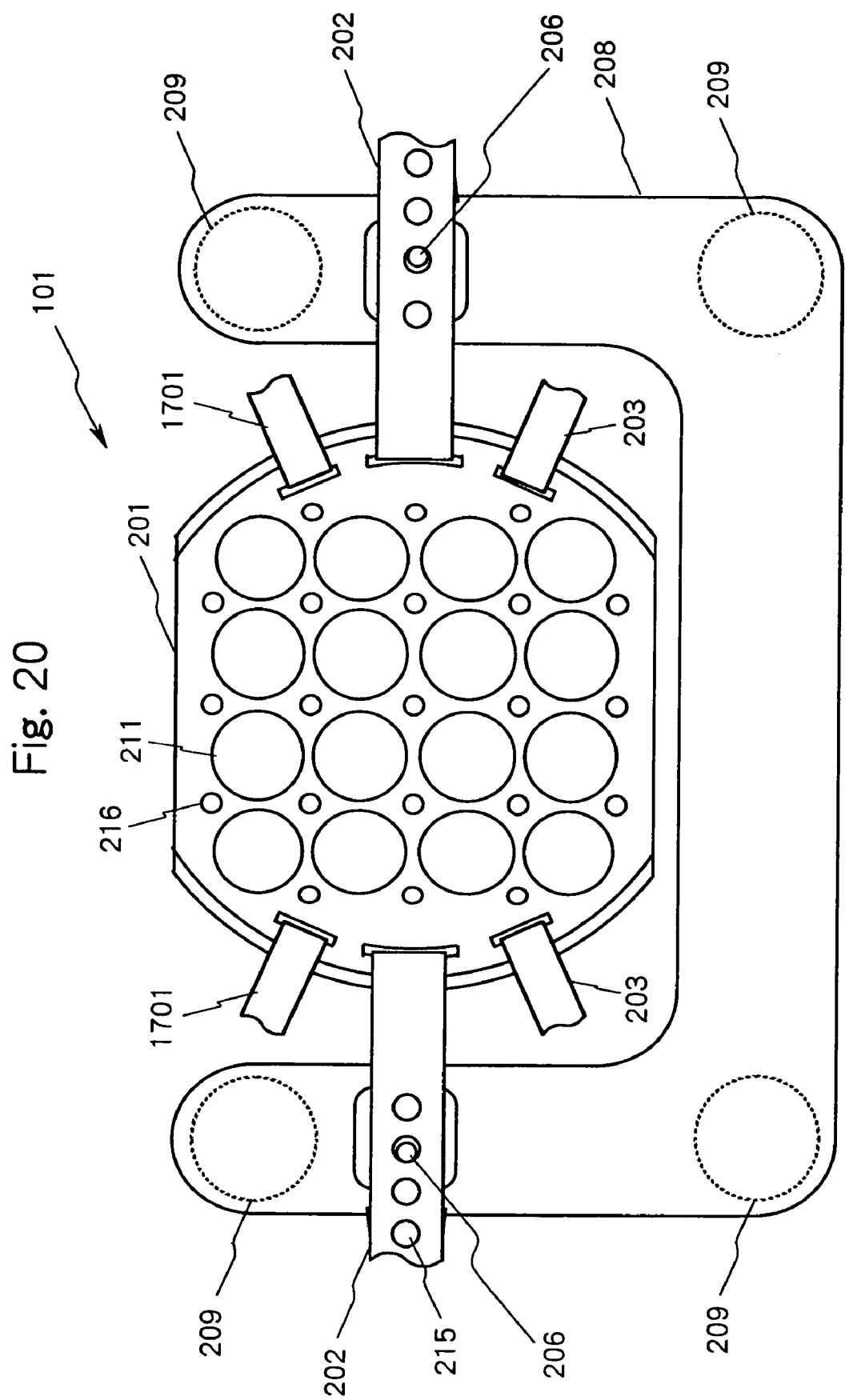
FIG. 20 is a view for explaining a schematic constitution of a measurement probe in a biological optical measurement instrument representing embodiment 6 according to the present invention.

FIG. 20 is a view for explaining a schematic structure of a measurement probe 101 in a biological optical measurement instrument representing the embodiment 6 according to the present invention, wherein 1701 shows a second subject fixing belt. However, in the following explanation, only the structure of the second subject fixing belt 1701 will be explained which is different from that of the measurement probe 101 in the embodiment 1.

As shown in FIG. 20, like the subject fixing belt 203 according to the embodiment 1, in the measurement probe 101 according to the embodiment 6, the second subject fixing belt 1701 formed by a resin series material having comparatively small elasticity.

In particular, in the embodiment 6, at one side with respect to holes disposed at the both ends of the shell plate 201 and for passing the belt 202 therethrough holes for passing the subject fixing belt 203 are formed and at the other side with respect thereto holes for passing the second subject fixing belt 1701 are formed. Accordingly, by means of the measurement probe 101 according to the embodiment 6, for example, when the subject fixing belts 203 are passed at the side of the forehead of the subject 214 and the second subject fixing belts 1701 are passed at the jaw of the subject 214, the shell plate 201 is fixed to the subject 214 at two portions.

As a result, a possible displacement of the contact positions between the optical fibers and the scalp due to displacement of the shell plate 201 in association with a rocking of the subject 214 can be prevented.

Embodiment 7

Figure 21:
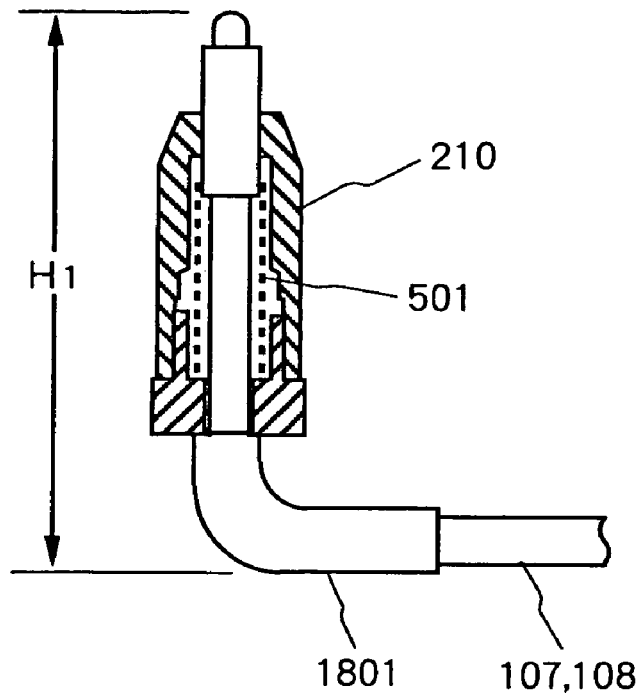
FIGS. 21(a) and 21(b) are views for explaining a schematic constitution of a probe casing used for a measurement probe in a biological optical measurement instrument representing embodiment 7 according to the present embodiment.
Figure 21:
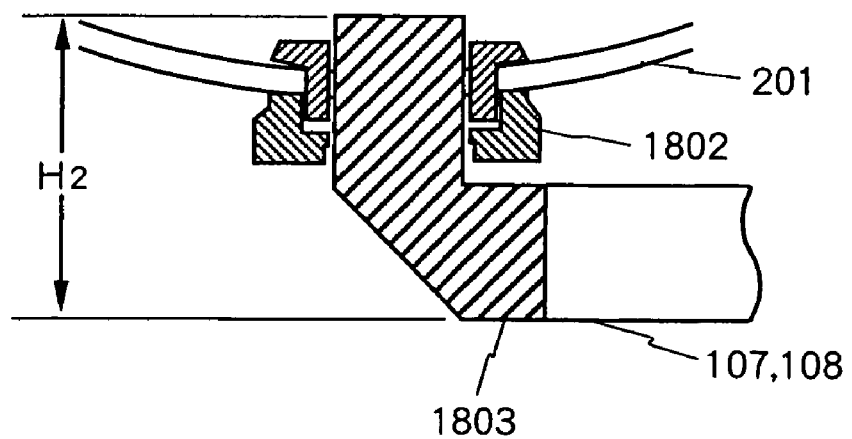

FIGS. 21(a) and 21(b) are views for explaining a schematic structure of a measurement probe 101 in a biological optical measurement instrument representing the embodiment 7 according to the present invention, in particular, FIG. 21(a) is a view for explaining a schematic structure of a variation of the probe casing 210 according to the embodiment 1 and FIG. 21(b) is a view for explaining a schematic structure of the probe casing and the probe holder according to the embodiment 7. However, in the following explanation, only the structure of the probe casing and the probe holder will be explained which is different from that in the measurement probe 101 according to the embodiment 1.

As will be seen from FIG. 21(a), in the variation of the probe casing 210 according to the embodiment 1, at the leading out position of the irradiation use or detection use optical fibers 107 and 108, for example, a SUS pipe 1801 formed by a stainless steel is disposed. The SUS pipe 1801 is, for example, bent by 90° and is designed to pass the irradiation use or detection use optical fiber 107 and 108 therethrough. Since the optical fibers 107 and 108 are designed to be covered by the SUS pipe 1801, with the variation of the probe casing 210 according to the embodiment 1, when the measurement probe 101 is disposed at the occiput of the not shown subject, a possible damaging of the irradiation use and detection use optical fibers 107 and 108 due to an extreme distortion thereof is prevented.

On the other hand, in the embodiment 7 as shown in FIG. 21(b), at the top end portion of irradiation use or detection use optical fiber 107 and 108 a well known prism 1803 is disposed. The prism 1803 is constituted in such a manner that an angle formed between one light incident and emitting face and the other thereof forms 90° and the end portion of the irradiation use or detection use optical fiber 107, and 108 is disposed at the other light incident and emitting face. The one light incident and emitting face of the prism 1803 is disposed so as to contact to the surface of the subject 214. Namely, the side of the one light incident and emitting face of the prism 1803 is held by the probe holder 1802 according to the embodiment 7. Accordingly, the height H2 of the probe casing according to the embodiment 7 can be reduced lower than the height H1 of the probe casing according to the embodiment 1 and the variation thereof. As a result, with the measurement probe 101 according to the embodiment 7, the height of the measurement probe 101 can be lowered during the measurement, a load incurred to the subject 214 can be reduced, when the measurement probe 101 is set at the occiput of the subject 214.

Further, the angle formed by the one light incident and emitting face with respect to the other of the prism 1803 is not limited to be 90°, but any angle can be, of course, used.

Embodiment 8

Figure 22:
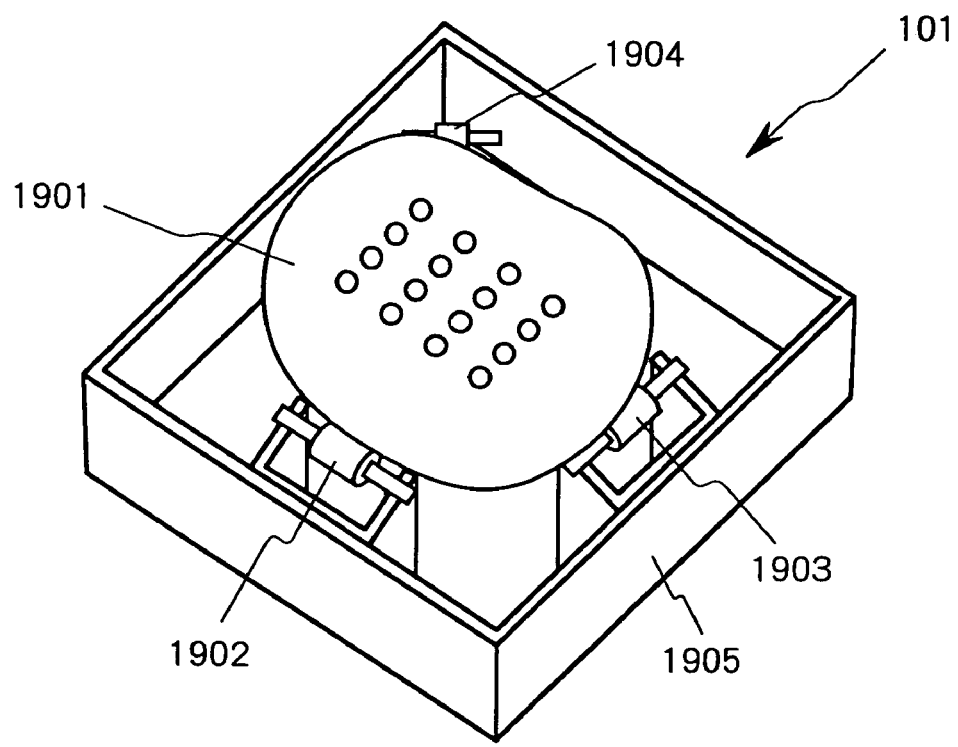
FIGS. 22(a) and 22(b) are views for explaining a schematic constitution of a measurement probe in a biological optical measurement instrument representing embodiment 8 according to the present invention.
Figure 22:
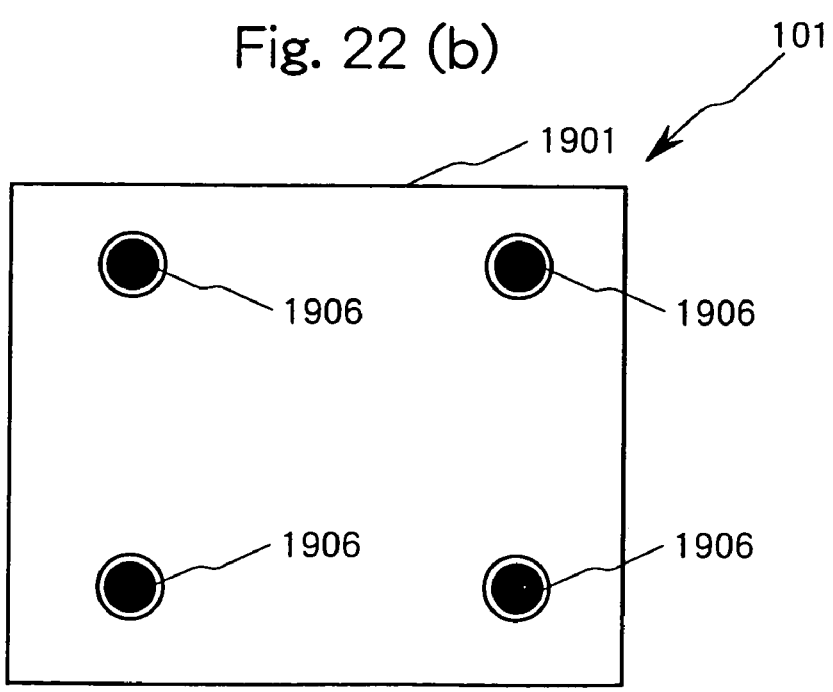

FIGS. 22(a) and 22(b) are views for explaining a schematic structure of a measurement probe 101 in a biological optical measurement instrument representing the embodiment 8 according to the present invention, in particular, FIG. 22(a) is a perspective view of the measurement probe 101 according to the embodiment 8 and FIG. 22(b) is a back side view of the measurement probe 101 according to the embodiment 8. However, in the following explanation, only the structure of the measurement probe 101 will be explained which is different from that in the biological optical measurement instrument according to the embodiment 1.

In FIGS. 22(a) and 22(b), 1901 shows a shell plate, 1902 a first roller, 1903 a second roller, 1904 a third roller, 1905 a casing and 1906 ball type tires.

As will be seen from FIG. 22(a), in the measurement probe 101 according to the embodiment 8, among the side faces of the casing 1901 the first roller 1902 and the second roller 1903 are respectively disposed at adjacent two sides thereof. Further, the third roller 1904 is disposed at a facing corner of two sides where the first and second rollers 1901 and 1902 are not disposed.

In the embodiment 8, through placing the shell plate 1901 on the first through third rollers 1902-1904, the shell plate 1901 is supported by the three rollers of the first through third rollers 1902-1904. As a result, with the measurement probe 101 according to the embodiment 8, since a movable freedom of the shell plate 1901 with respect to the casing 1905 can be increased, a performance can be enhanced which prevents displacement of contact positions between the optical fibers and the scalp caused by displacement of the shell plate 1901 in association with rocking of the subject 214.

Further, in the measurement probe 101 according to the embodiment 8, since four well known ball type tires 1906 are respectively arranged at the back face of the casing 1905, in a case where the not shown subject 214 is positioned in lateral decubitus and the measurement probe 101 according to the embodiment 8 is set at the occiput, the measurement probe 101 can perform follow-up displacement even when the subject 214 displaces in parallel with the plane where the subject is placed. As a result, a performance can be enhanced which prevents displacement of contact positions between the optical fibers and the scalp caused by a displacement of the shell plate 1901 in association with rocking of the subject 214.

Further, in the measurement probe 101 according to the embodiment 8, the position of the shell plate 1901 with respect to the casing 1905 is designed to be movable as well as the main body of the casing 1905 itself is designed movable, however, the present invention is not limited to such structure, for example, while eliminating the ball type tires 1906 and the shell plate 1901 can be, of course, modified movable only with respect to the casing. Further, as in the previously explained embodiment 3, it is, of course, possible to design to dispose the ball type tires at the back face of the casing 1905, while fixing the shell plate 1901 to the casing 1905.

Further, through a provision of a well known vertical movement mechanism in order to vertically move the first through third rollers 1902-1904, an angle of the shell plate 1901 with respect to a measurement position can be varied. Further, when displacing the first through third rollers 1902-1904 in a same degree, the height of the shell plate 1901 can be adjusted in response to the height of the neck of the subject which varies depending on individual difference. Still further, through a provision of a subject fixing belt at both ends of the shell plate 1901 for fixing the subject 214 to the shell plate 1901, a performance can be enhanced which prevents displacement of contact positions between the optical fibers and the scalp caused by a displacement of the shell plate 1901 in association with rocking of the subject 214.

Embodiment 9

Figure 23:
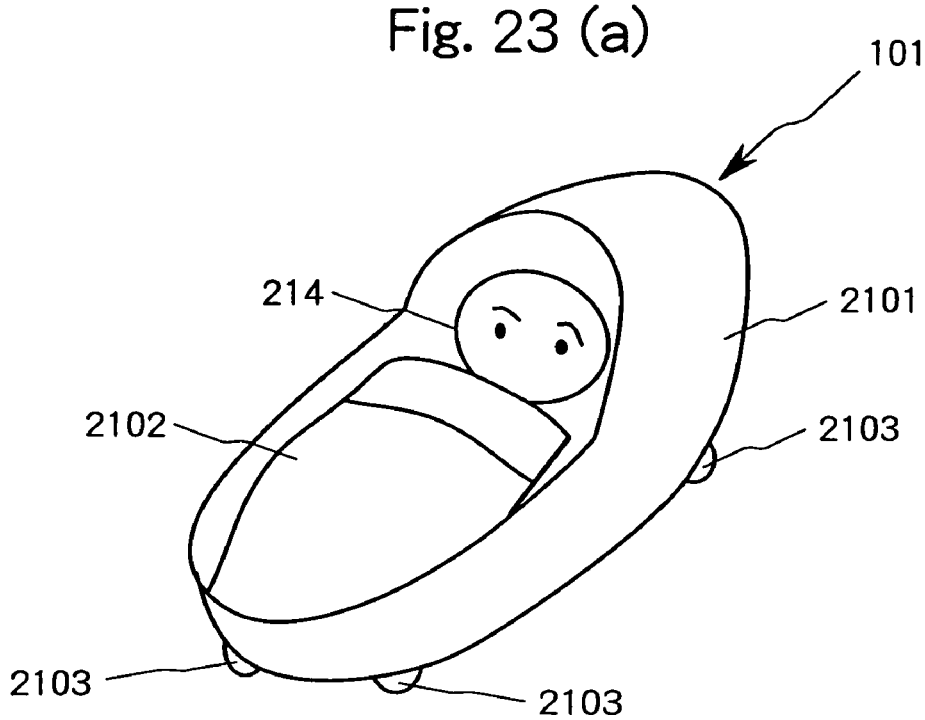
FIGS. 23(a) and 23(b) are views for explaining a schematic constitution of a measurement probe in a biological optical measurement instrument representing embodiment 9 according to the present invention.
Figure 23:
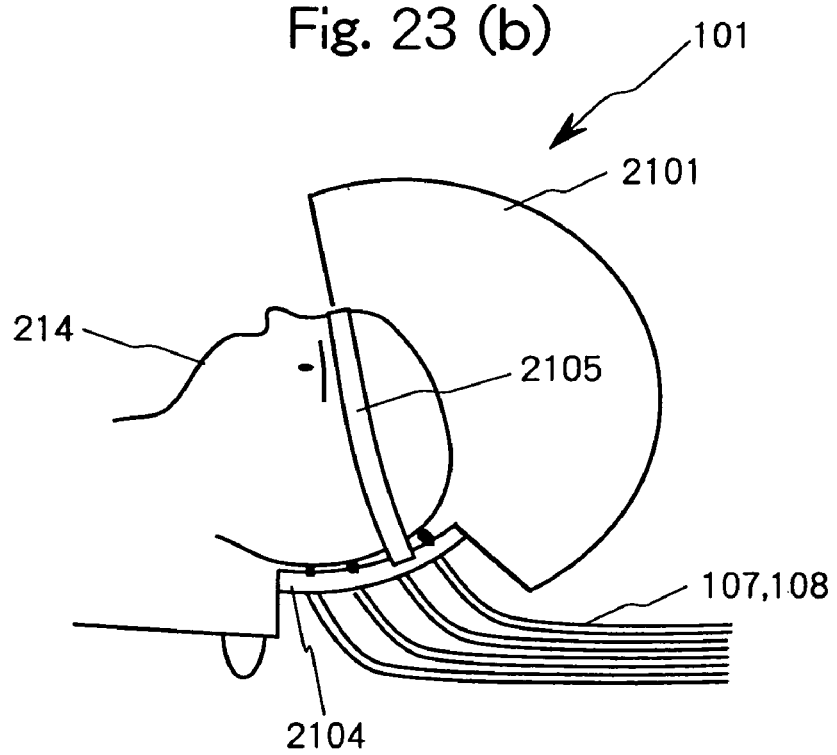

FIGS. 23(a) and 23(b) are views for explaining a schematic structure of a measurement probe 101 in a biological optical measurement instrument representing the embodiment 9 according to the present invention, in particular, FIG. 23(a) is a perspective view of the measurement probe 101 according to the embodiment 9 and FIG. 23(b) is a view for explaining a detailed structure of a part of a shell plate 2104 in the measurement probe 101 according to the embodiment 9. However, in the following explanation, only the structure of the measurement probe 101 will be explained which is different from that in the biological optical measurement instrument according to the embodiment 1.

In FIGS. 23(a) and 23(b), 2101 shows a casing, 2102 a quilt, 2103 casing legs, and 2104 a shell plate.

As will be seen from FIG. 23(a), in the measurement probe 101 according to the embodiment 9, the casing 2101 is formed in a shape of a baby bed. Further, in the measurement probe 101 according to the embodiment 9, in order to limit the movement of the subject 214 placed in the casing 2101, the quilt 2102 for covering the subject 214 is provided. In this embodiment, for example, when providing means for fixing the quilt 2102 to the casing 2101, the subject 214 can be fixed to the casing 2101.

Further, since four casing legs 2103 are disposed at the back face of the casing 2101, an easy turn-over of the casing is prevented, even if the subject moves.

Now, a detailed structure of the measurement probe 101 according to the embodiment 9 will be explained with reference to FIG. 23(b).

In the measurement probe 101 according to the embodiment 9, under the condition when the subject is laid on its back, the shell plate 2104 is disposed at the position corresponding to the occiput. To the shell plate 2104 the subject fixing belt 2105 for fixing the head portion of the subject 214 is disposed and, like the measurement probe 101 according to the embodiment 1, the subject fixing belt 2105 is designed to apply the fore head of the subject 214. Further, the probe holders, for example, as, shown in the embodiment 1 are disposed to the shell plate 2104 and respective probe casings are designed to be attached to the probe holders.

In the measurement probe 101 according to the embodiment 9, by forming the casing 2101 in a shape of a baby bed, the movement of the subject is restricted as well as after disposing the shell plate 2104 at a position corresponding to the occiput or other measurement position, the shell plate 2104 can be fixed to the head portion of the subject by the subject fixing belt 2105, thereby, a possible displacement of the contact positions between the optical fibers and the scalp can be prevented.

Embodiment 10

Figure 24:
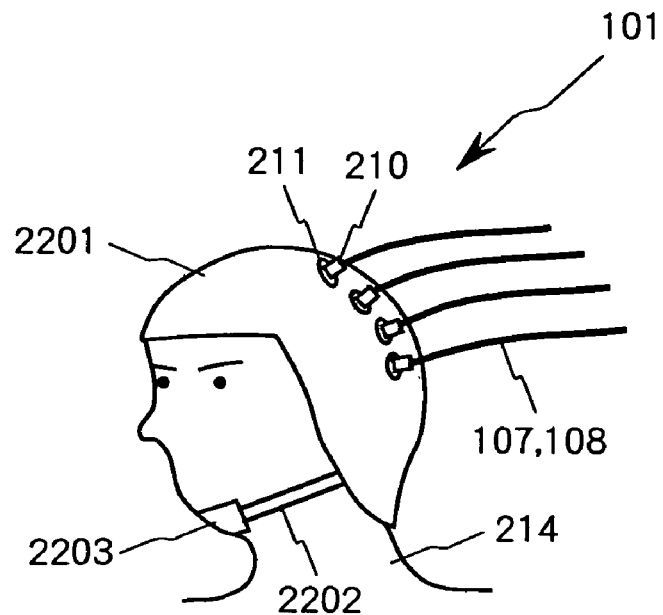
FIGS. 24(a) and 24(b) are views for explaining a schematic constitution of a measurement probe in a biological optical measurement instrument representing embodiment 10 according to the present invention.
Figure 24:
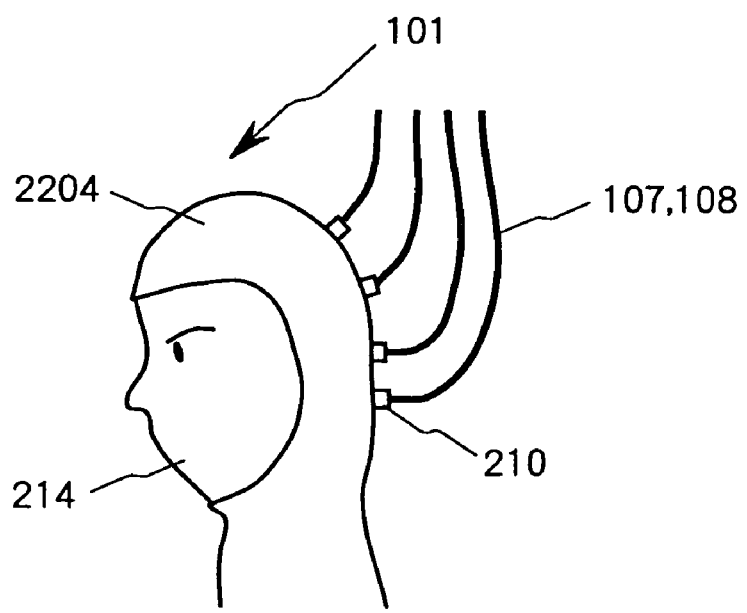

FIGS. 24(a) and 24(b) are views for explaining a schematic structure of a measurement probe 101 in a biological optical measurement instrument representing the embodiment 10 according to the present invention, in particular, FIG. 24(a) is a view for explaining a schematic structure of the measurement probe 101 for only covering the head portion of a subject and FIG. 24(b) is a view for explaining a schematic structure of the measurement probe 101 for covering the upper half body of the subject. However, in the following explanation, only the structure of the measurement probe 101 will be explained which is different from that in the biological optical, measurement instrument according to the embodiment 1.

In FIG. 24(a), 2201 shows a shell plate, 2202 a subject fixing belt, and 2203 a jaw use plate.

As will be seen from FIG. 24(a), in the measurement probe 101 according to the embodiment 10, the shell plate 2201 is formed in a cap shape, and as the material therefor, for example, cloth or rubber is used. To this shell plate 2201, like the shell plate according to the embodiment 1, probe holders 211 are disposed and through attachment of the probe casing 210 to the respective probe holders 211 the top end portions of the irradiation use and detection use optical fibers 107 and 108 are designed to be contacted to the epiderm (skin surface) of the subject 214. Further, in the measurement probe 101 according to the embodiment 10, since the shell plate 2201 is formed so as to cover the hair portion of the subject 214, a restriction performance of the lower portion of the shell plate 2201, in that the portion thereof disposed at a position near the neck of the subject 214 is enhanced, and further, in order to prevent displacement of contact positions between the optical fibers and the epiderm the subject fixing belt 2202 is disposed at the lower portion of the shell plate 2201. However, since it is necessary to apply the subject fixing belt 2202 to the jaw portion of the subject 214, the subject fixing belt 2202 is required to prevent a possible displacement as well as required to reduce uncomfortable feeling would be caused to the subject 214. For this purpose, in the measurement probe 101 according to the embodiment 10, the jaw use plate 2203 is disposed at an intermediate portion of subject fixing belt 2202 where the jaw of the subject 214 touches.

On the other hand, as shown in FIG. 24(b), when the shell plate 2204 is formed like a suit of which the subject 214 can wear, since a possible positional displacement between portion forming the shell plate 2204 where the probe holders 211 are disposed and the subject 214 can be prevented, a possible displacement of the contact positions between the optical fibers and the scalp can be prevented.

Further, in case when forming the shell plates 2201 and 2204 by a cloth, by making use of a stretchable cloth a contacting property of the irradiation use and detection use optical fibers 107 and 108 onto the surface of the subject, in that a performance of preventing contact position displacement between the optical fibers and the epiderm can be enhanced.

Further, in a case when the measurement probe 101 is formed in a suit shape as shown in FIG. 24(b), when an opening and closing portion is provided while disposing there such as a zipper, the attachment and detachment of the measurement probe 101 is facilitated.

Embodiment 11

Figure 25:
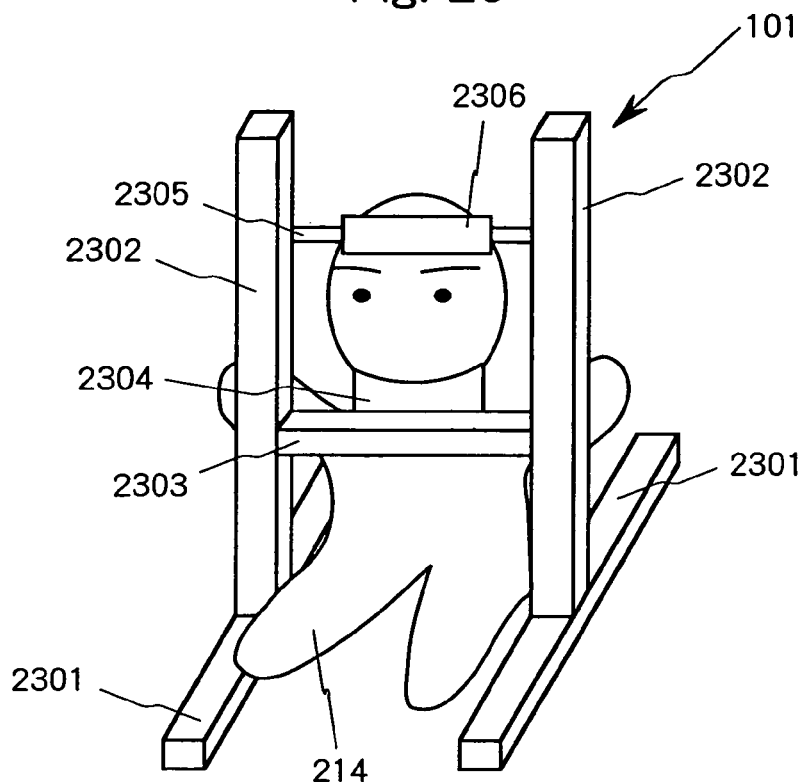
FIG. 25 is a view for explaining a schematic constitution of a measurement probe in a biological optical measurement instrument representing embodiment 11 according to the present invention.

FIG. 25 is a view for explaining a schematic structure of a measurement probe 101 in a biological optical measurement instrument representing the embodiment ii according to the present invention, wherein 2301 shows a pillow base, 2302 side support columns, 2303 a horizontal support column, 2304 a jaw keeper, 2305 a horizontal belt and 2306 a shell plate. However, in the following explanation, only the structure of the measurement probe 101 will be explained which is different from that in the biological optical measurement instrument according to the embodiment 1.

As will be seen from FIG. 25, the measurement probe 101 according to the embodiment 11 is constituted by a restriction member which restricts the subject at a predetermined position and an optical fiber fixing member which fixes the top end portions of the not shown irradiation use and detection use optical fibers 107 and 108 at a measurement portion of the subject 214 being restricted by the restriction member.

As will be seen from FIG. 25, the restriction member according to the embodiment 11 is formed by combining respectively the two pillow bases 2301 and the two side support columns 2302 in T shape, and by coupling the side support columns 2302 with the horizontal support column 2303 while facing the same each other. In this instance, in the restriction member according to the embodiment 11 the jaw keeper 2304 for fixing the jaw of the subject 214 is disposed at the horizontal support column 2303, thereby, the position of the head portion is designed to the fixed when the subject 214 is restricted. Further, in the restriction member according to the embodiment 11, a not shown restriction use belt for restricting the subject 214 to the restriction member is disposed. Still further, in the restriction member in the measurement probe 101 according to the embodiment 11, the horizontal belt 2305 is bridged between the two side support columns 232 and the shell plate 2306 is attached to the horizontal belt 2305. Further, since the structure of the shell plate 2306 is constituted like the shell plate according to the embodiment 1, the detailed explanation thereof is omitted.

In particular, in the restriction member in the measurement probe 101 according to the embodiment 11, through the provision of the two restriction belts, in that the head portion restriction belt restricting the head portion of the subject 214 and the trunk restriction belt restricting the body portion of the subject to the horizontal, support column, the restriction performance can be enhanced.

Further, when a cushion material is disposed on the respective surfaces of the pillow base 2301, the side support columns 2302 and the horizontal support column 2303 which constitute the restriction member according to the embodiment 11, a sense of strangeness can be reduced, when the subject is restricted to the restriction member.

Embodiment 12

Figure 26:
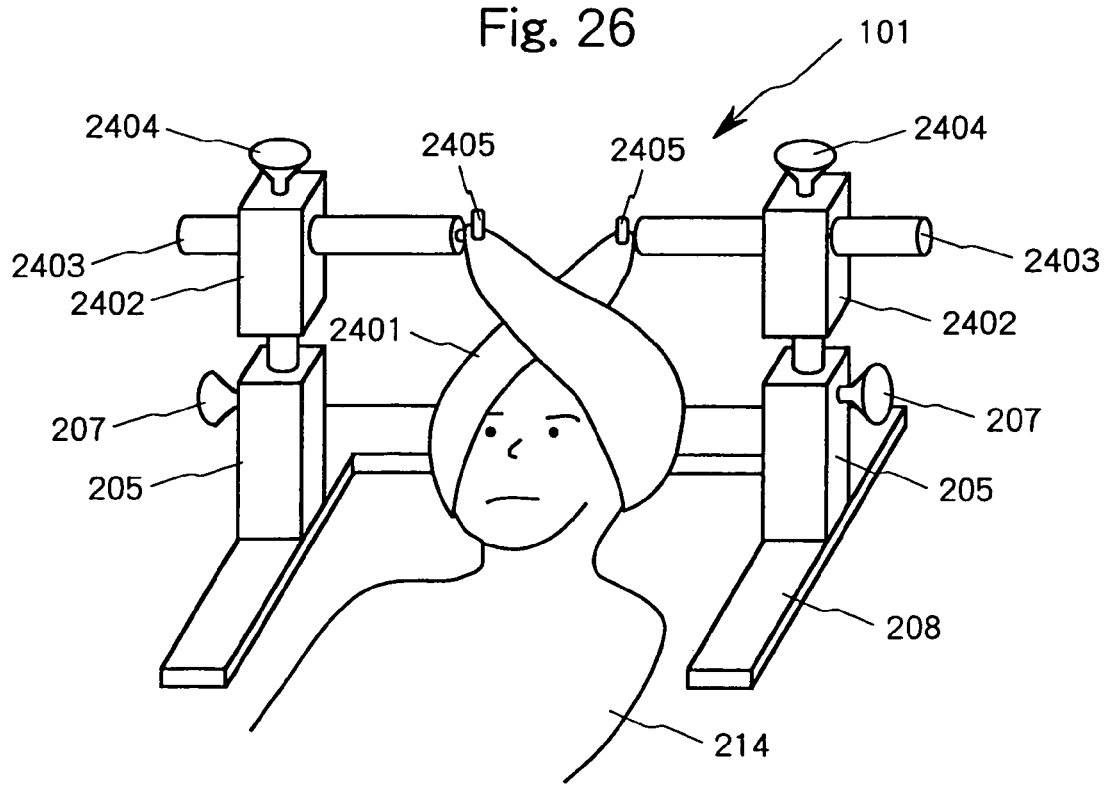
FIG. 26 is a view for explaining a schematic constitution of a measurement probe in a biological optical measurement instrument representing embodiment 12 according to the present invention.

FIG. 26 is a view for explaining a schematic structure of a measurement probe 101 in a biological optical measurement instrument representing the embodiment 12 according to the present invention, wherein 2401 shows a shell plate, 2402 adjustable support columns, 2403 horizontal support columns, 2404 horizontal adjustment screws and 2405 hook pins.

However, in the following explanation, only the structure of the measurement probe 101 will be explained which is different from that in the biological optical measurement instrument according to the embodiment 1.

As will be seen from FIG. 26, the measurement probe 101 according to the embodiment 12, like the measurement probe 101 according to the embodiment 1, is constituted by a shell plate 2401 serving as an optical fiber fixing member and a supporting member which supports in a hanging manner the shell plate 2401 and the head portion of the subject 214 supported by the shell plate 2401.

The shell plate 2401 according to the embodiment 12 is constituted by a cloth having a flexibility and a predetermined strength, for example, such a cloth formed from a polyester and a vinyl leather. At the both ends of the shell plate 2401 respectively one piece of hole is formed and through fitting the hook pins 2405 attached at the respective ends of the horizontal support column 2403 to these holes the shell plate 2401 is supported in a hanging manner. Further, the details of the shell plate 2401 according to the embodiment 12 will be explained later.

The supporting member according to the embodiment 12, like the supporting member according to the embodiment 1, at the upper faces of the opposing two sides of the pillow base 208 formed in a U shape the support columns 205 extending upward are respectively attached. In each of the support column 205 a cylindrical hole is formed along the extending direction thereof and an adjustment screw 207 is disposed which is directed from the side face of the support column 205 to the center thereof.

Now, the portion which is different from that in the embodiment 1 will be explained with reference to FIG. 26.

One end of the adjustment support column 2402 according to the embodiment 12 is formed in a circular column so as to permit insertion thereof into the hole provided in the support column 205. On the other hand, at the other end of the adjustment support column 2402 a circular column shaped hole is formed in the direction perpendicular to the extending direction thereof and the horizontal adjustment screw 2404 directing the center of the circular column shaped hole is disposed from the upper portion of the adjustable support column 2402. Into the hole formed in the adjustable support column 2402 the horizontal support column 2403 is passed so as to permit movement thereof in the center axis direction, in that the extending direction of the horizontal support column 2403. However, in the measurement probe 101 according to the embodiment 12 the movement of the horizontal support column 2403 is limited by fastening the horizontal adjustment screw 2404, namely, the interval between the opposingly disposed horizontal support columns 2403 is designed to be set as desired.

Thus, in the measurement probe 101 according to the embodiment 12, since by making use of the cloth having a width capable of covering the head portion of the subject 214 for the shell plate 2401, the both ends of the shell plate 2401 are supported in a hanging manner by the supporting member, even if the subject moves, a possible displacement of the contact positions between the optical fibers and the scalp can be prevented.

Figure 27:
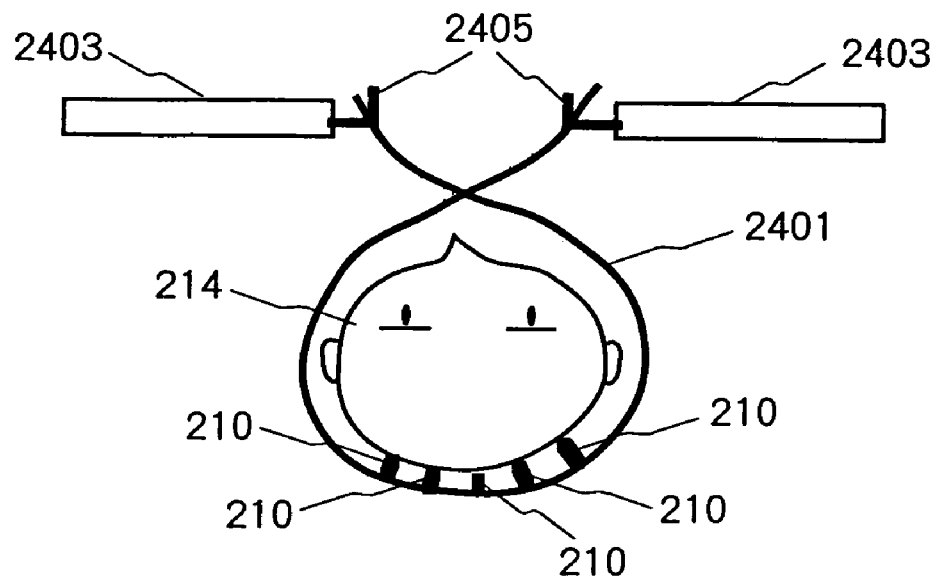
FIGS. 27(a) and 27(b) are views for explaining a detailed constitution of a shell plate in the embodiment 12 according to the present invention.
Figure 27:
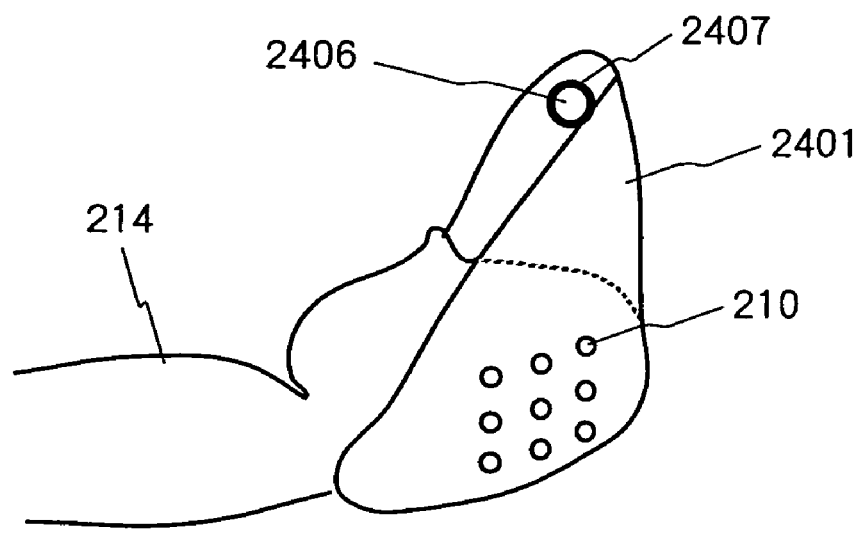
Figure 28:
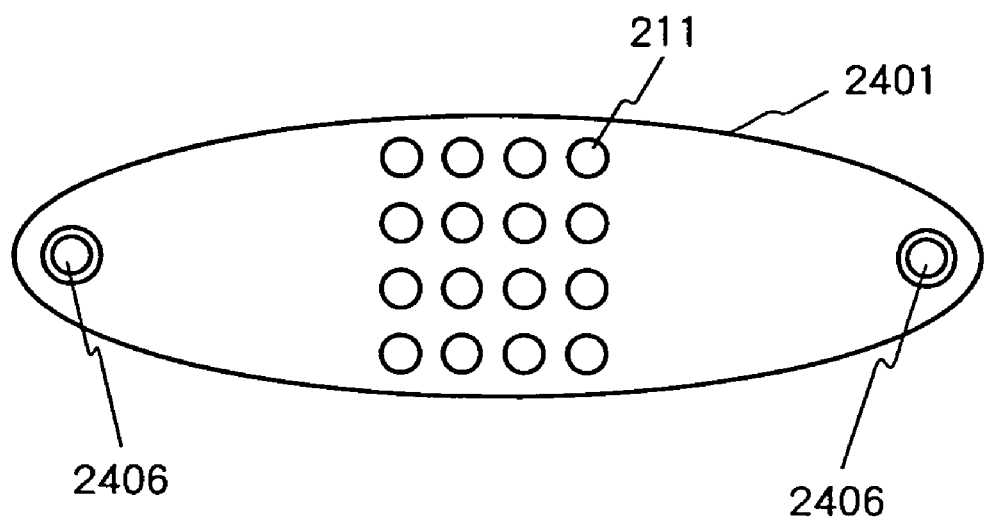
FIGS. 28(a) and 28(b) are views for explaining a relationship between biological optical measurement position and a probe holder position in the embodiment 12 according to the present invention.
Figure 28:
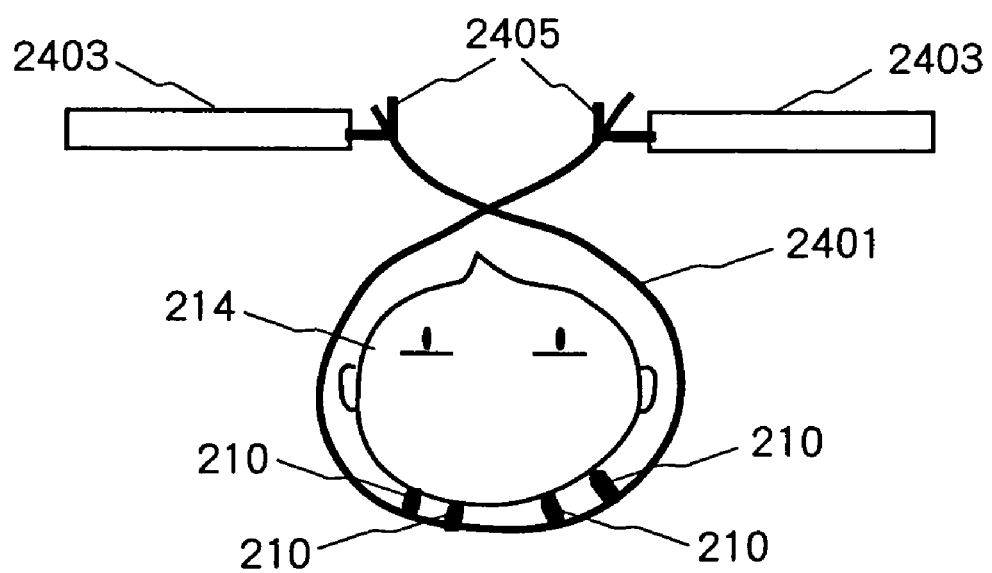
Figure 29:
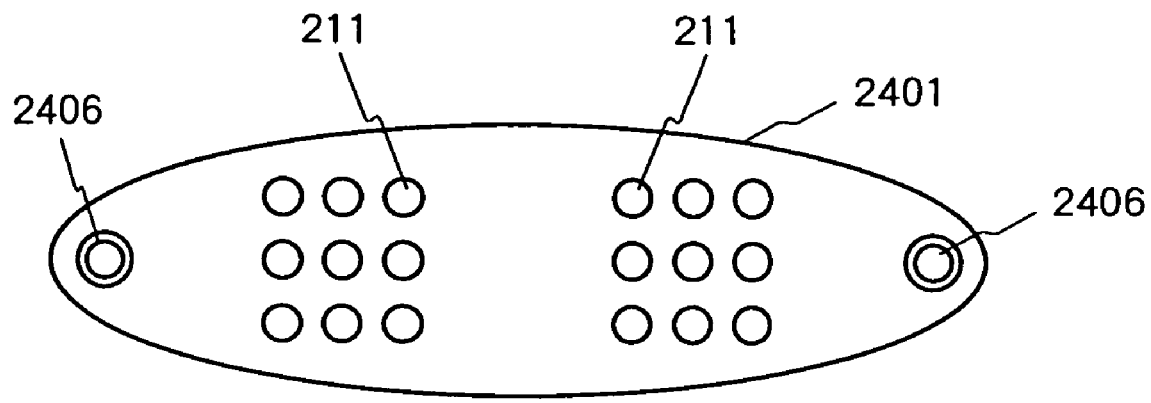
FIGS. 29(a) and 29(b) are views for explaining a relationship between biological optical measurement position and another probe holder position in the embodiment 12 according to the present invention.
Figure 29:
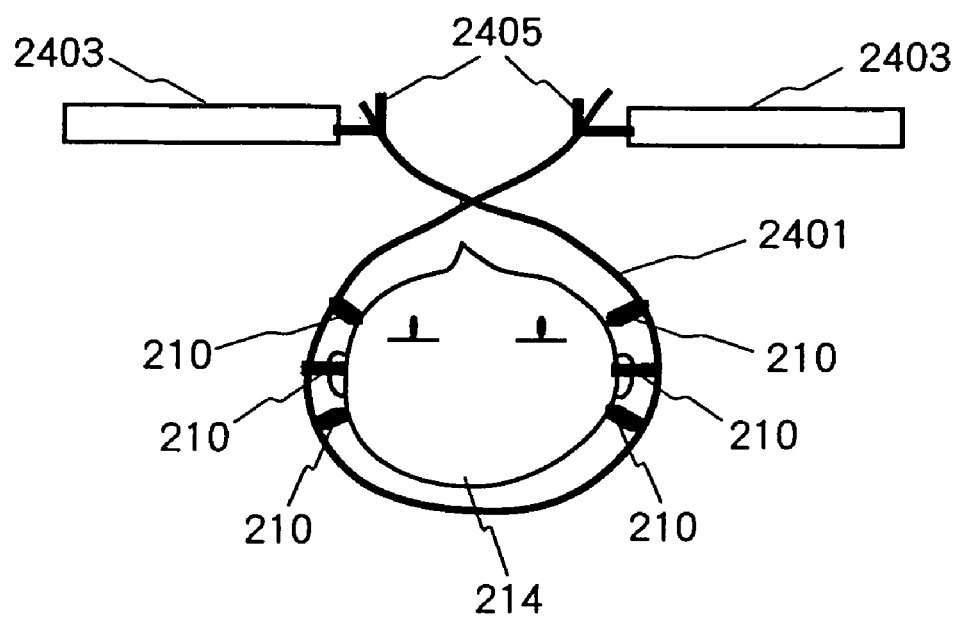
Figure 30:
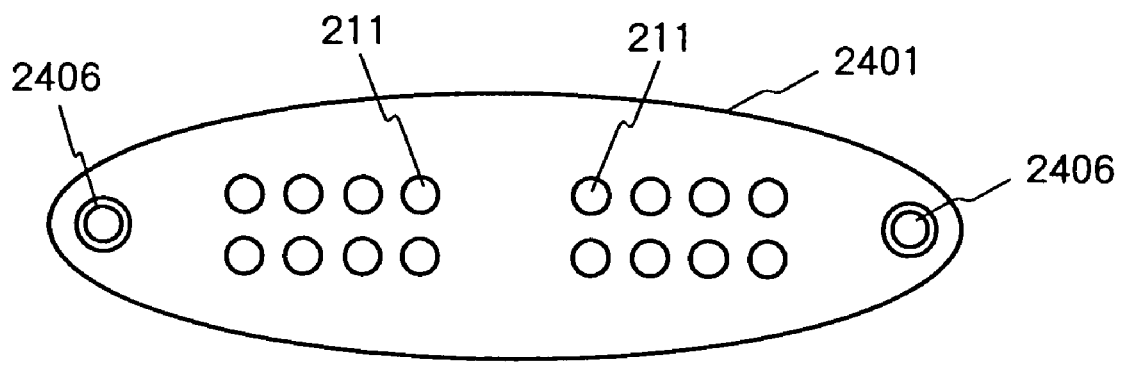
FIGS. 30(a) and 30(b) are views for explaining a relationship between biological optical measurement position and still another probe holder position in the embodiment 12 according to the present invention.
Figure 30:
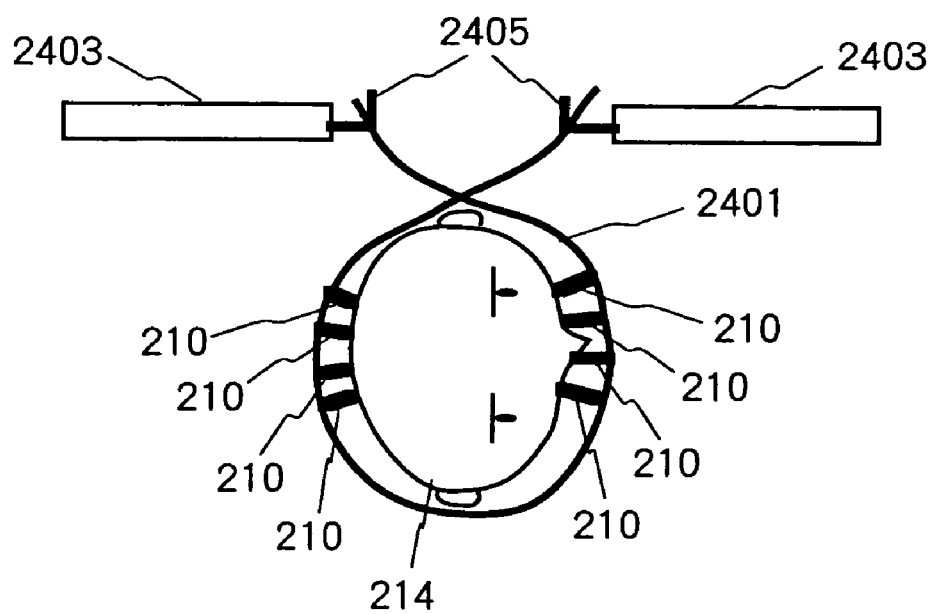
Figure 31:
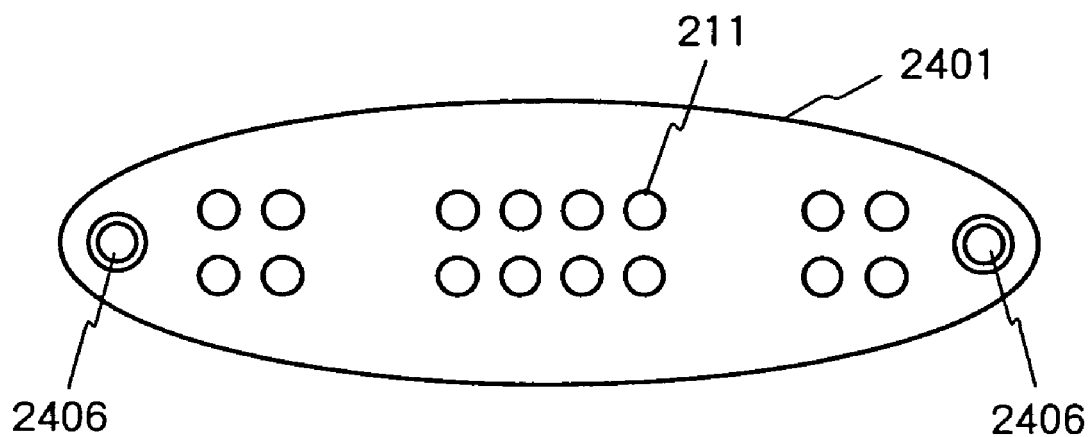
FIGS. 31(a) and 31(b) are views for explaining a relationship between biological optical measurement position and a further probe holder position in the embodiment 12 according to the present invention.
Figure 31:
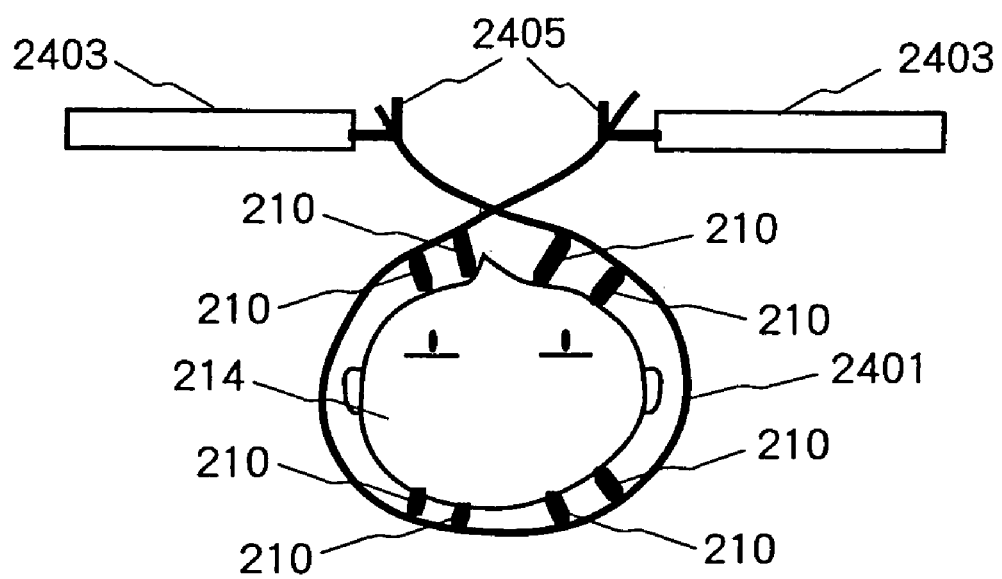

FIGS. 27(*a*) and 27(*b*) are views for explaining a detailed structure of the shell plate 2401 according to the embodiment 12, in particular, FIG. 27(*a*) is a front view for explaining the detailed structure of the shell plate 2401 and FIG. 27(*b*) is a side view for explaining the detailed structure of the shell plate 2401.

As shown in FIG. 27(*a*), the shell plate 2401 according to the measurement 12 is formed so as to wrap the head portion of the subject 214. At the center portion of the shell plate 2401 not shown probe sockets (holder) are disposed and when performing a measurement under a condition where the subject 214 is laid on its back, it is designed so that the top end portions of the probe casings 210, in that the top end portions of the irradiation use and detection use optical fibers 107 and 108 contact to the occiput of the subject 214.

Further, as shown in FIG. 27(*b*), at the both end portions of the shell plate 2401 holes 2406 are provided which permit fitting to the hook pins 2405 attached to the respective one ends of the horizontal support columns 2403 and in order to increase the strength of the holes 2406 a well known enforcement 2407 is provided for the respective holes 2406.

FIGS. 28(a) through 31(b) are views for explaining a relationship between the position of biological optical measurement and the position of the probe holders, in particular, FIGS. 28(a), 29(a), 30(a) and 31(a) are views for explaining the positions of the probe holders formed at the shell plate 2401, and FIGS. 28(b), 29(b), 30(b) and 31(b) are views for explaining a relationship of the position of biological optical measurement and the posture of the subject.

As shown in FIG. 28(a), through disposing 4×4 pieces of probe holders 211 at the center portion of the shell plate 2401, a shell plate 2401 which is suitable for a biological optical measurement of the occiput of the subject 214 can be constituted. When performing a biological optical measurement by making use of the shell plate 2401 as shown in FIG. 28(a), by supporting in a hanging manner the head portion of the subject 214 upwardly as shown in FIG. 28(b), the top end portions of the probe casings 210 disposed at the respective probe holders 211, in that the top end portions of the not shown irradiation use and detection use optical fibers 107 and 108 can be contacted to the occiput of the subject 214.

As shown in FIG. 29(a), through disposing 3×3 pieces of probe holders 211 at the right and left portions of the shell plate 2401, a shell plate 2401 which is suitable for simultaneous measurement of right and left temples of the subject 214 can be constituted. When performing a biological optical measurement by making use of the shell plate 2401 as shown in FIG. 29(a), by supporting in a hanging manner the head portion of the subject 214 upwardly as shown in FIG. 29(b), the top end portions of the probe casings 210 disposed at the respective probe holders 211, in that the top end portions of the not shown irradiation use and detection use optical fibers 107 and 108 can be contacted to the right and left temples of the subject 214 at the same time.

As shown in FIG. 30(a), through disposing 2×4 pieces of probe holders 211 at the right and left portions of the shell plate 2401, a shell plate 2401 which is suitable for simultaneous measurement of the sinciput and the occiput of the subject 214 can be constituted. When performing a biological optical measurement by making use of the shell plate 2401 as shown in FIG. 30(a), by supporting in a hanging manner the head portion of the subject 214 sideways as shown in FIG. 30(b), the top end portions of the probe casings 210 disposed at the respective probe holders 211, in that the top end portions of the not shown irradiation use and detection use optical fibers 107 and 108 can be contacted to the sinciput and occiput of the subject 214 at the same time.

As shown in FIG. 31(a), through disposing 2×2 pieces of probe holders 211 at the right and left portions of the shell plate 2401 as well as 2×4 pieces of probe holders 211 at the center of the shell plate 2401, a shell plate 2401 which is suitable for simultaneous measurement of sinciput and the occiput of the subject 214 can be constituted. When performing a biological optical measurement by making use of the shell plate 2401 as shown in FIG. 31(a), by supporting in a hanging manner the head portion of the subject 214 upwardly as shown in FIG. 31(b), the top end portions of the probe casings 210 disposed at the respective probe holders 211, in that the top end portions of the not shown irradiation use and detection use optical fibers 107 and 108 can be contacted to the sinciput and occiput of the subject 214 at the same time. However, when using the shell plate 2401 as shown in FIG. 31(a), even if the head portion of the subject 214 is supported in a hanging manner downwardly, the top end portions of the probe casings 210 disposed at the respective probe holders 211, in that the top end portions of the not shown irradiation use and detection use optical fibers 107 and 108 can be contacted to the sinciput and occiput of the subject 214 at the same time.

Thus, by means of the measurement probe 101 according to the embodiment 12, through modifying the arrangement patterns and arrangement positions of the probe holders 211, the measurement portions can be easily varied. Accordingly, if a plurality kind of shell plates 211 of which arrangement patterns and arrangement positions of the probe holders 211 are varied are prepared in advance, and a proper shell plate 2401 is selected depending on the measurement portion and the size of the head portion of the subject 214, a variety of biological optical measurement which meets a variety of postures and the measurement positions can be performed.

Figure 32:
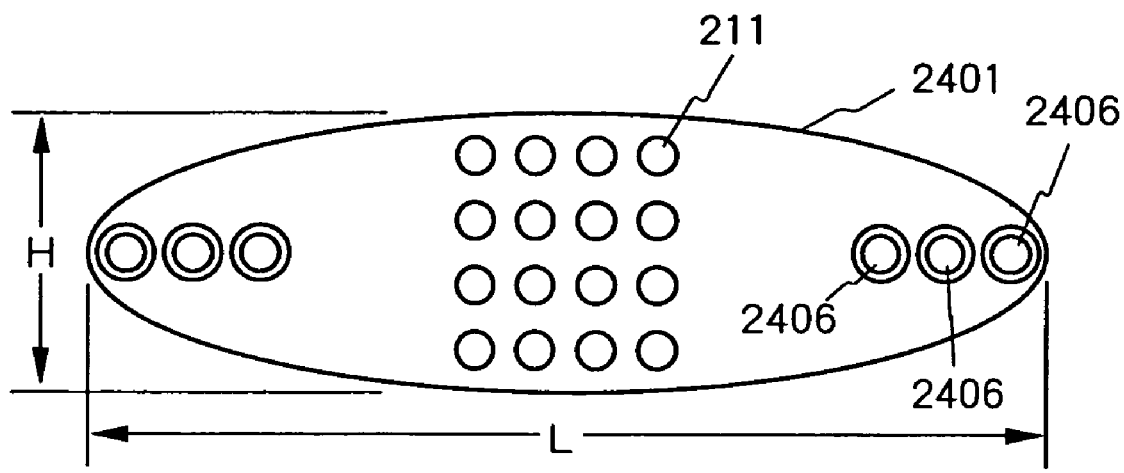
FIGS. 32(a) and 32(b) are views for explaining constitution examples of other shell plate used in other measurement probes in the embodiment 12 according to the present invention.
Figure 32:
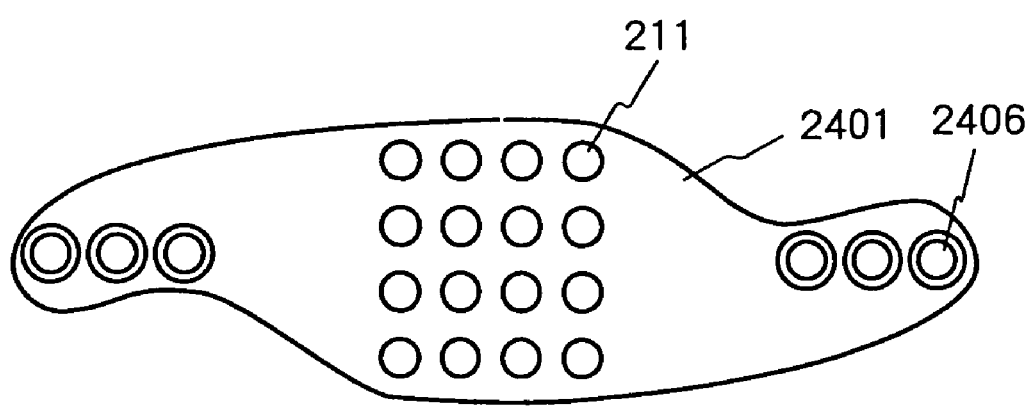

FIGS. 32(a) and 32(b) are views for explaining other structural examples of a measurement probe 101 according to embodiment 12, in particular, FIG. 32(a) is a view for explaining a schematic structure of another shell plate 2401 according to the embodiment 12 and FIG. 32(b) is a view for explaining a schematic structure of still another shell plate 2401 according to the embodiment 12.

Like the measurement probe 101 according to the embodiment 1, the measurement probe 101 making use of the shell plate 2401 according to the embodiment 12 as shown in FIG. 32(a) is provided with a plurality of holes 2406 in the extending direction of the shell plate 2401 so that freedom and hanging height of the shell plate 2401 when supporting in a hanging manner the head portion can be adjusted.

The shell plate 2401 as shown in FIG. 32(b) is formed in such a manner that when the shell plate 2401 is wound around the head portion of the subject 214 in a crossing manner, the unnecessary crossing portions thereof are removed. Through the removal of the crossing portions of the shell plate 2401, a possible twist of the shell plate 2401 in association with the crossing can be prevented. As a result, a possible displacement of the measurement positions in association with the twist can be prevented.

Further, in order not to operate as obstacles when providing such as light stimulation, the shell plate 2401 according to the embodiment 12 is, of course, formed so as not to shield the eyes of the subject 214. Still further, it is, of course, necessary to draw attention on this point when setting the subject 214 to the measurement probe 101 according to the embodiment 12.

Further, in the measurement probe, 101 according to the embodiment 12 the horizontal support column 2403 of circular column shape is used, however, the shape, of the horizontal support column is not limited thereto, for example, if a horizontal support column of prism shape is used, an advantage of preventing rotation of the support column itself when adjusting the let-out amount of the horizontal support column 2403 can be achieved. Another measure for preventing rotation of the horizontal support column 2403 is realized in such a method in which while providing a convex portion and/or concave portion along the extending direction of the horizontal support column 2403 formed in a circular column shape and a concave portion and/or a convex portion is further formed in the hole provided for the adjustable support column 2402 so as to fit the convex portion and/or the concave portion of the horizontal support column 2403. Further, the cross sectional configuration of the horizontal support column 2403 can be formed such as in an elliptical shape and in a combined shape of circle and straight line as well as the hole configuration provided in the adjustable support column 2402 can be formed so as to correspond to the shape of the horizontal support column 2403.

Figure 33:
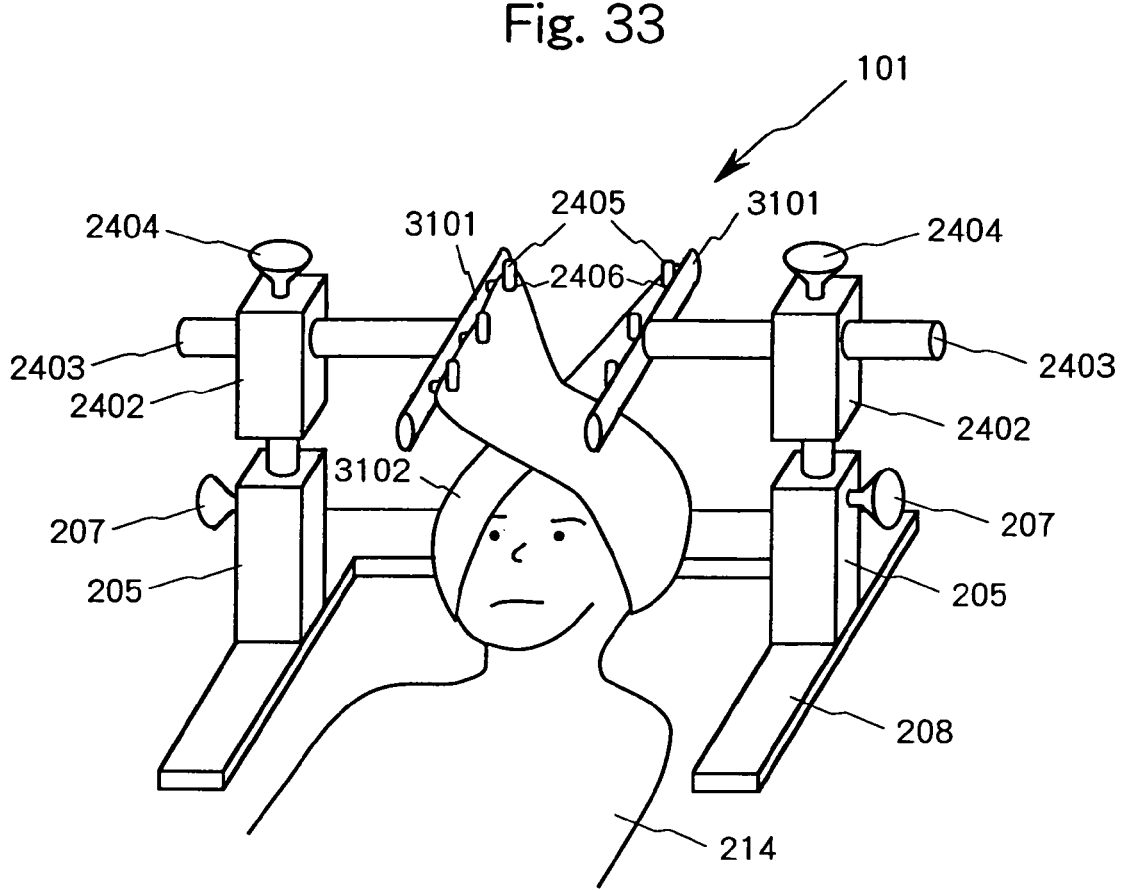
FIG. 33 is a view for explaining a constitution example of another shell plate used in another measurement probe in the embodiment 12 according to the present invention.

Further, in the embodiment 12, the shell plate 2401 is constituted so that the both ends thereof are respectively supported at one position, however, the present invention is not limited to such structure, for example, as shown in FIG. 33, the supporting member is constituted in such a manner that after providing a second horizontal support column 3101 in perpendicular to the horizontal support columns 2403 at each one end thereof, a plurality of hook pins 2405 are provided along the respective second horizontal support columns 3101. On the other hand, the shell plate 3102 is constituted in such a manner that the width H of the both end portions of the shell plate 3102 matches to the length of the second horizontal support column 3101 and a plurality of holes 2406 are formed at the both ends of the shell plate 3102 along the width direction thereof so as to permit hooking to the respective hook pins 2405. In the present embodiment through hooking the respective holes 2406 into the corresponding hook pins 2405, it is possible to enhance stability of the subject 214 in the body axis during measurement. However, the structure of the shell plate 3102 is substantially the same as the previously explained shell plate 2401 other than the elongated width H at the both ends and the provision of the plurality of holes 2406 therein.

Figure 34:
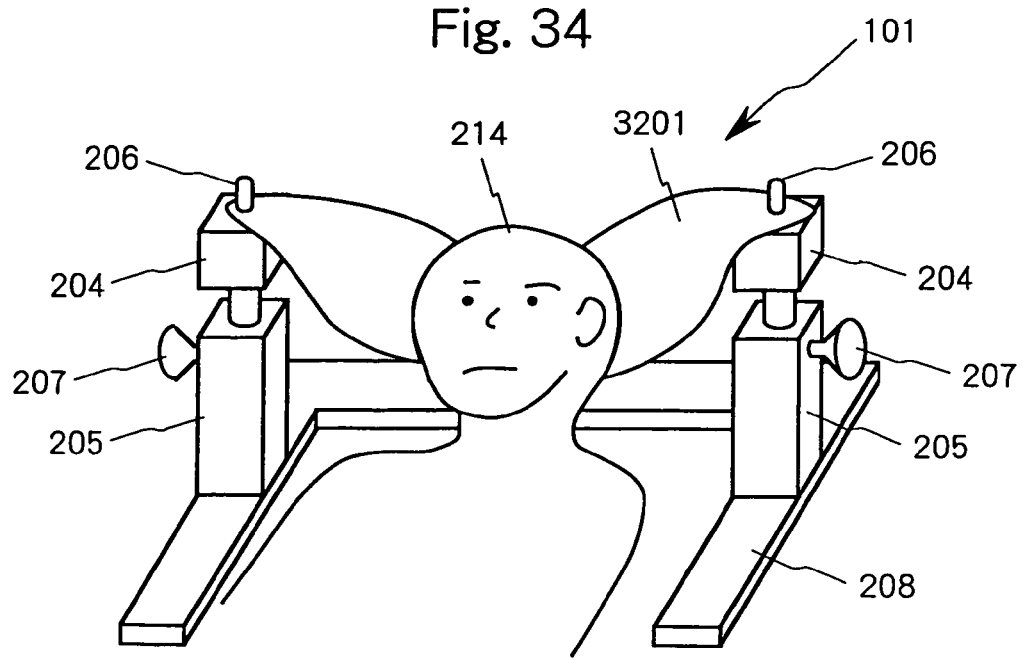
FIG. 34 is a view for explaining a constitution example of still another shell plate used in still another measurement probe in the embodiment 12 according to the present invention.

Further, as shown in FIG. 34, the shell plate 3201 can, of course, be used simply by hooking to the support member according to the embodiment 1 without winding the same around the head portion of the subject 214.

Embodiment 13

Figure 35:
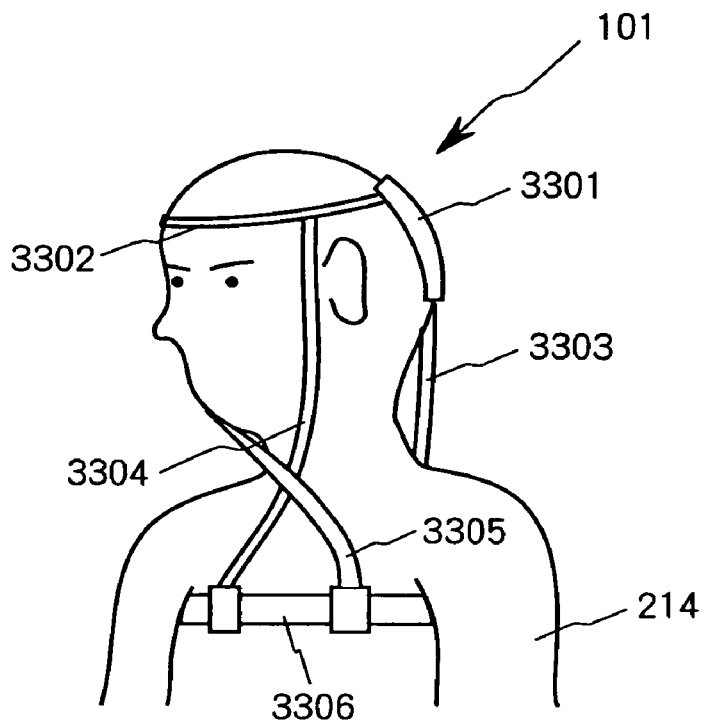
FIG. 35 is a view for explaining a schematic constitution of a measurement probe in a biological optical measurement instrument representing embodiment 13 according to the present invention.

FIG. 35 is a view for explaining a schematic structure of a measurement probe 101 in a biological optical measurement instrument representing the embodiment 13 according to the present invention, wherein 3301 shows a shell plate, 3302 a forehead fixing band, 3303 a back side belt, 3304 a first front side belt, 3305 a second front side belt and 3306 a body band.

The measurement probe 101 according to the embodiment 13 is constituted by the shell plate 3301, the forehead fixing band 3302 of which respective ends are disposed at the upper end portions of the shell plate 3301, the first front side belt 3304 and the second front side belt 3305 of which respective one ends are fixed to the forehead fixing band 3302, the back side belt 3303 of which one end is disposed at the lower end portion of the shell plate 3301 and the body belt 3306 to which other ends of the first and second front side belts 3304 and 3305 and the back side belt 3303 are fixed.

As shown in FIG. 35, when attaching the measurement probe 101 according to the embodiment 13, the forehead fixing band 3302 is attached to the forehead of the subject 214 and the body belt 3306 is attached around the chest of the subject 214. At this instance, the first and second front side belts 3304 and 3305 are arranged so as to cross each other at the lower portion of the jaw, in that at the throat of the subject 214, thereby, a possible loosening of the first and second front side belts 3304 and 3305, when the subject 214 moves the head portion, can be absorbed.

Figure 36:
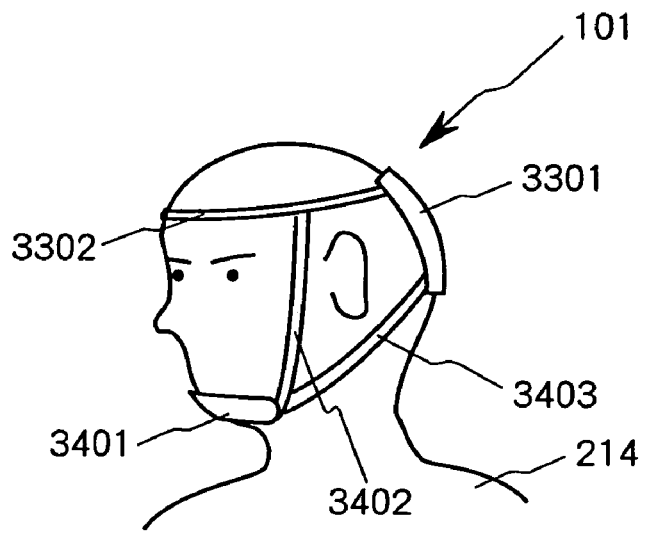
FIG. 36 is a view for explaining a schematic constitution of another measurement probe in the biological optical measurement instrument representing the embodiment 13 according to the present invention.

Although in the measurement probe 101 according to the embodiment 13 a body harness type measurement probe is used in which the other ends of the first and second front side belts 3304 and 3305 and the back side belt 3303 are fixed to the body belt 3306, however, the present invention is not limited to such type, for example, as shown in FIG. 36, a chin guard type measurement probe can, of course, be used in which a chin use plate 3401 to be disposed at the chin of the subject is provided, and to the chin use plate 3401 ends of two front side belts 3402 extending from the forehead fixing belt 3302 and ends of right and left two back side belts 3403 attached to the lower end portions of the shell plate 3301 are fixed.

Figure 37:
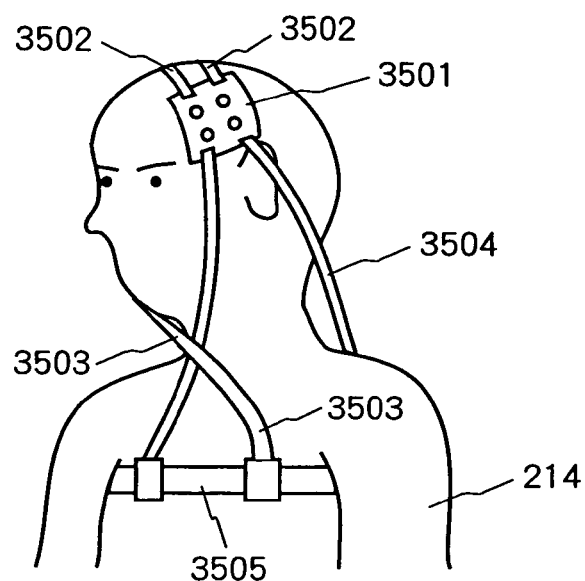
FIG. 37 is a view for explaining a schematic constitution of still another measurement probe in the biological optical measurement instrument representing the embodiment 13 according to the present invention.

Further, as shown in FIG. 37, when performing measurement of right and left side head portions of the subject 214, shell plates 3501 arranged right and left respectively are coupled by two coupling belts 3502 arranged at the upper portion thereof. On the other hand, at the lower portions of the shell plates 3504 one ends of a front side belt 3503 and a back side belt 3504 are fixed. The other ends of the front side belt 3503 and the back side belt 3504 are respectively fixed to a body belt 3505 which is attached to the chest of the subject 214. At this instance, the front side belts 3503 from the right and left shell plates 3501 are arranged so as to cross each other under the chin of the subject 214. The back side belts 3504 from the right and left shell plates 3501 are likely arranged so as to cross each other at the back portion of the subject 214. In particular, when disposing the shell plates 3501 at the side head portion, through the respective crossings of the front side belts 3503 and the back side belts 3504, an advantage which prevents floating of the right and left shell plates 3501 from the epiderm of the subject 214 can be achieved.

Figure 38:
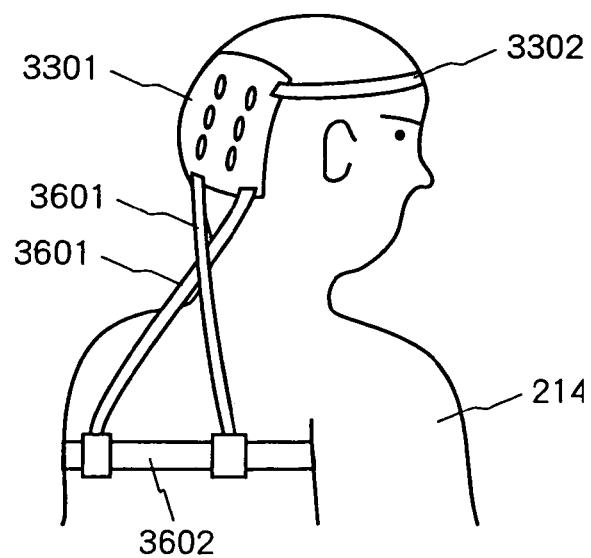
FIG. 38 is a view for explaining a schematic constitution of a further measurement probe in the biological optical measurement instrument representing the embodiment 13 according to the present invention.

Still further, when arranging a shell plate 3301 at the occiput of the subject 214, as shown in FIG. 38, one ends of back side belts 3601 which are fixed at the lower portions of the shell plate 3301 can be fixed to a body belt 3602 attached to the chest of the subject 214. At this instance, it is likely preferable to cross the back side belts 3601 each other at the back portion of the subject 214.

Embodiment 14

Figure 39:
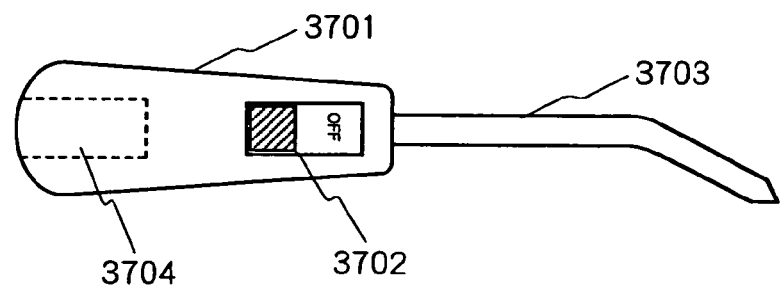
FIG. 39 is a view for explaining a schematic constitution of a hair avoiding jig in embodiment 14 according to the present invention.

FIG. 39 is a view for explaining a schematic structure of a hair avoiding jig in the embodiment 14 according to the present invention, wherein 3701 shows a holder portion, 3702 a switch, 3703 a guide and 3704 a battery cover.

As shown in FIG. 39, the hair avoiding jig according to the embodiment 14 is constituted by the holder portion 3701 and the guide 3703 extending from the holder portion 3701.

In the holder portion 3701, not shown battery and light source are built-in and at the side face of the holder portion 3701 the switch 3702 is disposed. Further, at the back face of the holder portion 3701 the battery cover 3704 is disposed, and through opening and closing of the battery cover an exchange of the battery is performed.

The guide 3703 is formed of a well known transparent plastic material in a shape of circular column or prism and one end thereof is disposed adjacent the light source to be built-in in the holder portion 3701. Thereby, light emitted from the light source passes through the guide 3703 and is irradiated from the other end thereof.

Further, the guide 3703 in the hair avoiding jig according to the embodiment 14 is bent near the end, in that near the top end thereof. Accordingly, even when performing hair avoiding while positioning the hair avoiding jig in parallel with the epiderm at the hair avoiding work, with the contacting angle to the epiderm of the top end portion of the guide 3703, the efficiency of hair avoiding work is enhanced.

Figure 40:
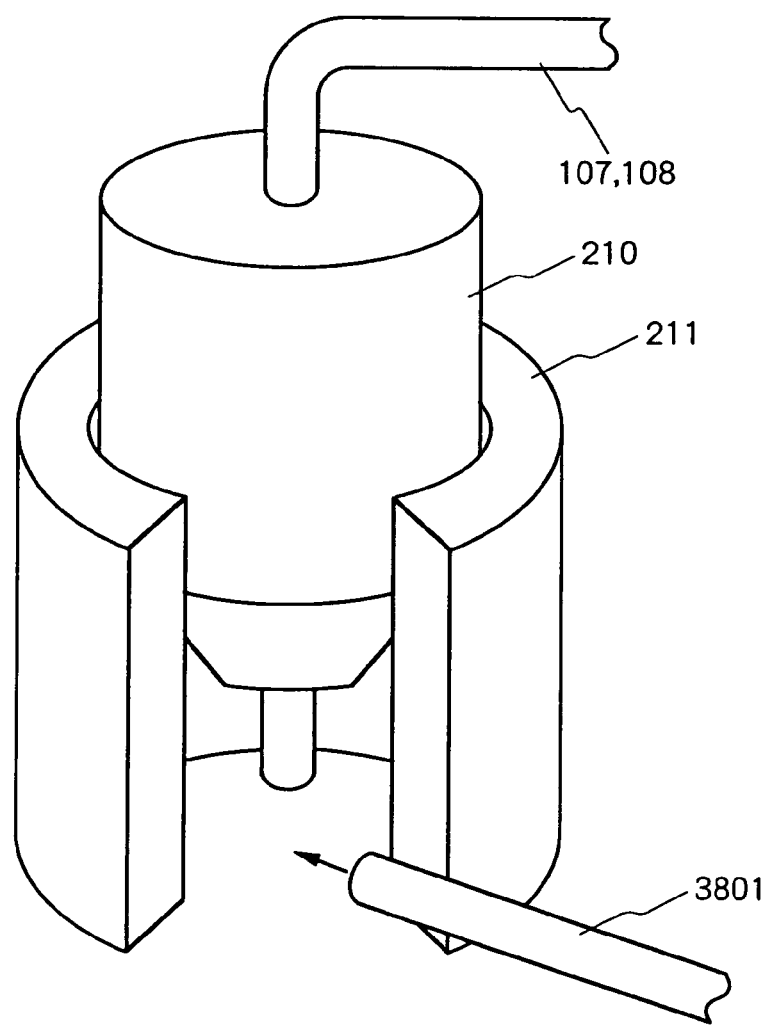
FIG. 40 is a view for explaining a schematic constitution of another hair avoiding jig in embodiment 14 according to the present invention.

Still further, as another hair avoiding jig, a well known air blower 3801 can be used. When performing hair avoiding by making use of the air blower 3801, as shown in FIG. 40, through injecting compressed air from a cut-out portion, of the holder 211 in the arrowed direction, a hair is avoided by the wind velocity.

Embodiment 15

Figure 41:
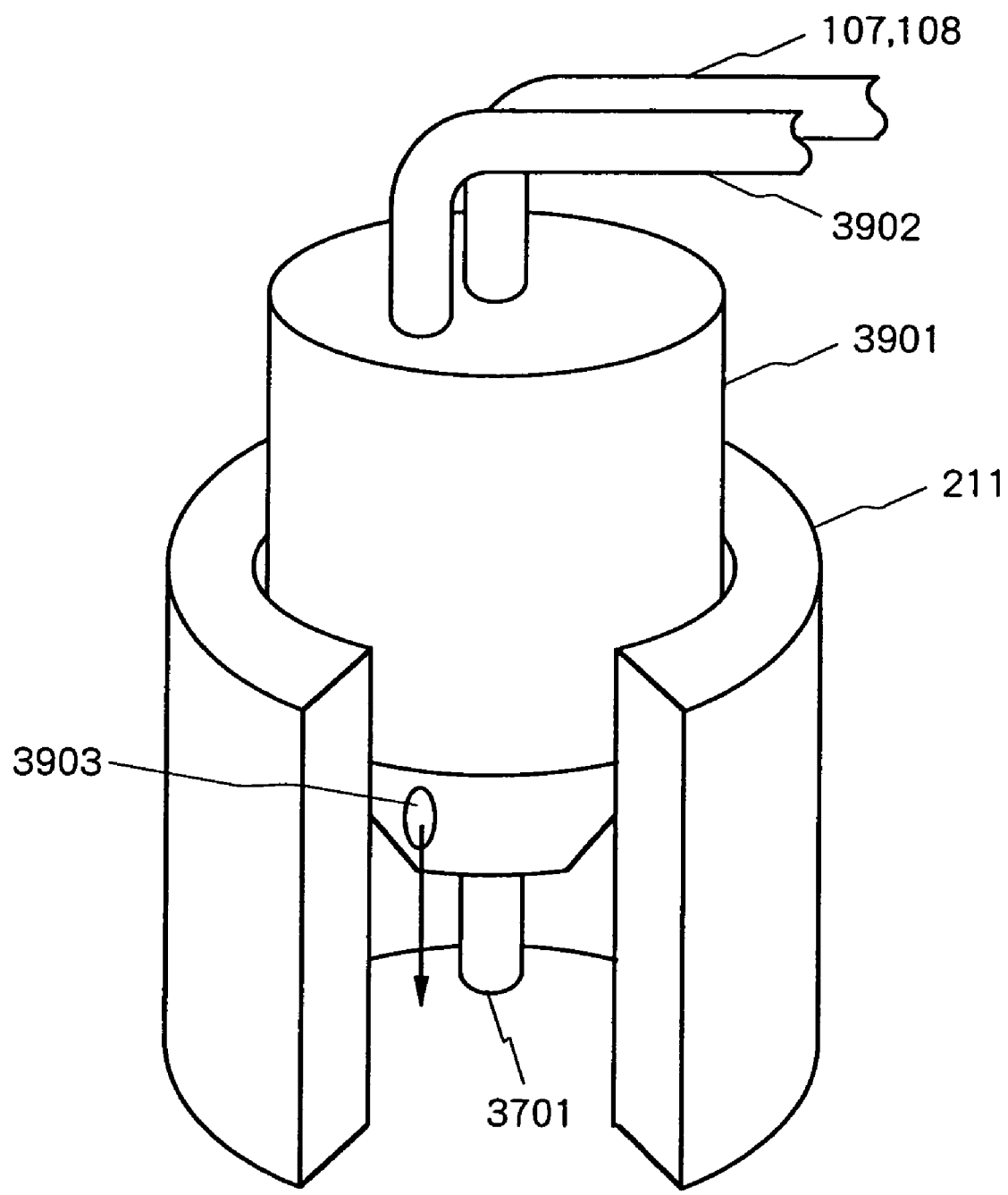
FIG. 41 is a view for explaining a schematic constitution of a probe casing in a biological optical measurement instrument representing embodiment 15 according to the present invention.

FIG. 41 is view for explaining a schematic structure of a probe casing and a probe holder in a biological optical measurement instrument representing the embodiment 15 according to the present invention, wherein 3901 shows a probe casing, 3902 an air hose and 3903 an air injection port. However, in the following explanation, only the structure of the probe casing 3901 will be explained which is different from that in the biological optical measurement instrument according to the embodiment 1.

As shown in FIG. 41, at the top end portion of the probe casing 3901 according to the embodiment 15 the air injection port 3902 serving as the compressed air injecting port is formed. Further, at the other end side of the probe casing 3901 the air hose 3902 which supplies the compressed air to the probe casing 3901 is disposed in addition to the irradiation use or detection use optical fiber 107 or 108. The air hose 3902 is connected to a not shown compressor and supplies compressed air produced by the compressor to the probe casing 3901.

Accordingly, when attaching the probe casing 3901 to the probe holder 211 to be disposed at the shell plate attached to the not shown head portion of the subject 214, since the compressed air is injected in the arrowed direction, a possible hair existing at the top end portion of the probe casing 3901, in that at the top end portion of the optical fiber is to be avoided by the wind velocity. Namely, with the probe casing 3901 according to the embodiment 15, the hair avoiding can be effected without using the aforementioned hair avoiding use jig, thereby, work efficiency of biological optical measurement can be enhanced.

Further, since the hair avoiding is required at the time of attaching the probe casing 3901, the high velocity air supply from the air injection port 3903 can be interrupted by stopping operation of the not shown compressor during measurement.

Embodiment 16

Figure 42:
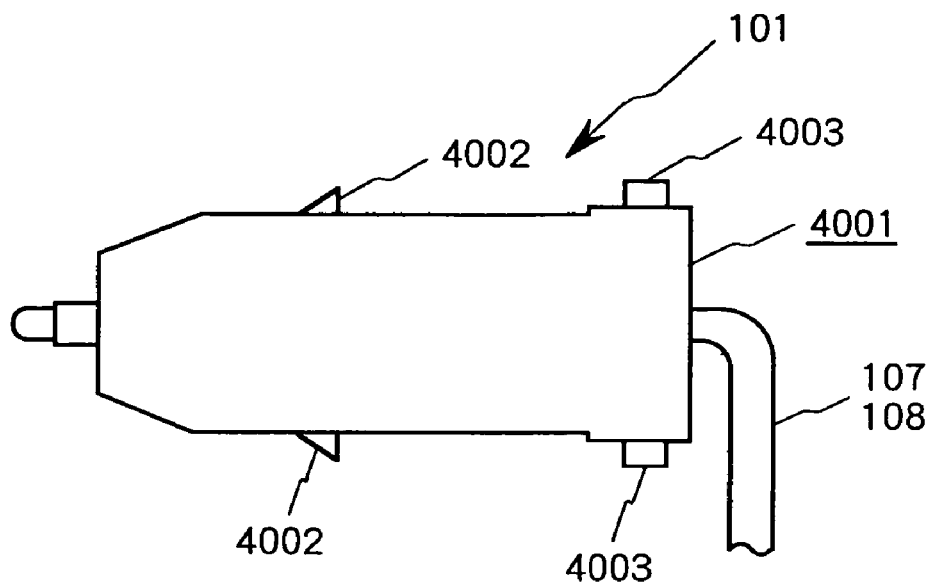
FIGS. 42(a) and 42(b) are views for explaining a schematic constitution of a probe casing and a probe holder used for a measurement probe in a biological optical measurement instrument representing embodiment 16 according to the present invention.
Figure 42:
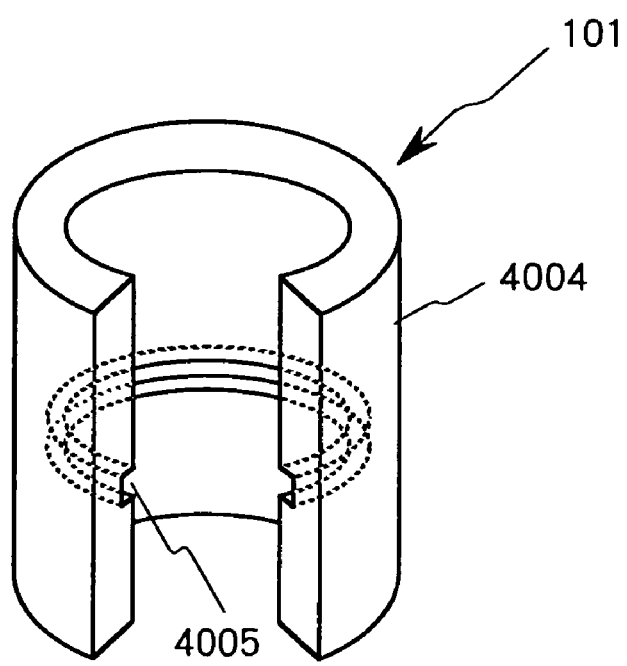

FIGS. 42(a) and 42(b) are views for explaining a schematic structure of a measurement probe 101 in a biological optical measurement instrument representing the embodiment 16 according to the present invention, in particular, FIG. 42(a) is a side view for explaining a schematic structure of a probe casing according to the present embodiment 16 and FIG. 42(b) is a perspective view for explaining a schematic structure of a probe holder according to the embodiment 16. However, in the following explanation, only the structure of a probe casing 4001 and a probe holder 4004 will be explained which is different from that in the biological optical measurement instrument according to the embodiment 1.

In FIGS. 42(a) and 42(b), 4001 shows a probe casing, 4002 a stopper claw, 4003 a release button, 4004 a probe holder and 4005 a fixing groove.

As will be seen from FIG. 42(a), the probe casing 4001 according to the embodiment 16 is provided with the two stopper claws 4002 positioned near the top end of the casing main body. The stopper claws 4002 are interlocked with the release buttons 4003 disposed near the bottom portions of the probe casing 4001 and the stopper claws 4002 are constituted in such a manner that when the release buttons 4003 are pushed toward the center axis direction of the probe casing 4001, the stopper claws 4002 are pulled into the probe casing 4001. Further, the stopper claws 4002 are formed in such a manner that the projection amount in the projecting portion thereof from the probe casing 4001 gradually increases from the top end side to the bottom end side. Further, a detailed structure of the stopper claws 4002 and the release buttons 4003 will be explained later.

On the other hand, as shown in FIG. 42(b), along the inner circumference of the probe holder 4004 the fixing groove 4005 having a predetermined width is formed, and when the probe casing 4001 is inserted into the probe holder 4004, the stopper claws 4002 are fitted into the fixing groove 4005 to thereby fix the probe casing 4001.

In such instance, in the probe casing 4001 according to the embodiment 16 since an inclination is formed on the stopper claws 4002 in such a manner that the projection amount in projecting portion thereof gradually increases in the direction from the top end to bottom end, an attachment work of the probe casing 4001 can be performed without manipulating the release buttons 4003 during insertion of the probe casing 4001, thereby, attachment efficiency can be enhanced.

Figure 43:
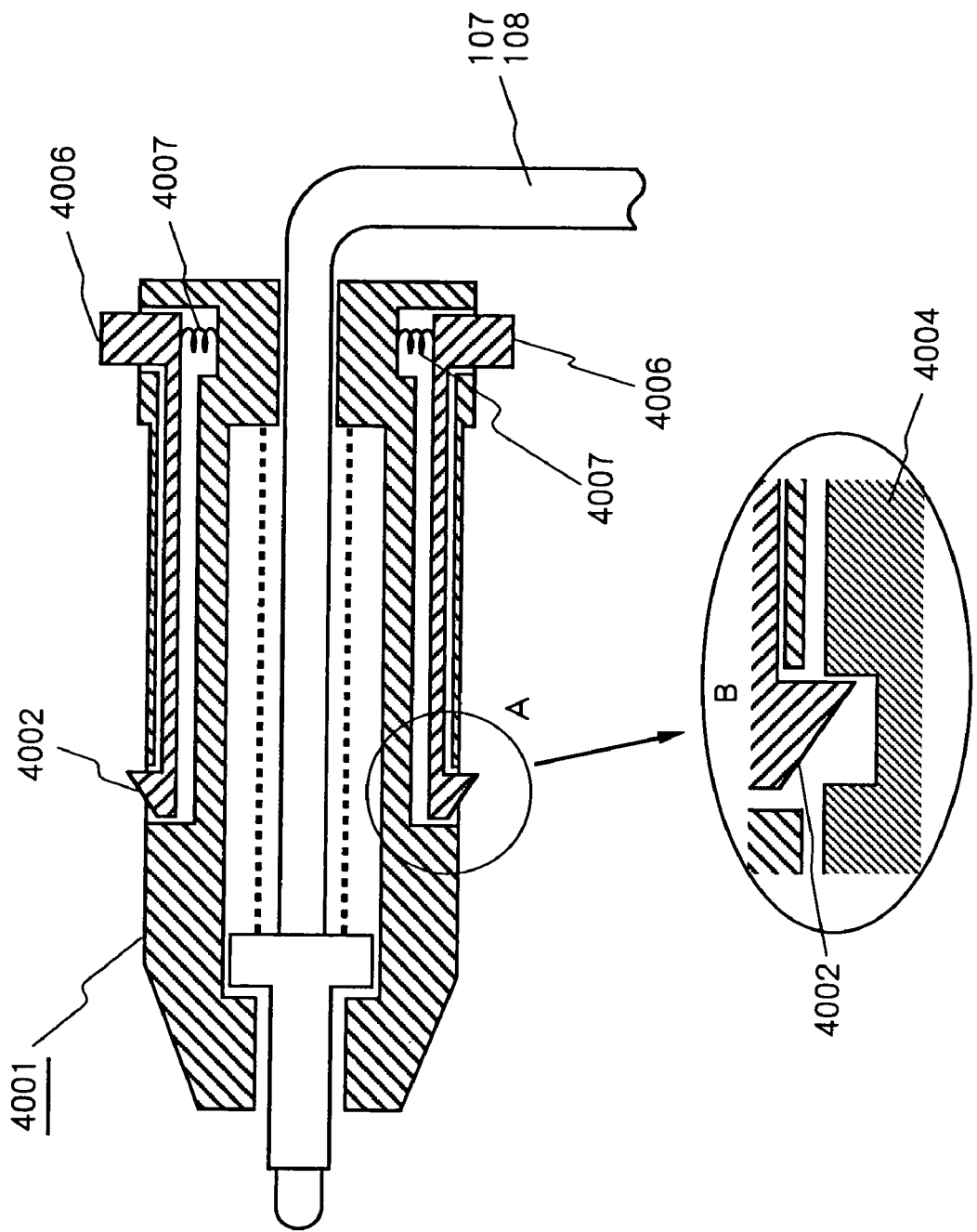
FIG. 43 is a vertical cross sectional side view of the probe casing in the embodiment 16 according to the present invention.

Now, FIG. 43 shows a vertical cross sectional side view of the probe casing 4001 according to the embodiment 16, and hereinbelow the structure of the probe casing 4001 will be explained with reference to FIG. 43.

As shown in FIG. 43, in the probe casing 4001 a stopper member 4006 is disposed at one end of which the stopper claws 4002 are formed and at the other end of which the release buttons 4003 are formed. At one end of the stopper member 4006 one end of a spring 4007 is secured of which other end is secured to the probe casing 4001.

As will be seen from the above, in the probe casing 4001 according to the embodiment 16, since the stopper claw 4002 and the release button 4003 are integrated, when the release button 4003 is pushed in, the stopper claw 4002 is also retreated and the probe casing 4001 is released from the probe holder 4004.

Further, in the embodiment 16, the stopper claws 4002 are provided at the side of the probe casing 4001, however, the present invention does not limited to such structure, the stopper claws 4002 can, of course, be provided at the side of the probe holder 4004.

Still further, in the embodiment 16, the bottom end portion of the stopper claw 4002 is formed to be perpendicular to the center axis of the probe casing 4001, however, likely, the present invention does not limited to such structure, for example, the stopper claws 4002 can, of course, be formed in such a manner that the projection amount gradually decreases. In such instance, through properly adjusting the inclination angle of the stopper claws 4002, when a force more than a predetermined amount is applied to an optical fiber disposed at the top end of the probe casing 4001, the probe casing 4001 can be automatically taken out from the probe holder 4004, thereby, an advantage which prevents damaging of the top end portion of the optical fiber can be achieved.

Embodiment 17

Figure 44:
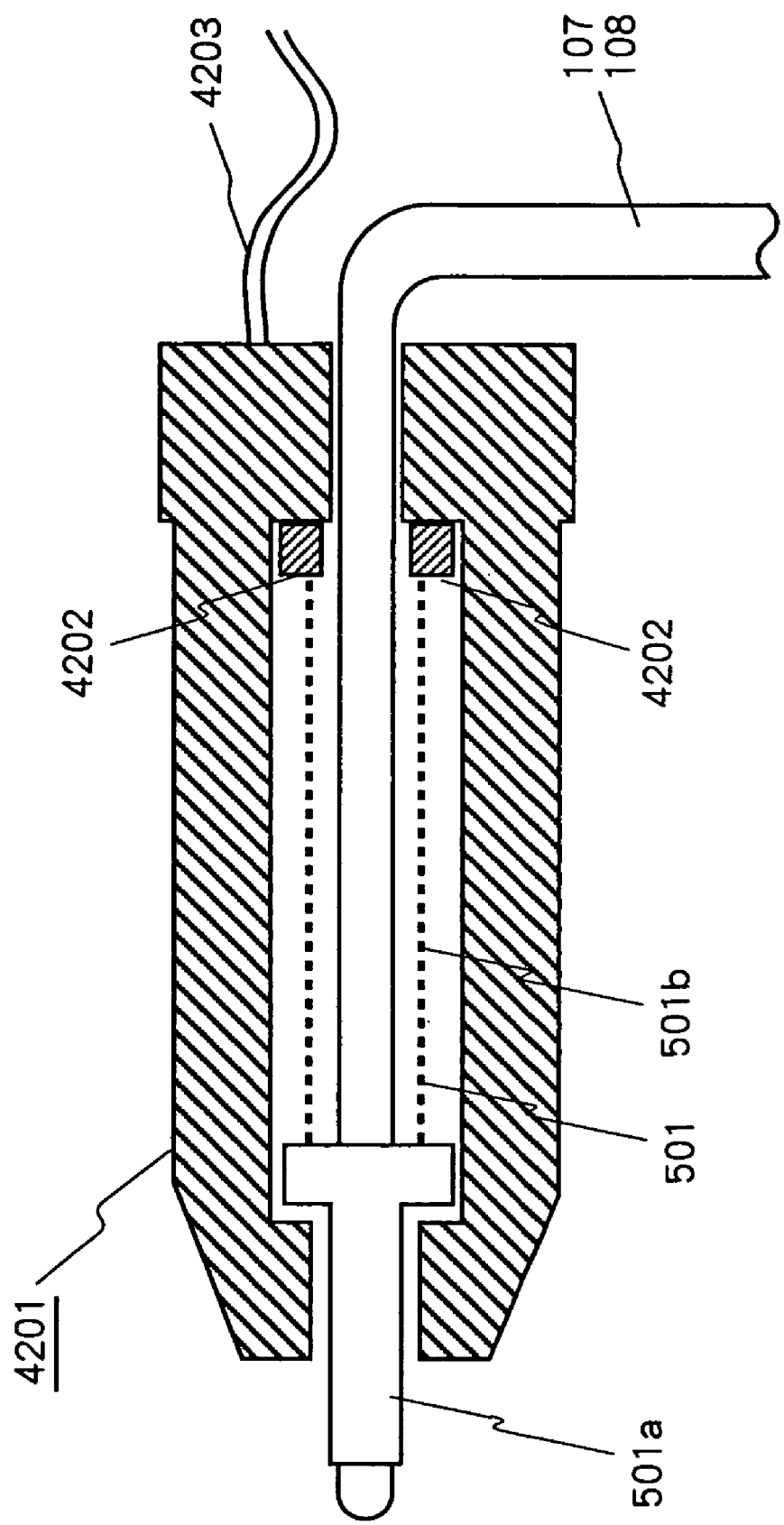
FIG. 44 is a vertical cross sectional side view of a probe casing used for a measurement probe in a biological optical measurement instrument representing embodiment 17 according to the present invention.

FIG. 44 is a vertical cross sectional side-view of a probe casing in a biological optical measurement instrument representing the embodiment 17 according to the present invention, wherein 4201 shows a probe casing, 4202 a pressure sensor, 4203 a sensor cable, 501a a movable portion and 501b a spring. However, in the following explanation, only the structure of the probe casing 4001 will be explained which is different from that in the biological optical measurement instrument according to the embodiment 1.

In FIG. 44, the pressure sensor 4204 is a well known pressure sensor which detects pressure applied onto the spring mechanism 501 and the detected output is outputted to the information processing unit 106 via the sensor cable 4203.

Now, the structure of the probe 4201 according to the embodiment 17 will be explained with reference to FIG. 44.

Like the probe casing 210 as shown in the embodiment 1, in the inner circumferential portion of the probe casing 4201 according to the embodiment 17 the spring mechanism 501 constituted by the spring 501b and the movable portion 501a one end of which is fixed to the spring 501b is disposed. An irradiation use or detection use optical fiber 107 or 108 is secured to the movable portion 501a.

On the other hand, the other end of the spring 501b is fixed to the pressure sensor 4202 which is secured at the inner circumferential face of the probe casing 4201.

To the pressure sensor 4202 one end of the sensor cable 4203 is connected which is led out from a not shown cable leading out port formed in the probe casing 4201 and the other end of which is connected the information processing unit 106.

Accordingly, under a condition in which the probe casing 4201 is attached to a not shown subject 214, the top end portions of the optical fibers 107 and 108 are pressed onto the scalp of the subject 214 through the force pushing out the optical fibers 107 and 108 by the spring mechanism 501. Namely, under the condition in which when the probe casing 4201 is attached to the not shown shell plate being attached to the subject 214 and the top end portions of the optical fibers 107 and 108 are contacted to the epiderm at the measurement position, the spring 501b keeps a compressed condition.

As a result, the pressure applied to the pressure sensor 4202 rises and the detection value is outputted to the information processing unit 106.

Through monitoring the pressure applied to the probe casing 4201 by the information processing unit 106, it is easily monitored whether the top end portions of the optical fibers 107 and 108 are contacted onto the surface of the subject 214. Accordingly, an erroneous measurement due to poor attachment of the measurement probe 101 can be reduced. Further, number of repeating measurement due to erroneous measurement can be reduced which can enhance diagnosis efficiency.

Further, through provision in the information processing unit 106 of a light intensity correcting means which corrects a living body passing light intensity representing measurement data based on the measurement pressure value, measurement error can be suppressed minimum which depends on blood flow variation and difference of passing light transfer efficiency from the scalp to the optical fibers 107 and 108 caused by pressing the epiderm by the optical fibers 107 and 108 which varies depending on the contacting degree of the optical fibers 107 and 108 on to the epiderm. A relationship between the pressure and the correction amount can be determined such as experiments for every measurement portion and every shape of measurement probe 101.

Embodiment 18

Figure 45:
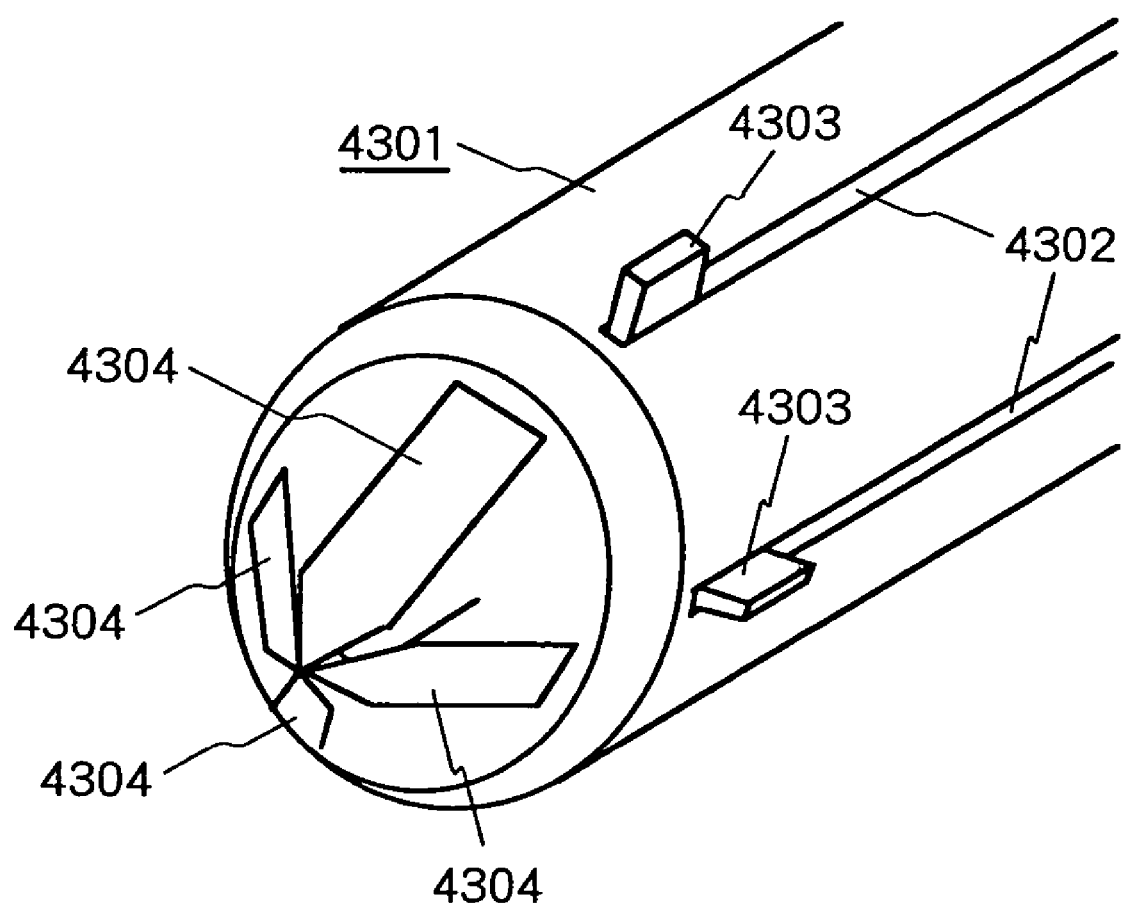
FIG. 45 is a perspective view for explaining a schematic constitution of a probe casing used for a measurement probe in a biological optical measurement instrument representing embodiment 18 according to the present invention.
Figure 46:
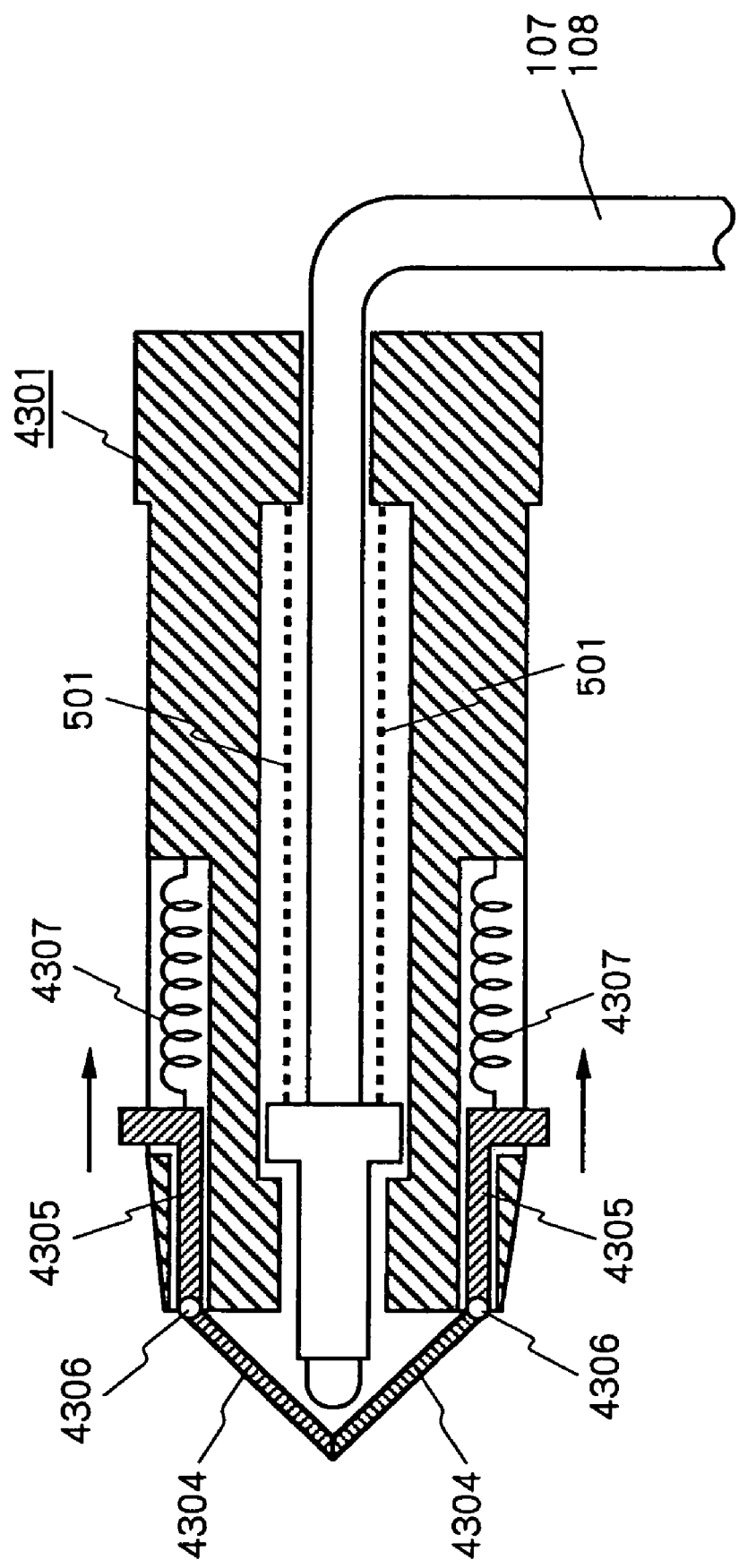
FIG. 46 is a vertical cross sectional view for explaining the structure of the probe casing before attachment thereof of the embodiment 18 according to the present invention.
Figure 47:
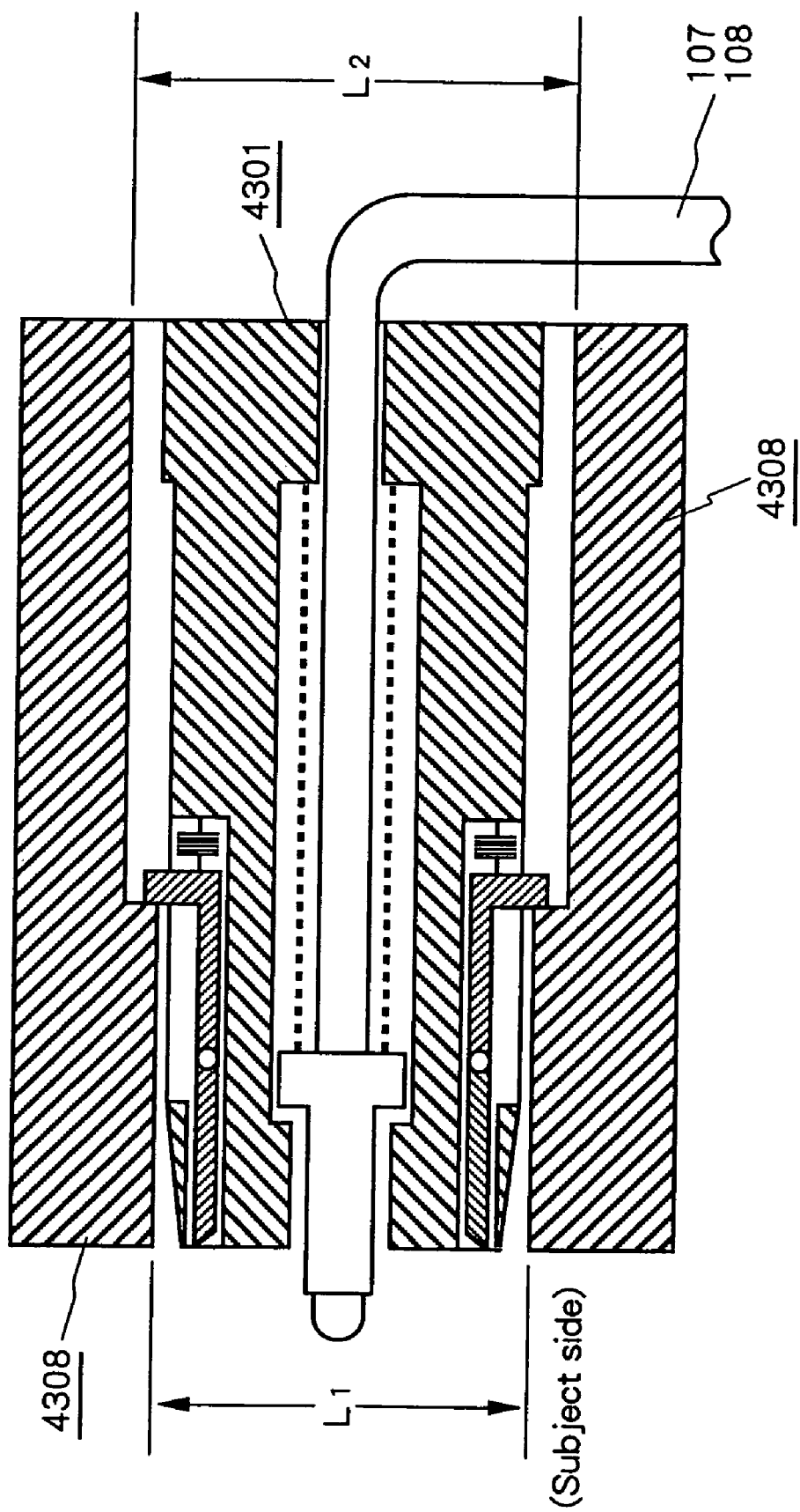
FIG. 47 is a vertical cross sectional view for explaining the structure of the probe casing at the time of attachment thereof of the embodiment 18 according to the present invention.

FIG. 45 is a perspective view for explaining a schematic constitution of a probe casing used for a measurement probe in a biological optical measurement instrument representing the embodiment 18 according to the present invention, FIG. 46 is a vertical cross sectional view for explaining the structure of the probe casing before attachment thereof of the embodiment 18 according to the present invention and FIG. 47 is a vertical cross sectional view for explaining the structure of the probe casing at the time of attachment thereof of the embodiment 18 according to the present invention. However, in the following explanation, only the structure of the probe casing 4301 and the probe holder 4308 will be explained which is different from that in the biological optical measurement instrument according to the embodiment 1.

In FIG. 45 through FIG. 47, 4301 shows a probe causing, 4302 a guide slit, 4303 a sliding claw, 4304 a cover, 4305 a sliding member, 4306 a joint, 4307 a spring and 4308 a probe holder. Hereinbelow, the probe casing 4301 according to the embodiment 18 will be explained with reference to FIG. 45 through FIG. 47.

As will be seen from FIG. 45, the probe casing 4301 according to the embodiment 18 is provided with a shutter mechanism constituted by 4 pieces of covers 4304 disposed at the top end portions of the probe casing 4301 and 4 pieces of sliding claws 4303 disposed at the outer circumference thereof. The 4 pieces of covers 4304 function to cover the optical fiber projecting from the top end portion of the probe casing 4301. The respective covers 4304 are coupled with the respective corresponding sliding claws 4303 and through the displacement of the sliding claws 4303, the respective covers 4304 are stored within the prove casing 4301. However, the displacement of the sliding claws 4303 is limited by the guide slits 4302 formed in parallel with the center axis direction of the probe casing 4301.

Now, the shutter mechanism according to the embodiment 18 will be explained with reference to FIGS. 46 and 47.

As shown in FIG. 46, in the embodiment 18, the sliding members 4305 are disposed in the probe casing 4301 along the respective guide slits 4302. At one end of the sliding member 4305 a well known joint 4306 is attached and at the other end thereof the sliding claw 4303 is formed. The cover 4304 is attached to the joint 4306, through sliding the sliding member 4305 in the arrowed direction the cover 4304 opens and is stored in the probe casing 4306. At respective joints 4306 a not shown well known spring is disposed for closing the respective covers 4304.

At the other end of the sliding member 4305 the well known spring 4307 is disposed, one end of the spring 4307 is fixed to the sliding member 4305 and the other end thereof is fixed to the end portion of the guide slit 4302 formed on the outer circumference of the probe casing 4301. Accordingly, a spring force is always applied to the sliding member 4305 in the direction opposite to the arrowed direction.

On the other hand, on the inner circumferential face of the probe holder 4308 according to the embodiment 18 a step is formed as shown in FIG. 47. Namely, the probe holder 4308 is constituted in such a manner that one inner circumferential diameter at the side where the not shown subject 214 is laid is formed at L1 so as to permit insertion of the main body portion of the probe casing 4301 and another inner circumferential diameter at the remote side from the subject 214 is formed at L2 so as to permit insertion of the portion of the sliding claw 4303. Accordingly, as shown in FIG. 47, when inserting the probe casing 4301 into the probe holder 4308, the sliding claw 4303 is caused to be slided in the arrowed direction at the step portion of the inner circumferential diameters L1 and L2, thereby, the covers 4304 are opened and the top end of the optical fiber is exposed.

As will be apparent from the above, with the measurement probe 101 according to the embodiment 18 only when the probe casing 4301 is inserted (attached) into the probe holder 4308, the covers 4304 in the shutter mechanism are opened and the top end portion of the optical fiber is exposed, thereby, a possible irradiation of laser beams is prevented at the time of non-attachment thereof. Accordingly, attachment and detachment of the main body of the measurement probe 101 and the probe casing 4301 can be performed without interrupting the output of the not shown modulated semiconductor laser 102. As a result, diagnosis efficiency in biological optical measurement can be enhanced.

Further, in the embodiment 18, the covers 4304 in the shutter mechanism protrude in front of the optical fiber and cover the optical fiber, however, the present invention is not limited to such structure, for example, the shutter mechanism can, of course, be constituted in such a manner that the optical fiber is caused to be retreated into the probe casing and the covers cover the top end portion of the optical fiber.

Embodiment 19

Figure 48:
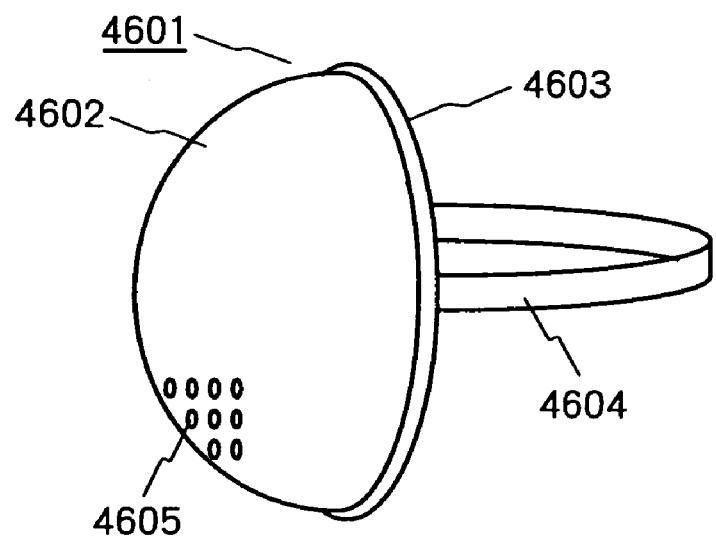
FIGS. 48(a) and 48(b) are views for explaining a schematic constitution of a light beam shielding mask used together with a biological optical measurement instrument representing embodiment 19 according to the present invention.
Figure 48:
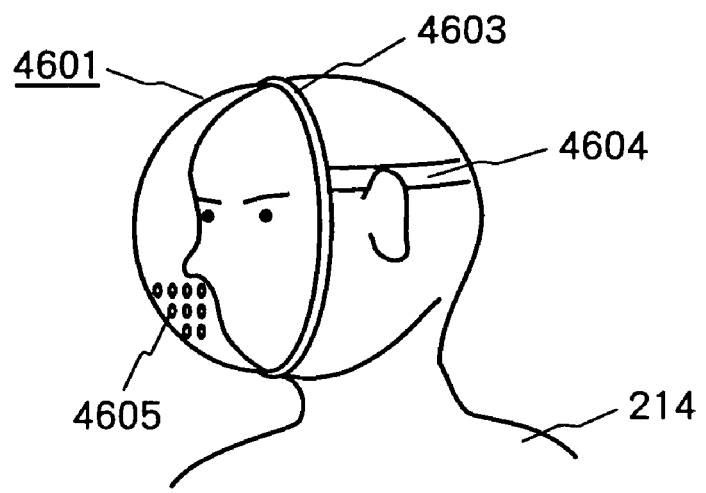
Figure 49:
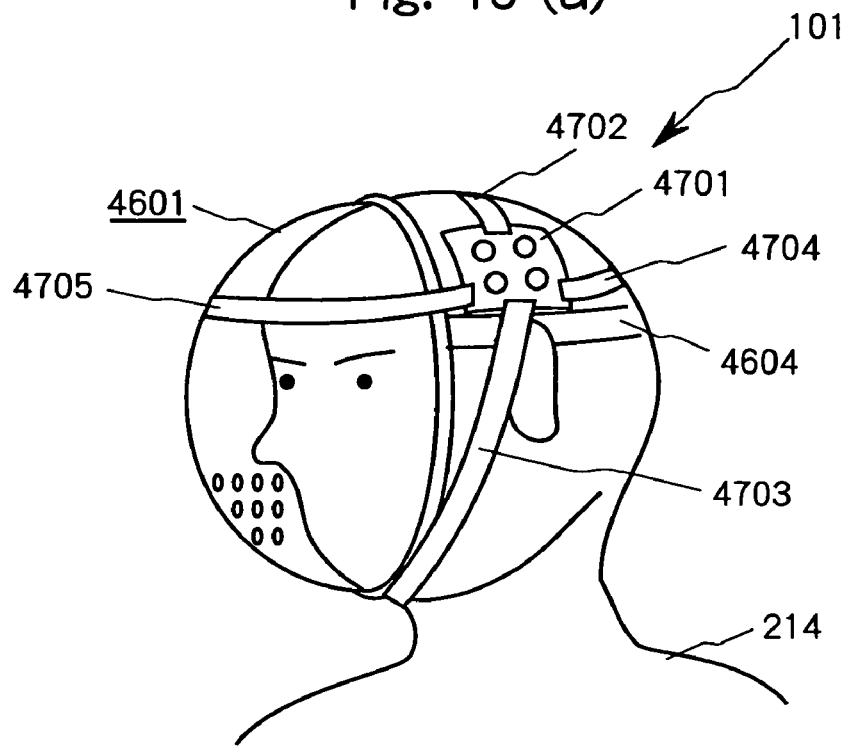
FIGS. 49(a) and 49(b) are views for explaining a schematic constitution of a measurement probe used together with the light beam shielding mask in the embodiment 19 according to the present invention.
Figure 49:
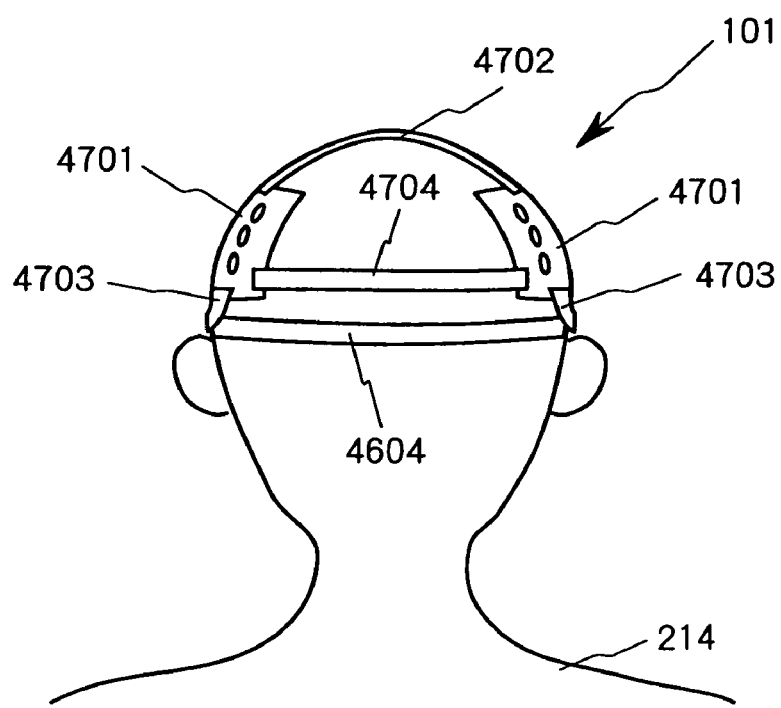

FIGS. 48(a) and 48(b) are views for explaining a schematic constitution of a light beam shielding mask representing the embodiment 19 according to the present invention and FIGS. 49(a) and 49(b) are views for explaining a schematic constitution of a measurement probe 101 the embodiment 19 according to the present invention. In particular, FIG. 48(a) is a perspective view of the light shielding mask according to the embodiment 19, FIG. 48(b) is a view for explaining an attachment state of the light shielding mask, FIG. 49(a) is a perspective view for explaining a schematic structure of the measurement probe 101 according to the embodiment 19 and FIG. 49(b) is a back side view for explaining a schematic structure of the measurement probe 101 according to the embodiment 19.

In FIGS. 48(a), 48(b), 49(a) and 49(b), 4601 shows a light shielding mask, 4602 a light shielding member, 4603 a cushion member, 4604 a fixing member, 4605 an air inlet port, 4701 a shell plate and 4702-4705 fixing belts.

As will be seen from FIG. 48(a) as the light shielding mask 4601 according to the embodiment 19 a material such as plastics having a large absorption of near infrared rays is used and the light shielding member 4602 is formed by molding such material in a comical shape. At the end portion of the light shielding member 4602 in order to reduce feeling of strangeness when the mask is attached, material such as rubber, sponge and vinyl leather cushion filling sponge therein is disposed as the cushion member. Further, the cushion member 4603 functions to prevent a gap generation between the light shielding member 4601 and the head portion of the subject 214 caused by such as unevenness of human faces having large individual differences.

Further, at end portions of the light shielding member 4602 a well known fixing member 4604 is provided which is used for fixing the concerned light shielding mask onto the head portion of the subject 214. The fixing member 4604 according to the embodiment 19 is constituted by an expandable band which is to be bridged between opposing end positions of the light shielding member 4602. It is, of course, necessary to arrange the fixing member 4604 at a position which never interferes the measurement portion. For this purpose, a well know sliding mechanism which permits vertical displacement of the attachment position of the fixing member 4604 can be provided at the end portions of the light shielding member 4602. Alternatively, a plurality of light shielding masks 4601 having different attachment positions can be prepared so as to permit free selection thereof depending on the concerned measurement position.

A plurality of holes which serve as air inlets 4605 are formed at the surface of the light shielding member 4602. The air inlet ports 4605 are formed at a position which corresponds to the mouth of the subject 214 at the time of attachment thereof as shown in FIG. 48(b). Thereby, a possible load caused to the subject 214 is reduced.

As will be seen from FIG. 48(b), the attachment position of the light shielding mask 4601 according to the embodiment 19 is the head portion of the subject 214, therefore, through attaching the same so that the light shielding member 4602 covers the face, direct irradiation of near infrared light onto the face at the time of attachment and detachment of the not shown probe casing can be prevented.

Now, the structure of the measurement probe 101 for measurement of side head portion according to the embodiment 19 will be explained with reference to FIGS. 49(a) and 49(b).

As will be seen from FIGS. 49(a) and 49(b), the measurement probe 101 according to the embodiment 19 is constituted by two pieces of shell plates 4701 on which not shown probe holders are disposed and by first through fourth fixing belts 4702, 4703, 4704 and 4705 which serve to attach the shell plates 4701 to the subject 214. Further, at predetermined positions on the respective shell plates 4701 the not shown probe holders are disposed.

The first belt 4702 is arranged at the top head portion, the second belt 4703 is arranged at the chin portion, the third belt 4704 is arranged at the back head portion and the fourth belt 4705 is arranged at the face side. At this instance, in the embodiment 19, when attaching the measurement probe 101 to the subject 2i4 to which the light shielding mask 4601 is attached as shown in FIG. 49(a), the fourth belt 4705 has to be fasten over the light shielding mask 4601, therefore, the length thereof has to be determined in view of the light shielding member 4602.

As will be seen from FIG. 49(b), even under the condition when the light shielding mask 4701 and the measurement probe 101 are attached, the fixing member 4604 never touches the shell plates 4701, thereby, a biological optical measurement can be performed at a desired measurement position.

Further, the light shielding mask 4601 according to the embodiment 19 is constituted so as to cover only the face of the subject 214, however, the present invention is not restricted to such embodiment, for example, the light shielding member 4602 can be, of course, arranged at the face portion of the shell plates 2201 and 2204 according to the embodiment 10. Still further, such a shell plate can be provided in which probe holders are disposed at such as the back head portion and the side head portion while disposing the light shielding member 4602 at the face portion of the shell plate covering only the head portion of the subject 214 like a face mask for fencing.

Still further, since the individual difference of head portion size is comparatively large, if a plurality kind of light shielding masks are prepared in advance and a most proper one is selected and used depending on the shape of the head portion of the subject 214, a possible gap occurrence between the light shielding mask 4601 and the head portion can be prevented.

Figure 50:
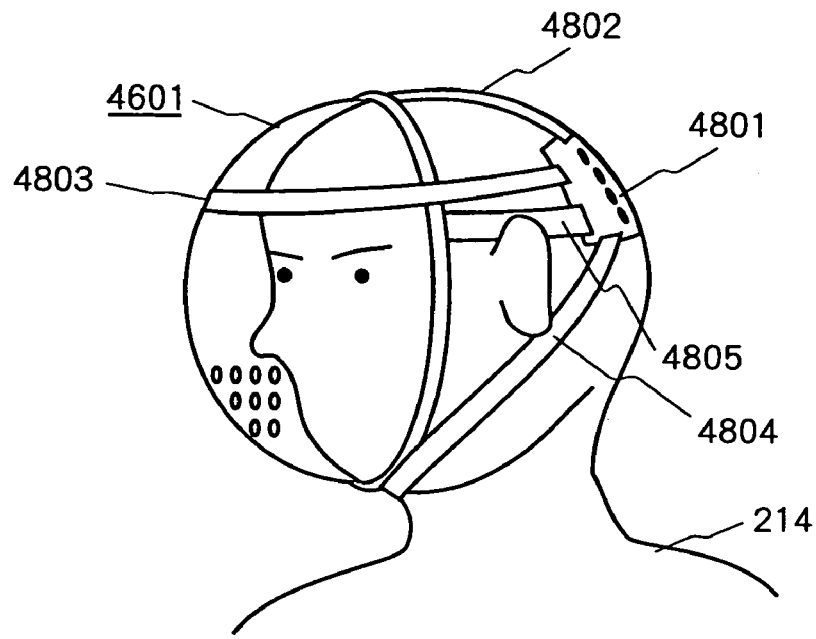
FIGS. 50(a) and 50(b) are views for explaining a schematic constitution of another measurement probe used together with the light beam shielding mask in the embodiment 19 according to the present invention.
Figure 50:
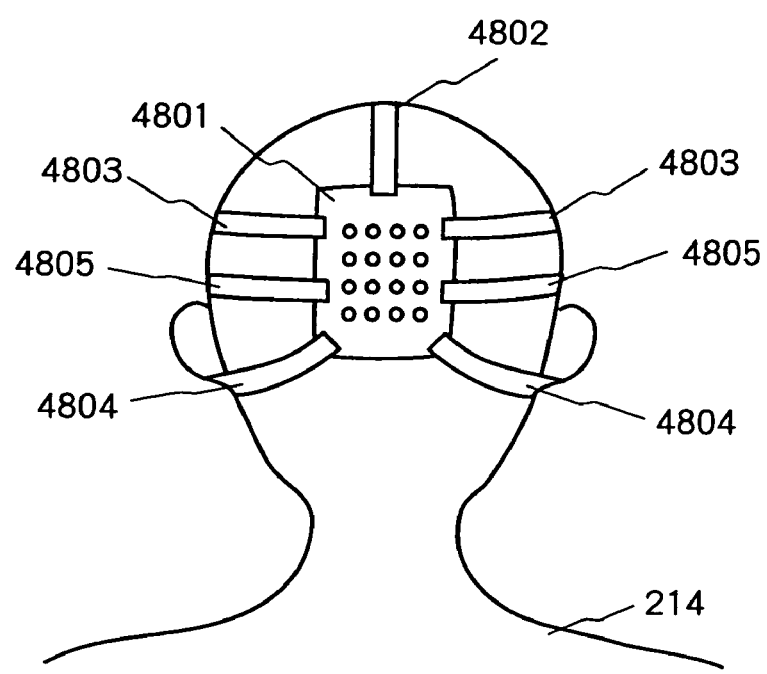

Still further, as shown in FIGS. 50(a) and 50(b), when fixing one ends of fixing members 4802 through 4805 which attach the light shielding mask 4601 to the subject 214 to a shell plate 4801, in other words, when forming integrally the light shielding mask 4601 and the measurement probe 101, the attachment of the light shielding mask 4601 and the measurement probe 101 can be performed at the same time, thereby, diagnosis efficiency can be enhanced. Moreover, when forming the light shielding mask 4601 and the measurement probe 101 integrally, an advantage can be achieved that a possible touching between the shell plate 4801 and the fixing members 4802 through 4805 at the time of attachment can be prevented.

Embodiment 20

Figure 51:
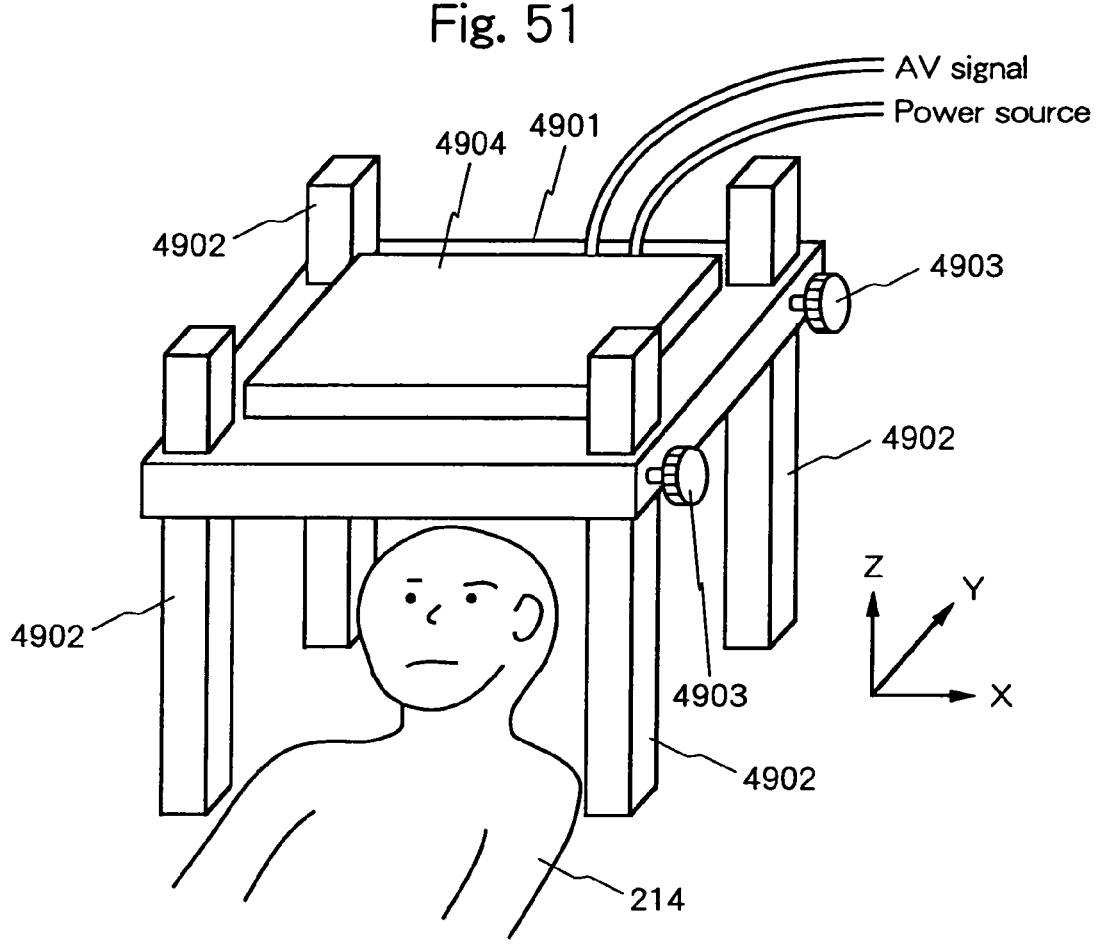
FIG. 51 is a view for explaining a schematic constitution of a stimulation unit in a biological optical measurement instrument representing embodiment 20 according to the present invention.

FIG. 51 is a view for explaining a schematic structure of a stimulation unit in a biological optical measurement instrument representing the 101 embodiment 20 according to the present invention, wherein 4901 shows a display support portion, 4902 a support pillars, 4903 height adjustment screws and 4904 a display unit. However, in the following explanation, like the embodiment 4 only the structure of the stimulation unit will be explained which is different from that in the biological optical measurement instrument according to the embodiment 1. X, Y and Z in FIG. 51 respectively show X axis; Y axis and Z axis.

As will be seen from FIG. 51, the stimulation unit according to the embodiment 20 is constituted by the flat plate shaped display support portion 4901 at the center portion of which the display unit 4904 is arranged, four pieces of the support pillars 4902 which are arranged at four corners of the display support portion 4901 and hold the display support portion at a predetermined height, four pieces of the height adjustment screws 4903 disposed at the side faces of the display support portion 4901 and the display unit 4904 disposed at the center portion of the display support portion 4901.

The display unit 4904 is constituted, for example, like the embodiment 4, by a well known not shown liquid crystal display unit and a well known not shown speaker disposed at the same side as the display face of the liquid crystal unit.

The center portion of the display support portion 4901 is opened and at the opened portion thereof the display unit 4904 is disposed. Further, at the respective four corners of the display support portion 4901 holes which penetrate in Z axis direction are formed and each of the support pillars 4902 is inserted into the respective holes. At least one length in X axis and Y axis directions of the display support portion 4901 is formed longer than the width of the head portion of the subject 214 for the measurement object.

The height adjustment screws 4903 are disposed on the side faces of the display support portion 4901, in that on a plane parallel to Z axis. The length of the height adjustment screws 4903 is set so that the top ends thereof project from the inner circumferential faces of the holes formed at the four corners of the display support portion 4901.

Accordingly, in the stimulation unit according to the embodiment 20, through adjustment of the fixing position of the display support portion 4901 by the height adjustment screws 4903, the distance from the subject 214 to the display face of the display unit 4904 can be set freely. Thereby, the measurement can be performed properly for all of the subjects 214 such as adults and children having different size of head portions. Further, when relaxing after applying an intense stimulation and when the subject 214 can not concentrate to one point, the height thereof can be adjusted.

Still further, in the stimulation unit according to the embodiment 20, since the respective heights of the four support pillars 4902 can be adjusted independently, for example, even when there is an unevenness where the stimulation unit is installed or when the installation position is inclined, the stimulation unit can be disposed in parallel with the subject 214 which is one of advantages.

As has been explained hitherto, in the stimulation unit according to the embodiment 20, since the position of the display unit 4904 can be set freely, the display unit can be set at an optimum position so as to meet with the line of sight position of the subject. Namely, through displacing the stimulation unit along the body axis, measurement causing the line of sight downward, measurement causing the line of sight front ward and measurement causing the line of sight upward can be selected depending on necessity. Accordingly, the present embodiment is suitable for giving light stimulation to a baby who has difficulty of directing the line of sight upward and biological optical measurement causing the line of sight downward can be performed easily.

Further, in the embodiment 20, a liquid crystal display unit is used for the display unit 4904 serving as a light stimulation generating means, however, the present invention is not limited thereto, for example, a well known light bulb, a stroboscope unit, a projector unit and a back light unit used for a liquid crystal unit can be, of course, used. Like the embodiment 4, when performing biological optical measurement for a baby as the subject 214, since it is difficult to draw attention to the display unit 4904, a light bulb, a stroboscope unit and a projector unit capable of emitting light with a comparatively high capacity are suitable.

Further, if a plurality kind of units such as a light bulb, a stroboscope unit, a projector, unit and a back light unit are prepared in advance and a kind of unit which is arranged on the display support portion 4901 is properly selected depending on measurements such as measurement which provides a simple light stimulation such as light flashing and measurement which provides complex light stimulation such as light patterns, an optimum light stimulation can be provided to the subject 214, thereby, the measurement accuracy can be enhanced.

Figure 52:
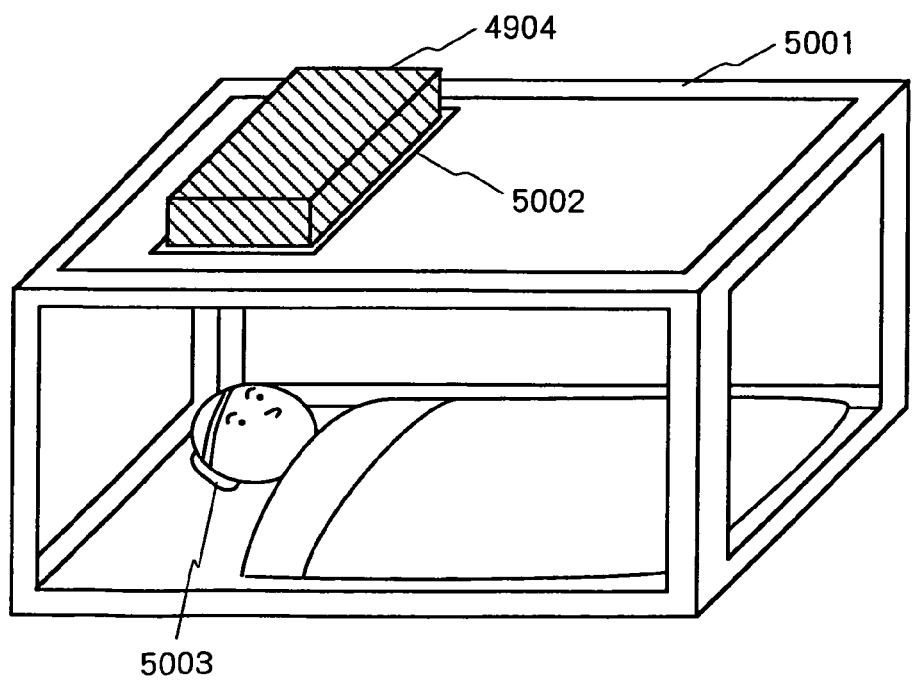
FIG. 52 is a view for explaining a schematic constitution of another stimulation unit in a biological optical measurement instrument representing the embodiment 20 according to the present invention.

Further, as a stimulation unit suitable for a baby, an incubator 5001 can be used in which at the upper face portion of a well known incubator a fixing mechanism 5002 is provided and the display unit 4904 is disposed at the fixing mechanism 5002. With the stimulation unit as shown in FIG. 52, since the subject 214 is laid in the incubator 5001, the movement in the body axis direction is restricted. Accordingly, the present embodiment is suitable for giving light stimulation to a baby who has difficulty of directing the line of sight upward and biological optical measurement causing the line of sight downward can be performed easily.

In the stimulation unit as shown in FIG. 52, if a well known sliding mechanism is provided for the fixing unit 5002 and setting the sliding direction to the body axis direction of the subject 214, namely, the longitudinal direction of the incubator 5001, stimulation can be given to the subject under an optimum condition regardless to the set position of the subject 214.

Embodiment 21

Figure 53:
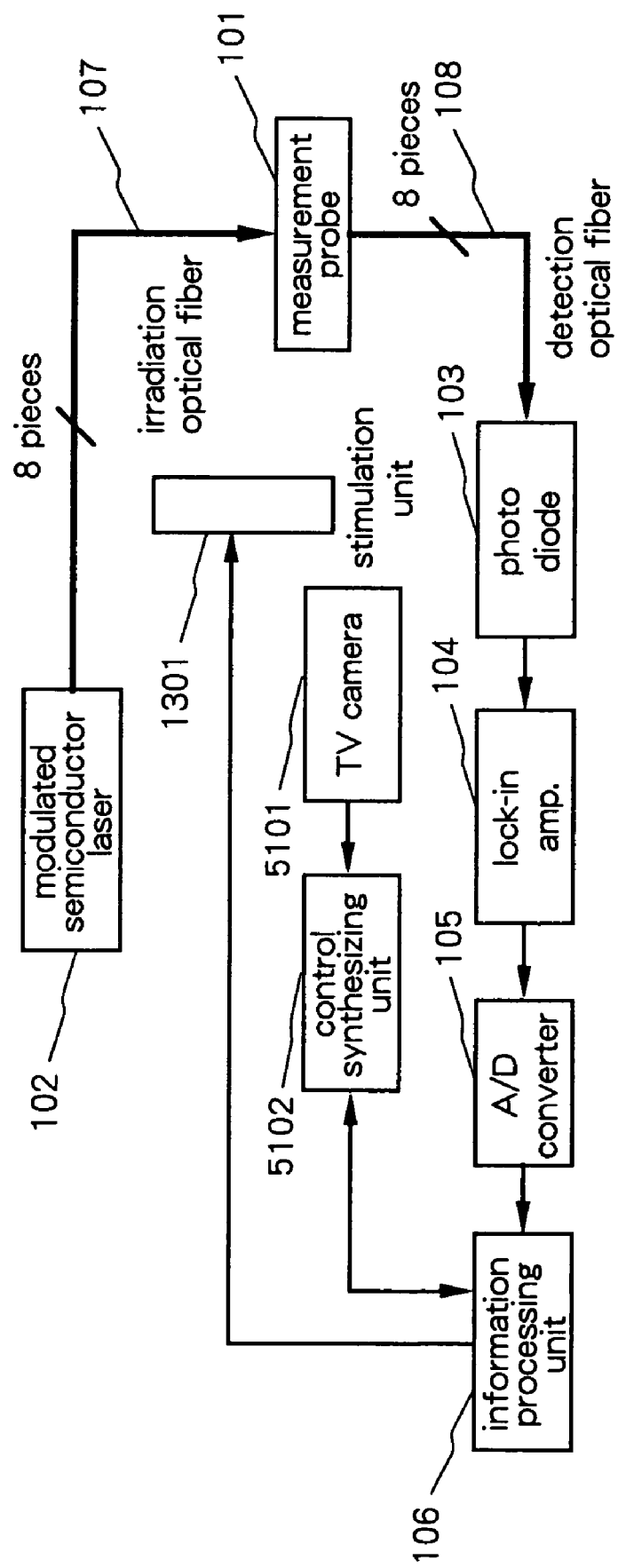
FIG. 53 is a diagram for explaining a schematic constitution of a biological optical measurement instrument representing embodiment 21 according to the present invention.

FIG. 53 is a view for explaining a schematic structure of a biological optical measurement instrument representing the embodiment 21 according to the present invention, wherein 5101 shows a video camera and 5102 a control synthesizing unit. However, in the following explanation, only the video camera 5101 and the control synthesizing unit Si02 will be explained, which is different from that in the biological optical measurement instrument according to the embodiments 1 and 4.

In FIG. 53, the video camera 5101 is a well known video camera which takes picture and records the same of the behavior of the not shown subject 214, and in the embodiment 21, the video camera is set so as to permit picture taking, in particular, at the front face of the subject 214, namely, at the side where the stimulation unit 1301 is disposed.

The control synthesizing unit 5102 commands to the video camera 5101 to start and end the photograph recording of the subject 214 based on the measurement start from the information processing unit 106 as well as outputs the lapsed time from the photograph recording start to the information processing unit 106. Further, the control synthesizing unit 5102 outputs a picture image at a designated time to the information processing unit 106 based on a reproduction command from the information processing unit 106. The reproduced picture image is displayed on the display screen of the not shown display unit connected to the information processing unit 106.

Figure 54:
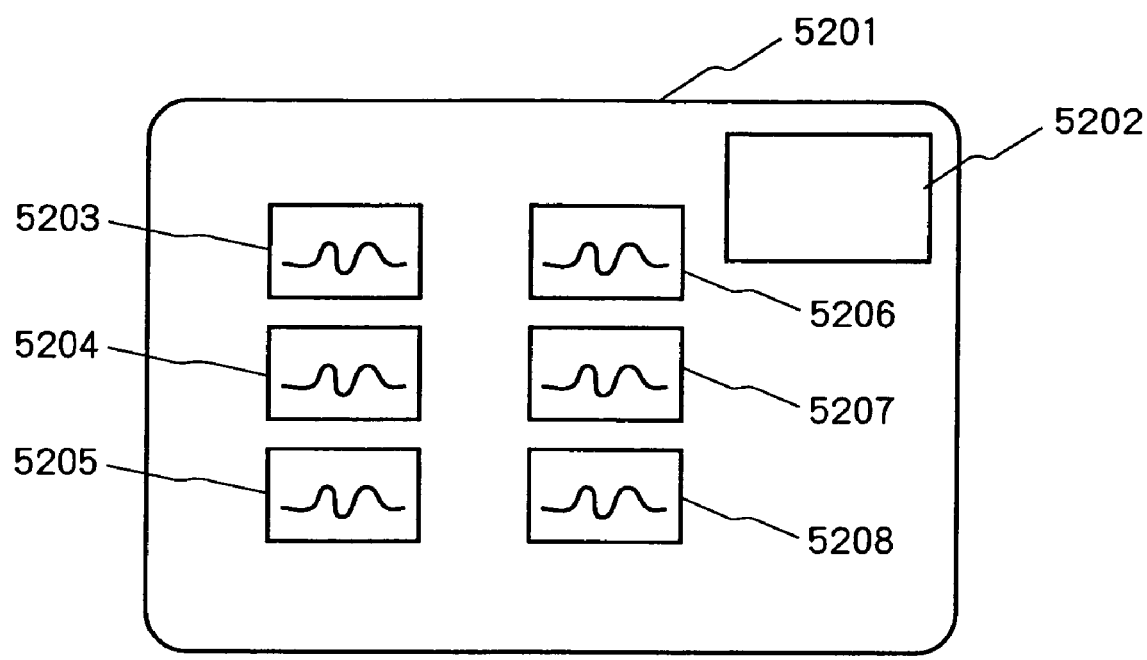
FIG. 54 is a view showing a display example by the biological optical measurement instrument representing the embodiment 21 according to the present invention.

Now, FIG. 54 shows a display example by the biological optical measurement instrument according to the embodiment 21 and hereinbelow an operation of the biological optical measurement instrument according to the embodiment 21 will be explained with reference to FIG. 54.

In FIG. 54, 5201 shows a display screen, 5202 a display region of reproduced picture image, 5203-5208 are display regions of measurement results.

A photograph recorded condition of the subject 214 is reproduced and displayed on the display region 5202 for reproduced picture image, and measurement results in the measurement data obtained at that time are displayed on the display regions 5203-5208.

As has been explained hitherto, with the biological measurement instrument according to the embodiment 21, since the state of the subject 214 at the time of measurement can be always measured, in particular, when analyzing the biological optical measurement results of a baby as the subject 214, whether the subject 214 shows an interest to a stimulation, namely, recognizes the stimulation can be confirmed. As a result, an analysis can be performed only on the measurement results at the time when the subject 214 recognizes the stimulation, thereby, an accurate analysis can be effected. Accordingly, necessity of such as re-measurement and a plurality of same measurements can be avoided, thereby, diagnosis efficiency, in other words, measurement efficiency can be enhanced.

Embodiment 22

Figure 55:
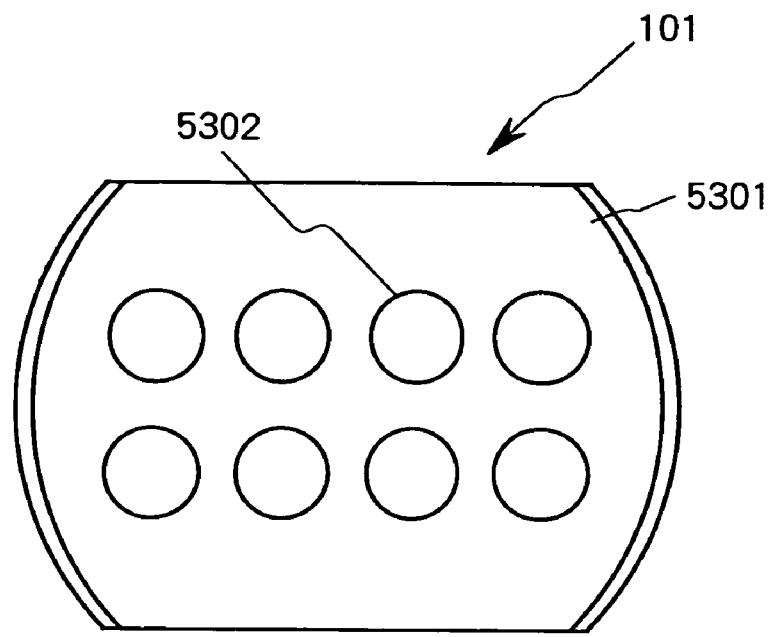
FIGS. 55(a) and 55(b) are views for explaining a schematic constitution of a measurement probe in a biological optical measurement instrument representing embodiment 22 according to the present invention.
Figure 55:
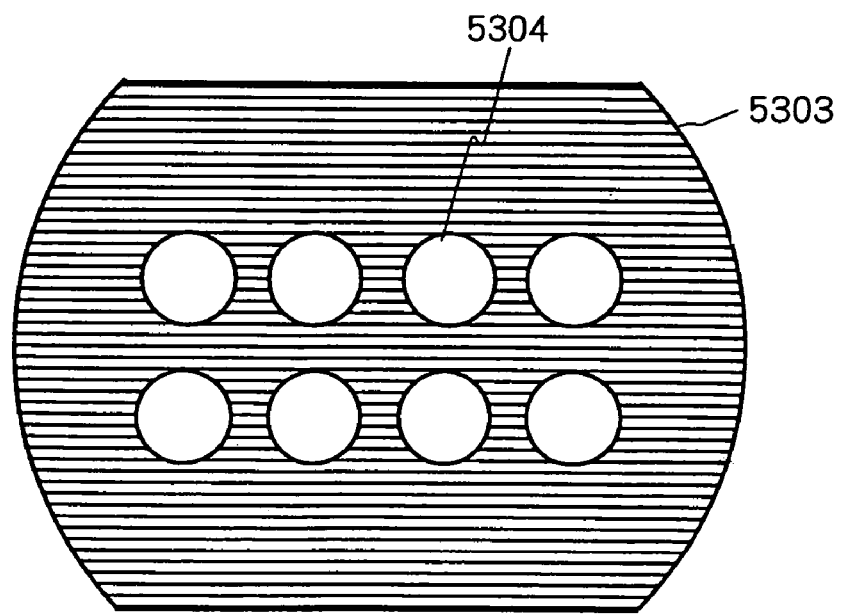
Figure 56:
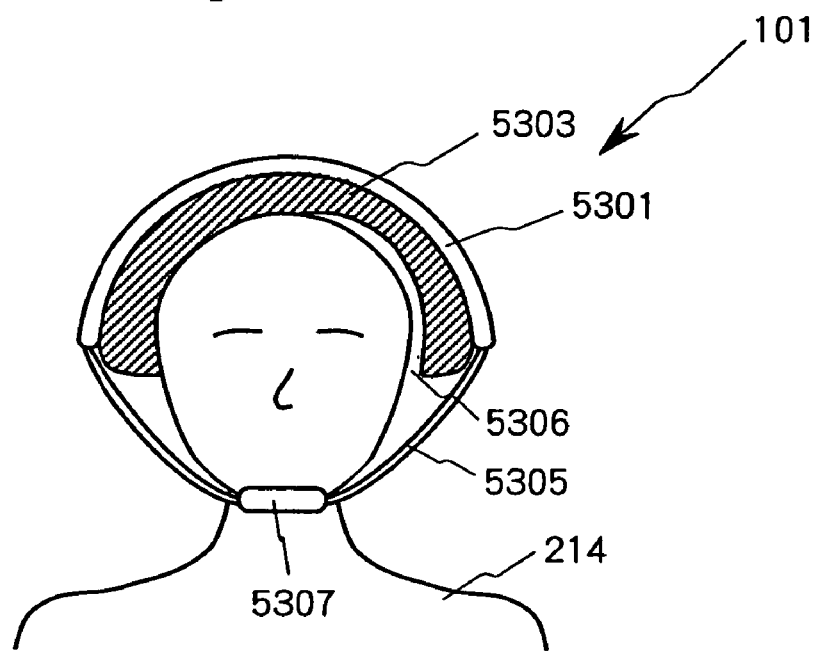
FIGS. 56(a) and 56(b) are views for explaining an attachment state of the measurement probe of the embodiment 22 according to the present invention.
Figure 56:
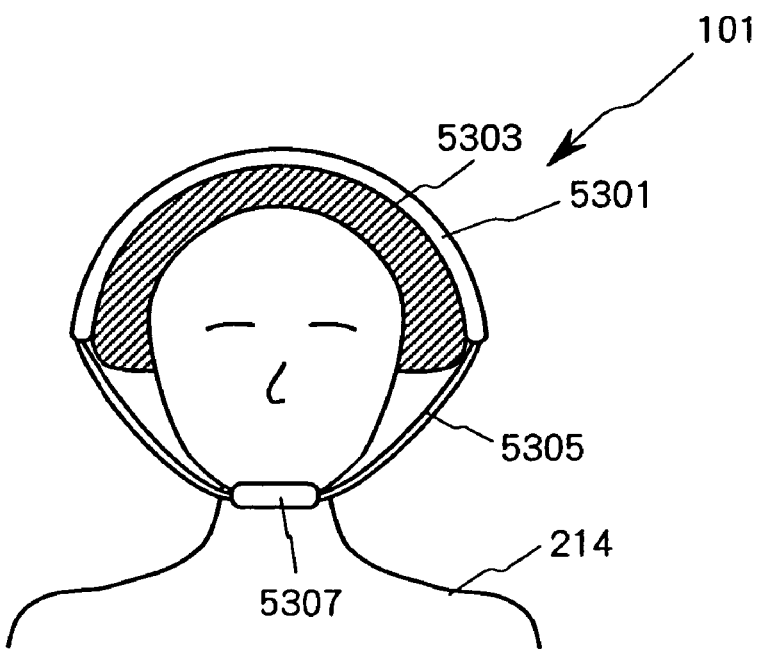

FIGS. 55(a) and 55(b) are views for explaining a schematic constitution of a measurement probe 101 in a biological optical measurement instrument representing the embodiment 22 according to the present invention, and FIGS. 56(a) and 56(b) are views for explaining an attachment state of the measurement probe 101 of the embodiment 22 according to the present invention. In particular, FIG. 55(a) is a view for explaining a schematic structure of a shell plate, FIG. 55(b) is a view for explaining an air balloon, FIG. 56(a) is a view for explaining a state immediately after attachment of the measurement probe 101 and FIG. 56(b) is a view for explaining a state in which air is charged into the air balloon. However, in the following explanation, only the structure relating to the present embodiment. 22 in the measurement probe 101 will be explained which is different from that in the biological optical measurement instrument according to the embodiment 1.

As shown in FIG. 55(a), a shell plate 5301 according to the embodiment 22 is constituted in the same manner as the previous shell plates. At the end portions of the shell plate not shown belts 5305 are disposed which fix the shell plate 5301 to the subject 214. However, for the sake of simple explanation, probe holders are omitted and only the holes to which the probe holders are disposed are illustrated.

The air balloon 5303 is formed from such as resin having flexibility, for example, like a well known rubber ring and opening portions 5304 are formed at positions corresponding to holes 5302 provided for the shell plate 5301 as shown in FIG. 55(b), not shown air charging port is formed for the air balloon 5303 and through charging air from the air charging port the air balloon 5303 expands to a predetermined volume.

Now, an attachment sequence and advantage of the measurement probe 101 according to the embodiment 22 will be explained with reference to FIGS. 56(a) and 56(b).

As will be seen from FIG. 56(a), head portions of subjects 214 show a variety of shapes depending on individual difference, therefore, with a shell plate 5301 prepared in advance it is possible that a gap 5306 between the shell plate 5301 and the head portion occurs. Namely, since a contacting area between the shell plate 5301 and the head portion becomes small, a possible displacement of the shell plate 5301 likely occurs.

Accordingly, as shown in FIG. 56(b), if the air balloon 5303 is disposed between the shell plate 5301 and the head portion and air is charged thereinto, the air balloon 5303 fills the gap 5306 between the shell plate 5301 and the head portion, namely, the measurement probe 101 is closely contacted to the subject 214, thereby, the possible displacement of the measurement probe 101 can be prevented. As a result, accuracy of biological optical measurement can be enhanced. Further, since the displacement of the measurement probe 101 can be prevented, re-measurement due to the displacement can be reduced, thereby, diagnosis efficiency can be enhanced.

At a belt 5305 provided for the shell plate 5301 according to the embodiment 22 a chin use plate 5307 is disposed and the chin use plate 5307 is applied to the chin of the subject 214. Namely, since a possible displacement of the shell plate 5301 due to expansion of the air balloon 5303 is restricted by the belt 5305, the measurement probe 101 can be contacted closely to the subject 214.

Embodiment 23

Figure 57:
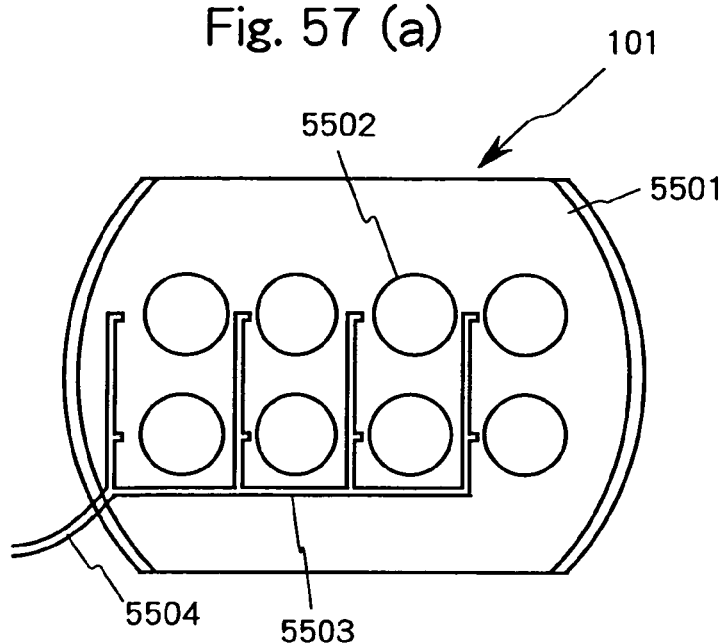
FIGS. 57(a), 57(b) and 57(c) are views for explaining a schematic constitution of a measurement probe in a biological optical measurement instrument representing embodiment 23 according to the present invention.
Figure 57:
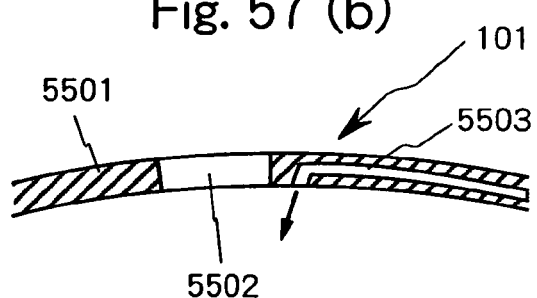
Figure 57:
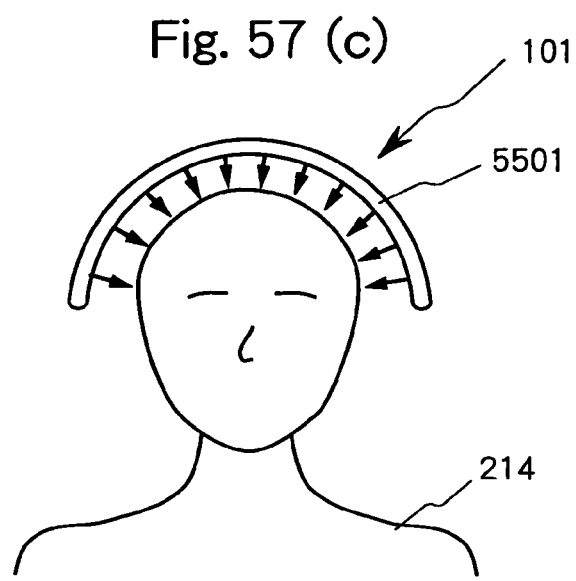

FIGS. 57(a), 57(b) and 57(c) are views for explaining a schematic constitution of a measurement probe 101 in a biological optical measurement instrument representing the embodiment 23 according to the present invention, and, in particular, FIG. 57(a) is a view for explaining a schematic structure of a shell plate, FIG. 57(b) is a vertical cross sectional side view of the shell plate and FIG. 57(c) is a view for explaining an attached state of the measurement probe 101. However, in the following explanation, only the structure of the shell plate relating to the present embodiment 23 in the measurement probe 101 will be explained which is different from that in the biological optical measurement instrument according to the embodiment 1.

As will be seen from FIG. 57(a), in a shell plate 5501 according to the embodiment 23 passages 5503 are formed which lead air near to holes 5502 into which not shown probe holders are disposed. Accordingly, one ends of the respective air passages 5503 are collected together and are connected to an air hose. On the other hand, the other ends of the air passages 5503 are opened to the side of a subject on the shell plate 5501. Compressed air is supplied to the air hose 5504.

Accordingly, as shown in FIGS. 57(b) and 57(c), since the compressed air supplied through the air passages 5503 is injected as shown by arrows to the attachment positions of the probe holders forming the opening portions, namely, to the positions where the end portions of the not shown optical fibers 107 and 108, a possible hair is displaced by the injected compressed air and the skin is exposed at the air injected portions. In other words, the hair avoiding work at the time when attaching the not shown probe casings is unnecessitated, thereby, attachment of the measurement probe is facilitated. As a result, diagnosis efficiency can be enhanced. Further, the hair avoiding work can be performed only by injecting compressed air without injuring the scalp of the subject 214. Optimum position and angle of the opening portions through which compressed air is injected are determined for every probe casing and shell plate through measurement in advance.

Further, in the embodiments according to the present invention, a semiconductor laser is used as the light source, however, the present invention is not limited thereto, for example, light sources such as titanium-sapphire laser and a light emitting diode can be, of course, used therefor.

Still further, a living body passed light intensity picture image which is display picture image data obtained through three dimensional spline interpolation computation, other than displaying on the display unit, can be, of course, stored, for example, such as in a magnetic disk unit and an optical disk unit representing a not shown external memory unit connected to the information processing unit 106.

Still further, it is, of course, possible to display superposedly of the living body passed light intensity picture image stored in the external memory unit over a three dimensional image measured such as by an X ray CT device and an MR device.

Figure 58:
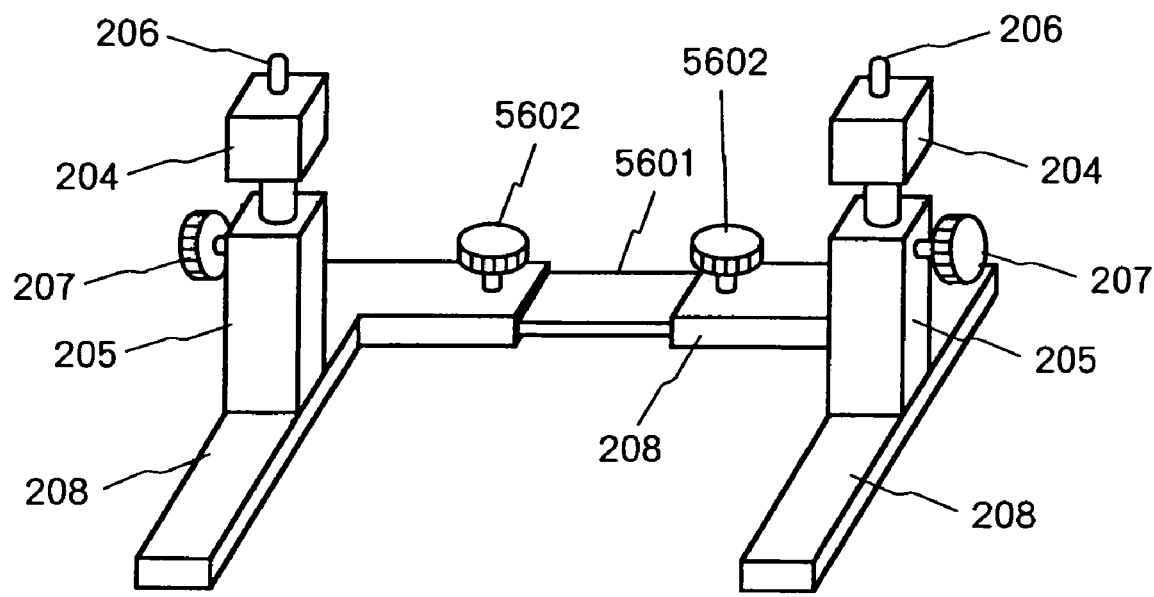
FIGS. 58(a) and 58(b) are views for explaining a schematic constitution of another supporting member used in a measurement probe according to the present invention.
Figure 58:
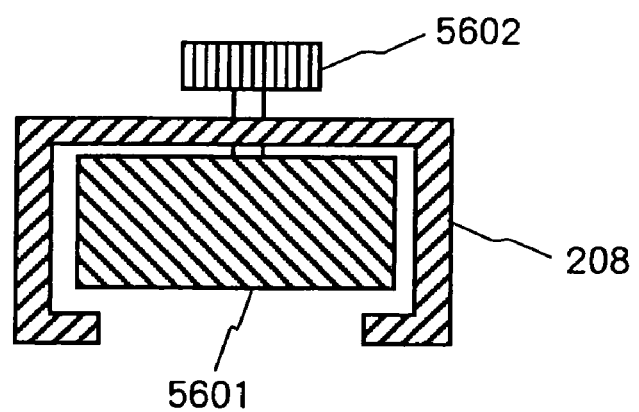

Still further, in the measurement probes 101 according to the embodiments the length in the longitudinal direction of the pillow base 208, namely, the length in the hanging direction of the belt 202 is fixed, however, the structure of the pillow base 208 is not limited thereto, for example, as shown in FIG. 58(*a*), the pillow base 208 is divided into two parts in its longitudinal direction, between the two parts a well known rail mechanism is provided in which a rail 5601 is disposed, a well known fixing mechanism is also provided which fixes the divided pillow base 208 and the rail 5601 by screws 5602, thereby, the interval between the support pillars 205 can be adjustable, thus, a measurement which is most suitable for the size of the head portion of a subject 214 can be performed. FIG. 58(*b*) is a vertical cross sectional side view of a part of the rail mechanism and as will be seen from FIG. 58(*b*) the cross section of the pillow base 208 is formed in an inverted U shape. The rail 5601 is inserted into the space of the pillow base 208 and is fixed thereto by the screws 5602, thereby, the interval between the support pillars 205 can be adjusted to a desired one.

Hereinabove, the invention carried out by the present inventors has been explained specifically with reference to the embodiments according to the present invention, however, the present invention is not limited to the embodiments according to the present invention, and the embodiments can be, of course, modified in a variety of manners without departing the gist of the present invention.

The followings are simple summary of advantages obtained by typical embodiments among the invention disclosed in the present specification;

(1) A biological optical measurement can be performed for a subject in lateral decubitus.

(2) Hair avoiding work at the time of attaching a measurement probe can be performed easily.

(3) A biological optical measurement can be performed while providing a predetermined stimulation onto a subject.

(4) Diagnosis efficiency can be enhanced.

What is claimed is:

1. A biological optical measurement instrument comprising:
a measurement probe adapted to be positioned to a surface of a subject, which irradiates light beams having a plurality of wavelengths from a light beam source through optical fibers onto the subject, and collects the light beams passed inside the subject from a plurality of positions to facilitate production of diagnostics from collected light beams of the subject, wherein the measurement probe is provided with probe casings formed in a cylindrical shape, which hold the optical fibers, fixing members to position the probe casings in a predetermined interval, and a support member which supports the fixing members and which is adapted to be attached to a head portion of the subject, and wherein the respective fixing member is provided with a predetermined width along an inner circumference thereof to permit fixed engagement of the respective probe casing with the respective fixing member, and a moveable support mechanism where a subject-contacting end portion of the optical fibers is movably retractable relative to the subject while supported in the fixed engagement with the respective fixing member.

2. A biological optical measurement instrument according to claim 1, wherein at least one of the respective probe casing or the respective fixing member is provided with a fixing groove having a predetermined width, which engages with a stopper claw on the other of the respective probe casing of the respective fixing member, for the fixed engagement.

3. A biological optical measurement instrument according to claim 2, wherein the fixing groove has a predetermined size.

4. A biological optical measurement instrument according to claim 2, wherein the probe casing is provided with the stopper claw, and the fixing member is provided with the fixing groove.

5. A biological optical measurement instrument according to claim 4, wherein a shape of a part the stopper claw, projecting to the optical fiber fixing member, has a projection amount thereof gradually increased in a direction opposite to a direction of inserting the probe casing into the fixing member.

6. A biological optical measurement instrument according to claim 2, comprising a fixing groove having a predetermined size formed along an inner circumference of each of the fixing member.

7. A biological optical measurement instrument according to claim 4, wherein a spring mechanism is built-in in the probe casing, with the spring mechanism cooperating with the stopper claw to bias engagement thereof with the fixing groove, and with the spring mechanism being operable to disengage the stopper claw from the fixing groove.

8. A biological optical measurement instrument according to claim 4, wherein a release button is operable integral with the stopper claw, and when the release button is pressed, the stopper claw is retreated into the probe casing and the probe casing is released from the optical fiber fixing member.

9. A biological optical measurement instrument according to claim 4, wherein each of the probe casings is provided with a stopper claw near a predetermined end portion thereof so as to permit engagement with the fixing groove.

10. A biological optical measurement instrument according to claim 1, wherein the fixing member is provided with a stopper claw so as to properly position the probe casing.

11. A biological optical measurement instrument according to claim 1, wherein a guide slit is provided within the probe casing, and a slide member is arranged along the guide slit.

12. A biological optical measurement instrument according to claim 1, wherein ones of the fixing members have a substantially cylindrical shape.

13. A biological optical measurement instrument according to claim 1, comprising the moveable support mechanism being a spring pressing mechanism adapted to press the subject-contacting portion of an optical fiber onto the subject through a force pushing out the optical fiber by the spring pressing mechanism.

14. A biological optical measurement instrument according claim 13, wherein the spring pressing mechanism is adapted to keep a compressed condition when the subject-contacting end portion of the optical fibers is adapted to be confronted to the subject.

15. A biological optical measurement instrument comprising:

a measurement probe adapted to be positioned against a surface of a subject, which irradiates light beams having a plurality of wavelengths from a light beam source through optical fibers onto the subject, and collects the light beams passed inside the subject from a plurality of positions to facilitate production of diagnostics from collected light beams from the subject, wherein the measurement probe is provided with probe casings formed in a cylindrical shape, which hold the optical fibers, fixing members to position the probe casings in a predetermined interval, and a support member which supports the fixing members and which is adapted to be attached to a head portion of the subject, and wherein the respective fixing member is provided with a predetermined width along an inner circumference thereof to permit fixed engagement of the respective probe casing with the respective fixing member, and a retractable movement mechanism to allow a subject-contacting end portion of the optical fibers to be retractably movable into the respective probe casing relative to the surface of the subject.

16. A biological optical measurement instrument comprising:

a measurement probe adapted to be positioned against a surface of a subject, which irradiates light beams having a plurality of wavelengths from a light beam source through optical fibers onto the subject, and collects the light beams passed inside the subject from a plurality of positions to facilitate production of diagnostics from collected light beams from the subject, wherein the measurement probe is provided with probe casings formed in a cylindrical shape, which hold the optical fibers, fixing members to position the probe casings in a predetermined interval, and a support member which supports the fixing members and which is adapted to be attached to a head portion of the subject, and wherein the respective fixing member is provided with a predetermined width along an inner circumference thereof to permit fixed engagement of the respective probe casing with the respective fixing member, and a swing mechanism to allow a subject-contacting end portion of the optical fibers to be swingable in a predetermined manner to change an angle of the subject-contacting end portion relative to the surface of the subject.

* * * * *